US010919928B2

(12) United States Patent
Hirai et al.

(10) Patent No.: US 10,919,928 B2
(45) Date of Patent: *Feb. 16, 2021

(54) OLIGONUCLEOTIDE PRODUCTION METHOD, AND NUCLEOSIDE, NUCLEOTIDE, OR OLIGONUCLEOTIDE

(71) Applicant: AJINOMOTO CO., INC., Tokyo (JP)

(72) Inventors: Kunihiro Hirai, Kawasaki (JP); Satoshi Katayama, Kawasaki (JP); Naoko Hirose, Kawasaki (JP); Taisuke Ichimaru, Kawasaki (JP); Ken Yamashita, Kawasaki (JP); Daisuke Takahashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 71 days.

This patent is subject to a terminal disclaimer.

(21) Appl. No.: 16/009,533

(22) Filed: Jun. 15, 2018

(65) Prior Publication Data

US 2018/0282365 A1 Oct. 4, 2018

Related U.S. Application Data

(63) Continuation of application No. PCT/JP2016/087654, filed on Dec. 16, 2016.

(30) Foreign Application Priority Data

Dec. 16, 2015 (JP) .............................. JP2015-245564

(51) Int. Cl.
| | | |
|---|---|---|
| C07H 21/02 | (2006.01) | |
| C07H 21/04 | (2006.01) | |
| C12N 15/09 | (2006.01) | |
| C07H 19/167 | (2006.01) | |
| C07H 19/20 | (2006.01) | |
| C07H 1/00 | (2006.01) | |

(Continued)

(52) U.S. Cl.
CPC ............. *C07H 21/02* (2013.01); *C07H 1/00* (2013.01); *C07H 19/067* (2013.01); *C07H 19/073* (2013.01); *C07H 19/10* (2013.01); *C07H 19/167* (2013.01); *C07H 19/173* (2013.01); *C07H 19/20* (2013.01); *C07H 21/00* (2013.01); *C07H 21/04* (2013.01); *C12N 15/09* (2013.01)

(58) Field of Classification Search
CPC ........ C07H 19/10; C07H 19/20; C07H 21/02; C07N 15/09

See application file for complete search history.

(56) References Cited

U.S. PATENT DOCUMENTS

| | | | |
|---|---|---|---|
| 8,846,885 B2 * | 9/2014 | Hirai ................... | C07H 19/073 536/22.1 |
| 9,029,528 B2 * | 5/2015 | Hirai ..................... | C07H 21/00 536/25.34 |

(Continued)

FOREIGN PATENT DOCUMENTS

| | | |
|---|---|---|
| EP | 2 816 053 A1 | 12/2014 |
| JP | 2010-275254 A | 12/2010 |

(Continued)

OTHER PUBLICATIONS

Shokaku Kim, et al., "Liquid-Phase RNA Synthesis by Using Alkyl-Chain-Soluble Support", Chemistry: A European Journal, vol. 19, 2013, pp. 8615-8620.

(Continued)

*Primary Examiner* — Lawrence E Crane
(74) *Attorney, Agent, or Firm* — Oblon, McClelland, Maier & Neustadt, L.L.P.

(57) ABSTRACT

Oligonucleotides may be produced by a process, including (1) condensing a nucleoside, nucleotide or oligonucleotide (b), and a nucleoside, nucleotide or oligonucleotide (a), or a substituted nucleotide or oligonucleotide (α) in a non-polar solvent to give a reaction solution containing a phosphite triester product (c); (3) oxidizing or sulfurizing the phosphite triester product (c) to give a reaction solution containing an oligonucleotide (d) wherein the 5'-hydroxy group is protected; (4) deprotecting the oligonucleotide (d) to give a reaction solution containing an oligonucleotide (e) wherein the 5'-hydroxy group is not protected; and (6) adding a polar solvent to the reaction solution containing the oligonucleotide (e) and purifying the oligonucleotide (e) by solid-liquid separation, wherein said nucleoside, nucleotide or oligonucleotide (a) or said substituted nucleotide or oligonucleotide (α) is a compound represented by formula (a-i):

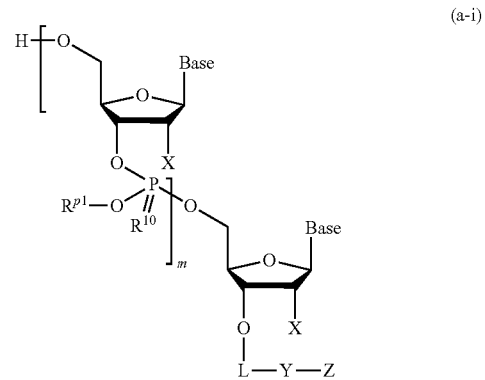

wherein Base, $R^{P1}$, $R^{10}$, m, L, Y, and Z are defined herein.

39 Claims, No Drawings

Specification includes a Sequence Listing.

(51) Int. Cl.
*C07H 19/10* (2006.01)
*C07H 21/00* (2006.01)
*C07H 19/073* (2006.01)
*C07H 19/173* (2006.01)
*C07H 19/067* (2006.01)

(56) References Cited

U.S. PATENT DOCUMENTS

| | | | |
|---|---|---|---|
| 9,284,344 B2 * | 3/2016 | Kim | C07H 21/04 |
| 9,371,353 B2 * | 6/2016 | Hirai | C07H 19/073 |
| 10,214,555 B2 * | 2/2019 | Nonogawa | C07H 19/067 |
| 2012/0296074 A1 | 11/2012 | Hirai et al. | |
| 2013/0267697 A1 | 10/2013 | Hirai et al. | |
| 2015/0112053 A1 | 4/2015 | Kim et al. | |
| 2015/0315229 A1 | 11/2015 | Nonogawa | |
| 2017/0320904 A1 | 11/2017 | Hirai et al. | |

FOREIGN PATENT DOCUMENTS

| | | |
|---|---|---|
| JP | 2012-111728 A | 6/2012 |
| WO | WO 2005/070859 A1 | 8/2005 |
| WO | WO 2012/157723 A1 | 11/2012 |
| WO | WO 2013/122236 A1 | 8/2013 |
| WO | WO 2013/179412 A1 | 12/2013 |
| WO | WO 2014/077292 A1 | 5/2014 |
| WO | WO 2016/117663 A1 | 7/2016 |
| WO | WO 2017/086397 A1 | 5/2017 |
| WO | WO 2017/111137 A1 | 6/2017 |

OTHER PUBLICATIONS

Takao Shoji, et al., "Synthesis of Conjugated Oligonucleotide in Solution Phase Using Alkyl-chain-soluble Support", Chem. Lett., vol. 43, 2014, pp. 1251-1253.

Extended European Search Report dated Sep. 12, 2019, in Patent Application No. 16875810.0, 4 pages.

Mishra, R. et al., "Synthesis and Application of Fluorous-tagged Oligonucleotides", Chemistry Letters, XP009099520, vol. 35, No. 10, Sep. 27, 2006, pp. 1184-1185.

* cited by examiner

OLIGONUCLEOTIDE PRODUCTION METHOD, AND NUCLEOSIDE, NUCLEOTIDE, OR OLIGONUCLEOTIDE

CROSS REFERENCES TO RELATED APPLICATIONS

This application is a continuation of International Patent Application No. PCT/JP2016/087654, filed on Dec. 16, 2016, and claims priority to Japanese Patent Application No. 2015-245564, filed on Dec. 16, 2015, both of which are incorporated herein by reference in their entireties.

BACKGROUND OF THE INVENTION

Field of the Invention

The present invention relates to production methods of oligonucleotides. The present invention also relates to nucleosides, nucleotides, and oligonucleotide effectively usable in such a production method.

Discussion of the Background

As a production method of oligonucleotides, a solid phase method using a phosphoramidite method is widely used at present (see S. L. Beaucage, D. E. Bergstorm, G. D. Glick, R. A. Jones, Current Protocols in Nucleic Acid Chemistry; John Wiley & Sons (2000), which is incorporated herein by reference in its entirety). The solid phase method is advantageous from the aspect of speed, since process has been optimized and automation has progressed. However, it is associated with defects in that scaling-up is limited due to facility restriction. In addition, a production method of oligonucleotide by a liquid phase method has also been studied. However, since the operation is complicated and the yield is low, and therefore, a large-scale, rapid synthesis of long oligonucleotide is difficult.

In recent years, in an attempt to solve the respective defects of the solid phase method and liquid phase method, a production method using a hydrophobic group-linked nucleoside (see JP-A-2010-275254, which is incorporated herein by reference in its entirety), a production method using a nucleoside or oligonucleotide having the 3'-hydroxy group protected by a particular organic group (see WO 2012/157723, which is incorporated herein by reference in its entirety) and the like have been disclosed.

The aforementioned WO 2012/157723 describes a production method of oligonucleotide, including the following steps (i)-(iv):

(i) removing a 5'-hydroxy-protecting group (e.g., dimethoxytrityl group) of a nucleoside or oligonucleotide (deprotection), (ii) condensing a nucleoside or oligonucleotide obtained by deprotection and a nucleoside or oligonucleotide wherein a 3'-hydroxy group is phosphoramidited and a 5'-hydroxy group is protected, (iii) oxidizing or sulfurizing a phosphite triester product obtained by the condensation, and (iv) solid-liquid separating an oligonucleotide having the protected 5'-hydroxy group, which is obtained by the oxidation or sulfurization. The oligonucleotide chain can be elongated by repeating the aforementioned steps (i)-(iv).

However, there remains a need for improved methods of preparing oligonucleotides.

SUMMARY OF THE INVENTION

Accordingly, it is one object of the present invention to provide novel production methods of oligonucleotides, capable of efficiently performing condensation.

These and other objects, which will become apparent during the following detailed description, have been achieved by the inventors' discovery that condensation can be efficiently performed by changing the order of the steps described in WO 2012/157723 and performing (I) condensing a nucleoside, nucleotide or oligonucleotide (a) wherein a 5'-hydroxy group is not protected, and at least one group of a 3'-hydroxy group and the like is protected by a protecting group, and a nucleoside, nucleotide or oligonucleotide (b) wherein a 3'-hydroxy group or 3'-amino group is phosphoramidited and a 5'-hydroxy group is protected, (II) oxidizing or sulfurizing a phosphite triester product (c) obtained by the condensation, (III) removing the 5'-hydroxy-protecting group from an oligonucleotide (d) obtained by the oxidation or sulfurization (deprotection), and (IV) purifying by solid-liquid separating or extracting an oligonucleotide (e) wherein the 5'-hydroxy group is not protected, which is obtained by the deprotection.

To repeat the steps (i)-(iv) described in WO 2012/157723, condensation (step (ii)) is performed after deprotection (step (i)). To repeat the aforementioned steps (I)-(IV), condensation (step (I)) is performed after solid-liquid separation or extraction (step (IV)). Therefore, in the production method containing the aforementioned steps (I)-(IV), an impurity produced by deprotection is absent during condensation, and condensation can be performed efficiently.

Thus, the present invention provides:

(1) A method for producing an oligonucleotide, comprising the following steps (1), (3), (4) and (6):

(1) condensing, in a non-polar solvent, a nucleoside, nucleotide or oligonucleotide (b) wherein a 3'-hydroxy group or 3'-amino group is phosphoramidited, a 5'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis, and a nucleoside, nucleotide or oligonucleotide (a) wherein a 5'-hydroxy group is not protected, at least one group selected from an amino group and an imino group of a nucleic acid base, a 2'-hydroxy group, a 3'-hydroxy group and a 3'-amino group of a ribose residue, and a 3'-hydroxy group and a 3'-amino group of a deoxyribose residue is protected by a protecting group unremovable under acidic conditions but removable under basic conditions, and other groups are optionally protected by a protecting group used for nucleic acid synthesis, or a substituted nucleotide or oligonucleotide (α) wherein a 5'-hydroxy group is not protected, one hydroxy group of a 3'-phosphoric acid group is replaced by $-OL^{n1}$-OH wherein $L^{n1}$ is an organic group, the hydroxy group of $-OL^{n1}$-OH is protected by a protecting group unremovable under acidic conditions but removable under basic conditions, and other groups are optionally protected by a protecting group used for nucleic acid synthesis by adding the nucleoside, nucleotide or oligonucleotide (b) to a reaction solution comprising the nucleoside, nucleotide or oligonucleotide (a) or the substituted nucleotide or oligonucleotide (α) to give a reaction solution comprising a phosphite triester product (c) wherein the 5'-hydroxy group is protected by the temporary protecting group removable under acidic conditions;

(3) oxidizing or sulfurizing the phosphite triester product (c) by adding an oxidant or a sulfurizing agent to the reaction solution comprising the phosphite triester product (c) to give a reaction solution comprising an oligonucleotide (d) wherein the 5'-hydroxy group is protected by the temporary protecting group removable under acidic conditions;

(4) removing the temporary protecting group of the 5'-hydroxy group by adding an acid to the reaction solution after the oxidation or sulfurization to give a reaction solution comprising an oligonucleotide (e) wherein the 5'-hydroxy group is not protected; and (6) adding a polar solvent to the reaction solution comprising the oligonucleotide (e) and purifying the oligonucleotide (e) by solid-liquid separation or extraction.

(2) The production method of the aforementioned (1), wherein
a nucleoside, nucleotide or oligonucleotide (a) wherein a 5'-hydroxy group is not protected, at least one group selected from an amino group and an imino group of a nucleic acid base, a 2'-hydroxy group and a 3'-hydroxy group of a ribose residue, and a 3'-hydroxy group of a deoxyribose residue is protected by a protecting group unremovable under acidic conditions but removable under basic conditions, and other groups are optionally protected by a protecting group used for nucleic acid synthesis, or
a substituted nucleotide or oligonucleotide (α) wherein a 5'-hydroxy group is not protected, one hydroxy group of a 3'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis, and
a nucleoside, nucleotide or oligonucleotide (b) wherein a 3'-hydroxy group is phosphoramidited, a 5'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are used in step (1).

(3) The production method of the aforementioned (1), wherein
a nucleoside or oligonucleotide (a) wherein a 5'-hydroxy group is not protected, at least one group selected from an amino group and an imino group of a nucleic acid base, a 2'-hydroxy group and a 3'-hydroxy group of a ribose residue, and a 3'-hydroxy group of a deoxyribose residue is protected by a protecting group unremovable under acidic conditions but removable under basic conditions, and other groups are optionally protected by a protecting group used for nucleic acid synthesis, and
a nucleoside or oligonucleotide (b) wherein a 3'-hydroxy group is phosphoramidited, a 5'-hydroxy group is protected by a temporary protecting group removable under acidic conditions, and other groups are optionally protected by a protecting group used for nucleic acid synthesis are used in step (1).

(4) The production method of any one of the aforementioned (1) to (3), further comprising the following step (2) after step (1) and before step (3):
(2) adding a quencher to the reaction solution after condensation.

(5) The production method of the aforementioned (4), wherein the quencher used in step (2) is at least one selected from alcohols, phenols and amines.

(6) The production method of any one of the aforementioned (1) to (5), wherein a mixture of a carboxylic acid and an organic base, an inorganic acid or an amine is added to the reaction solution after step (1) and before step (4), and 5-[(N,N-dimethylaminomethylidene)amino]-3H-1,2,4-dithiazole-3-thione is added to the reaction solution as a sulfurizing agent in step (3).

(7) The production method of the aforementioned (6), wherein an amount of a basic nitrogen atom of the organic base is 1 to 2 mol per 1 mol of carboxy group of the carboxylic acid.

(8) The production method of any one of the aforementioned (1) to (5), wherein the sulfurizing agent used in step (3) is at least one selected from 3H-1,2-benzodithiol-3-one-1,1-dioxide, 3H-1,2-benzodithiol-3-one, phenylacetyl disulfide, tetraethylthiuram disulfide, dipentamethylenethiuram tetrasulfide, phenyl-3H-1,2,4-dithiazol-3-one, 3-amino-1,2,4-dithiazole-5-thione and sulfur.

(9) The production method of any one of the aforementioned (1) to (5), wherein the oxidant used in step (3) is at least one selected from iodine, (1S)-(+)-(10-camphanylsulfonyl)oxaziridine, tert-butyl hydroperoxide, 2-butanone peroxide, 1,1-dihydroperoxycyclododecane, bis(trimethylsilyl)peroxide and m-chloroperbenzoic acid.

(10) The production method of any one of the aforementioned (1) to (9), wherein the temporary protecting group is a dimethoxytrityl group or a monomethoxytrityl group.

(11) The production method of any one of the aforementioned (1) to (10), wherein the non-polar solvent is at least one selected from a halogenated solvent, an aromatic solvent, an ester solvent and an aliphatic solvent.

(12) The production method of any one of the aforementioned (1) to (11), wherein the acid used in step (4) is at least one selected from trifluoroacetic acid, dichloroacetic acid, trifluoromethanesulfonic acid, trichloroacetic acid, methanesulfonic acid, hydrochloric acid, acetic acid and p-toluenesulfonic acid.

(13) The production method of any one of the aforementioned (1) to (12), wherein the protecting group unremovable under acidic conditions but removable under basic conditions has a linear aliphatic hydrocarbon group having a carbon number of not less than 10, or an organic group having at least one aliphatic hydrocarbon group having one or more branched chains and having a total carbon number of not less than 14 and not more than 300.

(14) The production method of any one of the aforementioned (1) to (13), wherein step (6) comprises adding a polar solvent to the reaction solution comprising the oligonucleotide (e) and purifying the oligonucleotide (e) by solid-liquid separation.

(15) The production method of any one of the aforementioned (1) to (14), wherein the polar solvent used in step (6) is a nitrile solvent.

(16) The production method of any one of the aforementioned (1) to (15), further comprising the following step (5) after step (4) and before step (6):
(5) neutralizing the reaction solution comprising the oligonucleotide (e) by adding a base.

(17) The production method of the aforementioned (16), wherein the base used in step (5) is at least one selected from pyridine, 2,4,6-trimethylpyridine, benzimidazole, 1,2,4-triazole, N-phenylimidazole, 2-amino-4,6-dimethylpyrimidine, 1,10-phenanthrolin, imidazole, N-methylimidazole, 2-chlorobenzimidazole, 2-bromobenzimidazole, 2-methylimidazole, 2-phenylbenzimidazole, N-phenylbenzimidazole and 5-nitrobenzimidazole.

(18) The production method of any one of the aforementioned (1) to (17), further comprising the following step (7) after step (6):

(7) removing all protecting groups of the obtained oligonucleotide and isolating an unprotected oligonucleotide.

(19) The production method of any one of the aforementioned (1) to (18), wherein the reaction to remove the temporary protecting group in step (4) is performed in the presence of a cation scavenger or a cation scavenger is added to the reaction solution after the reaction to remove the temporary protecting group.

(20) The production method of the aforementioned (19), wherein the cation scavenger is at least one selected from pyrrole, 2-methylpyrrole, 3-methylpyrrole, 2,3-dimethylpyrrole, 2,4-dimethylpyrrole, indole, 3-methylindole, 4-methylindole, 5-methylindole, 6-methylindole, 7-methylindole, 5,6-dimethylindole, 6,7-dimethylindole, 2-methylfuran, 2,3-dimethylfuran, 2-methyl-3-(methylthio) furan and menthofuran.

(21) A method for producing an oligonucleotide, comprising the following steps (1'), (3'), (4') and (6'):

(1') condensing, in a non-polar solvent, a nucleoside, nucleotide or oligonucleotide (b') wherein a 5'-hydroxy group is phosphoramidited, a 3'-hydroxy group or 3'-amino group is protected by a temporary protecting group removable under acidic conditions, and other groups are optionally protected by a protecting group selected from protecting groups unremovable under acidic conditions but removable under basic conditions and protecting groups used for nucleic acid synthesis, and a nucleoside, nucleotide or oligonucleotide (a') wherein a 3'-hydroxy group or 3'-amino group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are optionally protected by a protecting group used for nucleic acid synthesis, or a substituted nucleotide or oligonucleotide ($\alpha'$) wherein a 3'-hydroxy group or 3'-amino group is not protected, one hydroxy group of a 5'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis by adding the nucleoside, nucleotide or oligonucleotide (b') to a reaction solution comprising the nucleoside, nucleotide or oligonucleotide (a') or the substituted nucleotide or oligonucleotide ($\alpha'$) to give a reaction solution comprising a phosphite triester product (c') wherein the 3'-hydroxy group or 3'-amino group is protected by the temporary protecting group removable under acidic conditions;

(3') oxidizing or sulfurizing the phosphite triester product (c') by adding an oxidant or a sulfurizing agent to the reaction solution comprising the phosphite triester product (c') to give a reaction solution comprising an oligonucleotide (d') wherein the 3'-hydroxy group or 3'-amino group is protected by the temporary protecting group removable under acidic conditions;

(4') removing the temporary protecting group of the 3'-hydroxy group or 3'-amino group by adding an acid to the reaction solution after the oxidation or sulfurization to give a reaction solution comprising an oligonucleotide (e') wherein the 3'-hydroxy group or 3'-amino group is not protected; and (6') adding a polar solvent to the reaction solution comprising the oligonucleotide (e') and purifying the oligonucleotide (e') by solid-liquid separation or extraction.

(22) The production method of the aforementioned (21), wherein a nucleoside, nucleotide or oligonucleotide (a') wherein a 3'-hydroxy group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are optionally protected by a protecting group used for nucleic acid synthesis, or a substituted nucleotide or oligonucleotide ($\alpha'$) wherein a 3'-hydroxy group is not protected, one hydroxy group of a 5'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis, and a nucleoside, nucleotide or oligonucleotide (b') wherein a 5'-hydroxy group is phosphoramidited, a 3'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are used in step (1').

(23) The production method of the aforementioned (21), wherein a substituted nucleotide or oligonucleotide ($\alpha'$) wherein a 3'-hydroxy group is not protected, one hydroxy group of a 5'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis, and a nucleoside or oligonucleotide (b') wherein a 5'-hydroxy group is phosphoramidited, a 3'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are used in step (1').

(24) The production method of the aforementioned (21), wherein a nucleoside or oligonucleotide (a') wherein a 3'-hydroxy group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are optionally protected by a protecting group used for nucleic acid synthesis, and a nucleoside or oligonucleotide (b') wherein a 5'-hydroxy group is phosphoramidited, a 3'-hydroxy group is protected by a temporary protecting group removable under acidic conditions, and other groups are optionally protected by a protecting group used for nucleic acid synthesis are used in step (1').

(25) The production method of any one of the aforementioned (21) to (24), further comprising the following step (2') after step (1') and before step (3'):

(2') adding a quencher to the reaction solution after condensation.

(26) The production method of the aforementioned [25], wherein the quencher used in step (2') is at least one selected from alcohols, phenols and amines.

(27) The production method of any one of the aforementioned (21) to (26), wherein a mixture of a carboxylic acid and an organic base, an inorganic acid or an amine is added to the reaction solution after step (1') and before step (4'), and 5-[(N,N-dimethylaminomethylidene)amino]-3H-1,2,4-dithiazole-3-thione is added to the reaction solution as a sulfurizing agent in step (3').

(28) The production method of the aforementioned (27), wherein an amount of a basic nitrogen atom of the organic base is 1 to 2 mol per 1 mol of carboxy group of the carboxylic acid.

(29) The production method of any one of the aforementioned (21) to (26), wherein the sulfurizing agent used in step (3') is at least one selected from 3H-1,2-benzodithiol-3-one-1,1-dioxide, 3H-1,2-benzodithiol-3-one, phenylacetyl disulfide, tetraethylthiuram disulfide, dipentamethylenethiuram tetrasulfide, phenyl-3H-1,2,4-dithiazol-3-one, 3-amino-1,2,4-dithiazole-5-thione and sulfur.

(30) The production method of any one of the aforementioned (21) to (26), wherein the oxidant used in step (3') is at least one selected from iodine, (1S)-(+)-(10-camphanylsulfonyl)oxaziridine, tert-butyl hydroperoxide, 2-butanone peroxide, 1,1-dihydroperoxycyclododecane, bis(trimethylsilyl)peroxide and m-chloroperbenzoic acid.

(31) The production method of any one of the aforementioned (21) to (30), wherein the temporary protecting group of hydroxy group is a dimethoxytrityl group or a monomethoxytrityl group.

(32) The production method of any one of the aforementioned (21) to (31), wherein the non-polar solvent is at least one selected from a halogenated solvent, an aromatic solvent, an ester solvent and an aliphatic solvent.

(33) The production method of any one of the aforementioned (21) to (32), wherein the acid used in step (4') is at least one selected from trifluoroacetic acid, dichloroacetic acid, trifluoromethanesulfonic acid, trichloroacetic acid, methanesulfonic acid, hydrochloric acid, acetic acid and p-toluenesulfonic acid.

(34) The production method of any one of the aforementioned (21) to (33), wherein the protecting group unremovable under acidic conditions but removable under basic conditions has a linear aliphatic hydrocarbon group having a carbon number of not less than 10, or an organic group having at least one aliphatic hydrocarbon group having one or more branched chains and having a total carbon number of not less than 14 and not more than 300.

(35) The production method of any one of the aforementioned (21) to (34), wherein step (6') comprises adding a polar solvent to the reaction solution comprising the oligonucleotide (e') and purifying the oligonucleotide (e') by solid-liquid separation.

(36) The production method of any one of the aforementioned (21) to (35), wherein the polar solvent used in step (6') is a nitrile solvent.

(37) The production method of any one of the aforementioned (21) to (36), further comprising the following step (5') after step (4') and before step (6'):

(5') neutralizing the reaction solution comprising the oligonucleotide (e) by adding a base.

(38) The production method of the aforementioned (37), wherein the base used in step (5') is at least one selected from pyridine, 2,4,6-trimethylpyridine, benzimidazole, 1,2,4-triazole, N-phenylimidazole, 2-amino-4,6-dimethylpyrimidine, 1,10-phenanthrolin, imidazole, N-methylimidazole, 2-chlorobenzimidazole, 2-bromobenzimidazole, 2-methylimidazole, 2-phenylbenzimidazole, N-phenylbenzimidazole and 5-nitrobenzimidazole.

(39) The production method of any one of the aforementioned (21) to (38), further comprising the following step (7') after step (6'):

(7') removing all protecting groups of the obtained oligonucleotide and isolating an unprotected oligonucleotide.

(40) The production method of any one of the aforementioned (21) to (39), wherein the reaction to remove the temporary protecting group in step (4') is performed in the presence of a cation scavenger or a cation scavenger is added to the reaction solution after the reaction to remove the temporary protecting group.

(41) The production method of the aforementioned (40), wherein the cation scavenger is at least one selected from pyrrole, 2-methylpyrrole, 3-methylpyrrole, 2,3-dimethylpyrrole, 2,4-dimethylpyrrole, indole, 3-methylindole, 4-methylindole, 5-methylindole, 6-methylindole, 7-methylindole, 5,6-dimethylindole, 6,7-dimethylindole, 2-methylfuran, 2,3-dimethylfuran, 2-methyl-3-(methylthio)furan and menthofuran.

(42) A nucleoside or oligonucleotide represented by the formula (a-II):

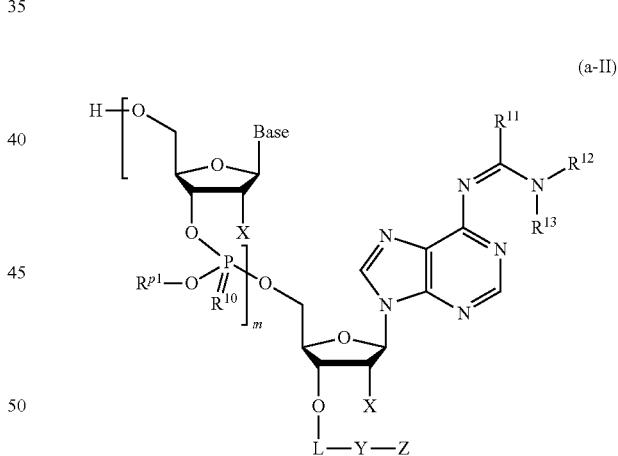

(a-II)

wherein
m is an integer of not less than 0;
Base in the number of m are each independently an optionally protected nucleic acid base;
X in the number of m+1 are each independently a hydrogen atom, a halogen atom, an optionally protected hydroxy group, or a divalent organic group bonded to a 2-position carbon atom and a 4-position carbon atom;
$R^{10}$ in the number of m are each independently an oxygen atom or a sulfur atom;
$R^{p1}$ in the number of m are each independently a protecting group of phosphoric acid group;
L is a single bond, or a group represented by the formula (a1) or (a1'):

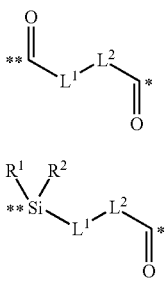

(a1)

(a1')

wherein
* indicates the bonding position to Y;
** is the bonding position to an oxygen atom;
$R^1$ and $R^2$ are each independently a $C_{1-22}$ hydrocarbon group;
$L^1$ is an optionally substituted divalent $C_{1-22}$ hydrocarbon group;
$L^2$ is a single bond or a group represented by *C(=O)N($R^3$)—$R^4$—N($R^5$) wherein * is the bonding position to L, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
Y is a single bond, an oxygen atom or NR wherein R is a hydrogen atom, an alkyl group or an aralkyl group; and
Z is a group represented by the formula (a2), the formula (a2') or the formula (a2"):

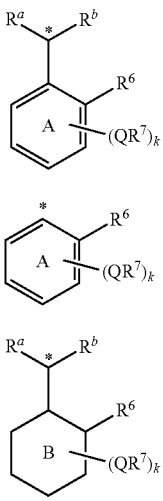

(a2)

(a2')

(a2")

wherein
* indicates a bonding position;
$R^6$ is a hydrogen atom, or when $R^b$ is a group represented by the following formula (a3), $R^6$ of ring A or ring B optionally shows, together with $R^8$, a single bond or —O— to form, together with ring A or ring B and ring C, a fused ring;
k is an integer of 1-4;
Q in the number of k are each independently —O—, —C(=O)—, —C(=O)O—, —OC(=O)—, —C(=O)NH— or —NHC(=O)—;

$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
ring A and ring B, each independently, optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;
$R_a$ is a hydrogen atom; and
$R_b$ is a hydrogen atom, or a group represented by the formula (a3):

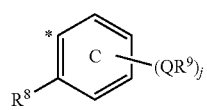

(a3)

wherein
* indicates a bonding position;
j is an integer of 0 to 4;
Q in the number of j are each independently as defined above;
$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
$R^8$ is a hydrogen atom, or optionally shows, together with $R^6$ of ring A or ring B, a single bond or —O— to form, together with ring A or ring B and ring C, a fused ring; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group, and
$R^{11}$ is a methyl group, $R^{12}$ and $R^{13}$ are each independently a $C_{1-5}$ alkyl group, or $R^{11}$ and $R^{12}$ are optionally joined to form, together with the carbon atom and nitrogen atom bonded thereto, a 5-membered or 6-membered nitrogen-containing hydrocarbon ring.

(43) The nucleoside or oligonucleotide of the aforementioned (42), wherein $R^{p1}$ is a group represented by —CH$_2$CH$_2$WG wherein WG is an electron-withdrawing group.

(44) The nucleoside or oligonucleotide of the aforementioned (42) or (43), wherein $R^{11}$ is a methyl group, and $R^{12}$ and $R^{13}$ are each independently a $C_{1-5}$ alkyl group.

(45) The nucleoside of any one of the aforementioned (42) to (44), wherein m is 0.

(46) A nucleoside or oligonucleotide represented by the formula (a-IV):

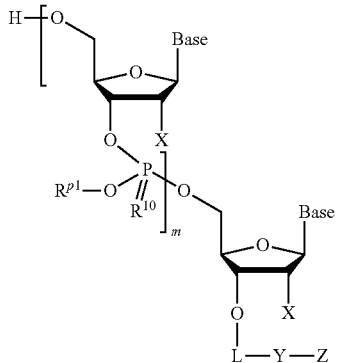

(a-IV)

wherein m is an integer of not less than 0;

Base in the number of m+1 are each independently an optionally protected nucleic acid base;

X in the number of m+1 are each independently a hydrogen atom, a halogen atom, an optionally protected hydroxy group, or a divalent organic group bonded to a 2-position carbon atom and a 4-position carbon atom;

$R^{10}$ in the number of m are each independently an oxygen atom or a sulfur atom;

$R^{p1}$ in the number of m are each independently a protecting group of phosphoric acid group;

L is a single bond, or a group represented by the formula (a1) or (a1'):

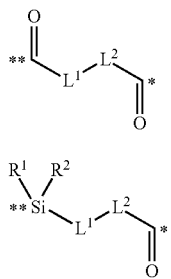

(a1)

(a1')

wherein

* indicates the bonding position to Y;
** is the bonding position to an oxygen atom;

$R^1$ and $R^2$ are each independently a $C_{1-22}$ hydrocarbon group;

$L^1$ is an optionally substituted divalent $C_{1-22}$ hydrocarbon group;

$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;

Y is a single bond, an oxygen atom or NR wherein R is a hydrogen atom, an alkyl group or an aralkyl group; and Z is a group represented by the formula (a2″):

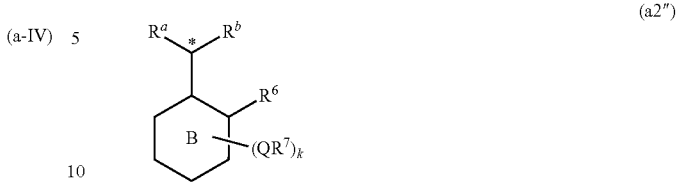

(a2″)

wherein

* indicates a bonding position;

$R^6$ is a hydrogen atom, or when $R^b$ is a group represented by the following formula (a3), it optionally shows, together with $R^8$, a single bond or —O— to form, together with ring B and ring C, a fused ring;

k is an integer of 1-4;

Q in the number of k are each independently —O—, —C(=O)—, —C(=O)O—, —OC(=O)—, —C(=O)NH— or —NHC(=O)—;

$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;

ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and $R_b$ is a hydrogen atom, or a group represented by the formula (a3):

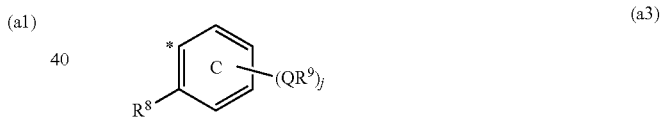

(a3)

wherein

* indicates a bonding position;

j is an integer of 0 to 4;

Q in the number of j are each independently as defined above;

$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;

$R^8$ is a hydrogen atom, or optionally shows, together with $R^6$, a single bond or —O— to form, together with ring B and ring C, a fused ring; and ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or $R^a$ and $R^b$ are joined to form an oxo group.

(47) The nucleoside or oligonucleotide of the aforementioned (46), wherein $R^{p1}$ is a group represented by —$CH_2CH_2WG$ wherein WG is an electron-withdrawing group.

(48) The nucleoside of the aforementioned (46) or (47), wherein m is 0.

(49) A nucleotide or oligonucleotide represented by the formula (I):

$$R^{n1} - \left[ O - \begin{array}{c} \text{Base} \\ \text{(sugar)} \\ O - P(=R^{10})(OR^{p1}) - O \end{array} \right]_m - O - \begin{array}{c} \text{Base} \\ \text{(sugar)} \\ O - R^{n2} \end{array}$$ (I)

wherein
m is an integer of not less than 0;
Base in the number of m+1 are each independently an optionally protected nucleic acid base;
X in the number of m+1 are each independently a hydrogen atom, a halogen atom, an optionally protected hydroxy group, or a divalent organic group bonded to a 2-position carbon atom and a 4-position carbon atom;
$R^{10}$ in the number of m are each independently an oxygen atom or a sulfur atom;
$R^{p1}$ in the number of m are each independently a protecting group of phosphoric acid group;
one of $R^{n1}$ and $R^{n2}$ is a hydrogen atom, and the other is a group represented by the formula (II):

$$* - P(=R^{10})(O - R^{p1}) - O - L^{n1} - O - L - Y - Z$$ (II)

{wherein,
* indicates a bonding position;
$R^{10}$ is an oxygen atom or a sulfur atom;
$R^{p1}$ is a protecting group of phosphoric acid group;
$L^{n1}$ is an organic group;
L is a single bond, or a group represented by the formula (a1) or (a1'):

$$** - C(=O) - L^1 - L^2 - *$$ (a1)

$$** - Si(R^1)(R^2) - L^1 - L^2 - *$$ (a1')

wherein
* indicates the bonding position to Y;
** is the bonding position to an oxygen atom;
$R^1$ and $R^2$ are each independently a $C_{1-22}$ hydrocarbon group;
$L^1$ is an optionally substituted divalent $C_{1-22}$ hydrocarbon group;
$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
Y is a single bond, an oxygen atom or NR wherein R is a hydrogen atom, an alkyl group or an aralkyl group; and
Z is a group represented by the formula (a2), the formula (a2') or the formula (a2"):

$$\begin{array}{c} R^a \quad R^b \\ * \\ \text{(ring A, benzene)} - R^6 \\ - (QR^7)_k \end{array}$$ (a2)

$$\begin{array}{c} * \\ \text{(ring A, benzene)} - R^6 \\ - (QR^7)_k \end{array}$$ (a2')

$$\begin{array}{c} R^a \quad R^b \\ * \\ \text{(ring B, cyclohexane)} - R^6 \\ - (QR^7)_k \end{array}$$ (a2")

wherein
* indicates a bonding position;
$R^6$ is a hydrogen atom, or when $R^b$ is a group represented by the following formula (a3), $R^6$ of ring A or ring B optionally shows, together with $R^8$, a single bond or —O— to form, together with ring A or ring B and ring C, a fused ring;
k is an integer of 1-4;
Q in the number of k are each independently —O—, —C(=O)—, —C(=O)O—, —OC(=O)—, —C(=O)NH— or —NHC(=O)—;
$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
ring A and ring B each independently has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and
$R_b$ is a hydrogen atom, or a group represented by the formula (a3):

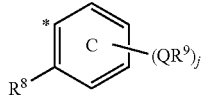

(a3)

wherein
* indicates a bonding position;
j is an integer of 0 to 4;
Q in the number of j are each independently as defined above;
$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
$R^8$ is a hydrogen atom, or optionally shows, together with $R^6$ of ring A or ring B, a single bond or —O— to form, together with ring A or ring B and ring C, a fused ring; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group.

(50) The nucleotide or oligonucleotide of the aforementioned (49), wherein $R^{n1}$ is a group represented by the formula (II), and $R^{n2}$ is a hydrogen atom.

(51) The nucleotide or oligonucleotide of the aforementioned (49) or (50), wherein $L^{n1}$ is an ethylene group.

(52) The nucleotide of any one of the aforementioned (49) to (51), wherein m is 0.

Effect of the Invention

According to the production method of the oligonucleotide of the present invention, condensation can be performed efficiently.

DETAILED DESCRIPTION OF THE PREFERRED EMBODIMENTS

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "nucleoside" to be the constituent unit of oligonucleotide means a compound wherein a nucleic acid base is bonded to the 1'-position of a sugar (e.g., 2-deoxyribose or ribose, or 2-deoxyribose or ribose wherein 2-position carbon atom and 4-position carbon atom are bonded by a divalent organic group, or the like) by N-glycosidation.

In the present specification, the "sugar" also encompasses an amino sugar wherein a hydroxy group is replaced by an amino group, and ribose wherein a 2-hydroxy group is replaced by a halogen atom.

Examples of the 2-deoxyribose or ribose wherein 2-position carbon atom and 4-position carbon atom are bonded by a divalent organic group include the following compounds.

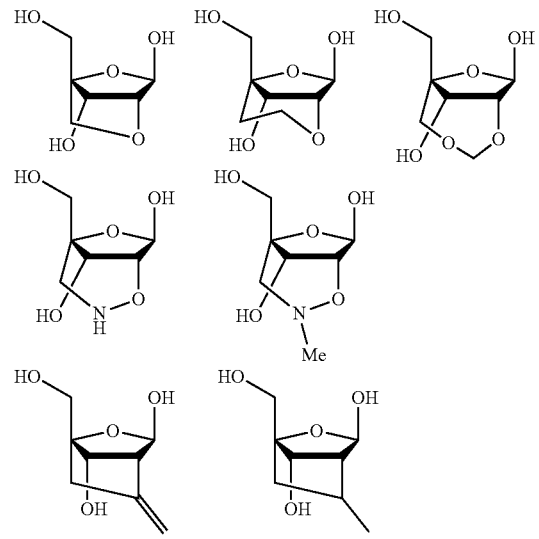

Examples of the amino sugar include 2-deoxyribose wherein 3-hydroxy group is replaced by amino group, ribose wherein 3-hydroxy group is replaced by amino group, and ribose wherein 3-hydroxy group is replaced by amino group and 2-hydroxy group is replaced by halogen, shown below (in the following formulas, $X^s$ is a halogen atom).

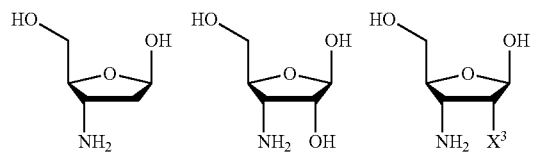

In the present specification, the "phosphoric acid group" encompasses not only —O—P(O) (OH)$_2$ but also a group wherein oxygen atom is replaced by sulfur atom or NH (e.g., —O—P(S) (OH)$_2$, —NH—P(O) (OH)$_2$, —NH—F(S) (OH)$_2$). In addition, a group wherein hydroxy group (—OH) in phosphoric acid group is replaced by —$OR^P$ wherein $R^P$ is an organic group such as a protecting group of phosphoric acid group or the like (e.g., protected phosphoric acid group) is also encompassed in the "phosphoric acid group".

In the present specification, the "nucleotide" means a compound wherein phosphoric acid group is bonded to nucleoside. Examples of the nucleotide wherein 3'-hydroxy group or 5'-hydroxy group is replaced by phosphoric acid group include the compounds shown by the following formulas (in the following formulas, $R^{m1}$ and $R^{m2}$ are each independently a hydrogen atom or an organic group (excluding nucleoside residue) and $X^m$ is a hydrogen atom, hydroxy group or halogen atom.

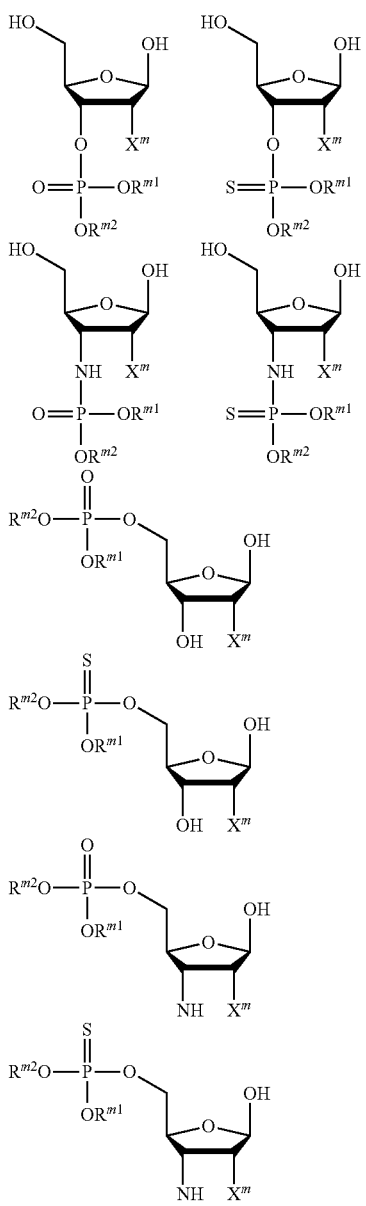

In the present specification, the "oligonucleotide" means a compound wherein one or more nucleotides are bonded to nucleoside. The "oligonucleotide" also encompasses phosphorothioate-type oligonucleotide wherein oxygen atom of phosphoric acid group is replaced by sulfur atom, oligonucleotide wherein —O— of phosphoric acid group is replaced by —NH—, and oligonucleotide wherein hydroxy group (—OH) in phosphoric acid group is replaced by —OR$^p$ wherein R$^p$ is an organic group. While the number of nucleosides in the oligonucleotide of the present invention is not particularly limited, it is preferably 3 to 50, more preferably 5 to 30.

In the present specification, the "3'-amino group" means an amino group bonded to the 3'-position carbon atom of nucleoside, nucleotide or oligonucleotide.

In the present specification, the "5'-amino group" means an amino group bonded to the 5'-position carbon atom of nucleoside, nucleotide or oligonucleotide.

In the present specification, the "3'-phosphoric acid group" means a phosphoric acid group bonded to the 3'-position carbon atom of nucleotide or oligonucleotide.

In the present specification, the "5'-phosphoric acid group" means a phosphoric acid group bonded to the 5'-position carbon atom of nucleotide or oligonucleotide.

In the present specification, the "nucleic acid base" is not particularly limited as long as it can be used for the synthesis of nucleic acid and includes, for example, pyrimidine bases such as cytosyl group, uracil group, thyminyl group and the like, and purine bases such as adenyl group, guanyl group and the like can be mentioned. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the 5'-position of the nucleotide is preferable.

The "amino-protecting group" is not particularly limited, and examples thereof include the protecting groups described in Greene's PROTECTIVE GROUPS IN ORGANIC SYNTHESIS, 4th edition, Wiley-Interscience, 2006, which is incorporated herein by reference in its entirety and the like. Specific examples of the protecting group include, pivaloyl group, pivaloyloxymethyl group, acetyl group, trifluoroacetyl group, phenoxyacetyl group, 4-isopropylphenoxyacetyl group, 4-tert-butylphenoxyacetyl group, benzoyl group, isobutyryl group, (2-hexyl)decanoyl group, dimethylformamidinyl group, 1-(dimethylamino)ethylidene group, 9-fluorenylmethyloxycarbonyl group. Among them, acetyl group, phenoxyacetyl group, 4-isopropylphenoxyacetyl group, benzoyl group, isobutyryl group, (2-hexyl)decanoyl group, dimethylformamidinyl group, and 1-(dimethylamino)ethylidene group is preferable.

The carbonyl group of the nucleic acid base is also optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not need to be particularly introduced.

In addition to the above-mentioned groups, a modified nucleic acid base (e.g., 8-bromoadenyl group, 8-bromoguanyl group, 5-bromocytosyl group, 5-iodocytosyl group, 5-bromouracil group, 5-iodouracil group, 5-fluorouracil group, 5-methylcytosyl group, 8-oxoguanyl group, hypoxanthinyl group etc.), which is a nucleic acid base substituted by any 1 to 3 substituents (e.g., halogen atom, alkyl group, aralkyl group, alkoxy group, acyl group, alkoxyalkyl group, hydroxy group, amino group, monoalkylamino, dialkylamino, carboxy, cyano, nitro etc.) at any position(s), are also encompassed in the "nucleic acid base".

In the present specification, the "halogen atom" means a fluorine atom, a chlorine atom, a bromine atom or iodine atom.

In the present specification, the "alkyl (group)" may be any of a linear and a branched chain. As the "alkyl (group)", an alkyl group having one or more carbon number can be mentioned. When the carbon number is not particularly limited, it is preferably a $C_{1-10}$ alkyl group, more preferably a $C_{1-6}$ alkyl group, further preferably $C_{1-5}$ alkyl group. When the carbon number is not particularly limited, specific preferable examples include methyl, ethyl, propyl, isopropyl, butyl, isobutyl, sec-butyl, tert-butyl, pentyl, hexyl and the like, and methyl and ethyl are particularly preferable.

In the present specification, the "$C_{a-b}$" means a carbon number of not less than a and not more than b (a, b are integers).

In the present specification, as the "aralkyl (group)", a $C_{7-20}$ aralkyl group can be mentioned, and a $C_{7-16}$ aralkyl group ($C_{6-10}$ aryl-$C_{1-6}$ alkyl group) is preferable. Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, the "alkoxy (group)" may be any of a linear and a branched chain. As the "alkoxy (group)", an alkoxy group having one or more carbon atoms can be mentioned. When the carbon number is not particularly limited, it is preferably a $C_{1-10}$ alkoxy group, more preferably a $C_{1-6}$ alkoxy group. When the carbon number is not particularly limited, specific preferable examples include methoxy, ethoxy, propoxy, isopropoxy, butoxy, isobutoxy, sec-butoxy, tert-butoxy, pentyloxy, hexyloxy and the like, and methoxy and ethoxy are particularly preferable.

In the present specification, the "acyl (group)" may be any of a linear and a branched chain. Examples of the "acyl (group)" include a $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, the "alkenyl (group)" may be any of a linear and a branched chain. Examples of the "alkenyl (group)" include a $C_{2-6}$ alkenyl group and the like Specific examples thereof include vinyl, 1-propenyl, allyl, isopropenyl, butenyl, isobutenyl and the like. Among them, a $C_2$-$C_4$ alkenyl group is preferable.

In the present specification, the "alkynyl (group)" may be any of a linear and a branched chain. Examples of the "alkynyl (group)" include $C_{2-6}$ alkynyl group and the like. Specific examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_3$-$C_6$ cycloalkyl group such as cyclopropyl, cyclobutyl, cyclopentyl, cyclohexyl or the like is preferable, and cyclohexyl is particularly preferable.

In the present specification, the "aryl (group)" means a monocyclic aromatic or polycyclic (fused) aromatic hydrocarbon group. Specific examples thereof include $C_{6-4}$ aryl groups such as phenyl, 1-naphthyl, 2-naphthyl, biphenylyl, 2-anthryl or the like, and the like. Among them, a $C_{6-10}$ aryl group is more preferable and phenyl is particularly preferable.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like, and specific examples thereof include monovalent groups such as alkyl group, alkenyl group, alkynyl group, cycloalkyl group, aryl group, aralkyl group and the like and divalent groups induced therefrom.

In the present specification, examples of the "$C_{6-14}$ hydrocarbon ring" include $C_{6-10}$ cycloalkane, $C_{6-10}$ cycloalkene, $C_{6-14}$ aromatic hydrocarbon ring.

Examples of the "$C_{6-10}$ cycloalkane" include cyclohexane, cycloheptane, cyclooctane.

Examples of the "$C_{6-10}$ cycloalkene" include cyclohexene, cycloheptene, cyclooctene.

Examples of the "$C_{6-14}$ aromatic hydrocarbon ring" include benzene, naphthalene.

In the present specification, the "alkylene (group)" may be any of a linear and a branched chain. As the "alkylene (group)", an alkylene group having a carbon number of one or more can be mentioned. When the range of carbon number is not particularly limited, it is preferably $C_{1-10}$ alkylene group, more preferably $C_{1-6}$ alkylene group. Specific preferable examples include methylene, ethylene, propylene, butylene, pentylene, hexylene, and methylene and ethylene are particularly preferable.

In the present specification, examples of the "linker" include —O—, —C(=O)—, —C(=O)O—, —OC(=O)—, —C(=O)NH—, —NHC(=O)—, —S—, —SO—, —SO$_2$—, —Si(R')(R")O—, —Si(R')(R")—(R', R" are each independently a hydrogen atom or a $C_{1-22}$ hydrocarbon group) and the like.

In the present specification, the "substituent" of the "optionally substituted" encompasses the aforementioned halogen atom, alkyl group, aralkyl group, alkoxy group, acyl group, alkenyl group, alkynyl group, cycloalkyl group, aryl group, as well as hydroxy group, nitro group, cyano group, guanidyl group, carboxy group, alkoxycarbonyl group (the alkoxy moiety is the same as that in the aforementioned alkoxy group), sulfo group, phospho group, alkylthio group (the alkyl moiety is the same as that in the aforementioned alkyl group), alkylsulfinyl group (the alkyl moiety is the same as that in the aforementioned alkyl group), alkylsulfonyl group (the alkyl moiety is the same as that in the aforementioned alkyl group), amino group, monoalkylamino group (the alkyl moiety is the same as that in the aforementioned alkyl group), dialkylamino group (the alkyl moiety is the same as that in the aforementioned alkyl group), oxo group and the like.

Production Method of Oligonucleotide

The production method of the present invention encompasses both an embodiment in which oligonucleotide chain is elongated in the direction of from the 3'-terminal to the 5'-terminal (hereinafter sometimes to be abbreviated as "3'-5' synthesis") and an embodiment in which oligonucleotide chain is elongated in the direction of from the 5'-terminal to the 3'-terminal (hereinafter sometimes to be abbreviated as "5'-3' synthesis"). The production method of the present invention to involving 3'-5' synthesis is explained below.

3'-5' Synthesis

The production method of the present invention involving 3'-5' synthesis includes the following steps (1), (3), (4) and (6). The production method may further contain, where necessary, the following steps (2), (5) and (7).

(1) condensing, in a non-polar solvent, a nucleoside, nucleotide or oligonucleotide (b) wherein a 3'-hydroxy group or 3'-amino group is phosphoramidited, a 5'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis, and a nucleoside, nucleotide or oligonucleotide (a) wherein a 5'-hydroxy group is not protected, at least one group selected from an amino group and an imino group of a nucleic acid base, a 2'-hydroxy group, a 3'-hydroxy group and a 3'-amino group of a ribose residue, and a 3'-hydroxy group and a 3'-amino group of a deoxyribose residue is protected by a protecting group unremovable under acidic conditions but removable under basic conditions, and other groups are optionally protected by a protecting group used for nucleic acid synthesis, or a substituted nucleotide or oligonucleotide (α) wherein a 5'-hydroxy group is not protected, one hydroxy group of a 3'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis
by adding the nucleoside, nucleotide or oligonucleotide (b) to a reaction solution comprising the nucleoside, nucleotide or oligonucleotide (a) or the substituted nucleotide or oligonucleotide (α) to give a reaction solution comprising a phosphite triester product (c) wherein the 5'-hydroxy group is protected by the temporary protecting group removable under acidic conditions;

(2) adding, where necessary, a quencher to the reaction solution after condensation;

(3) oxidizing or sulfurizing the phosphite triester product (c) by adding an oxidant or a sulfurizing agent to the reaction solution comprising the phosphite triester product (c) to give a reaction solution comprising an oligonucleotide (d) wherein the 5'-hydroxy group is protected by the temporary protecting group removable under acidic conditions;

(4) removing the temporary protecting group of the 5'-hydroxy group by adding an acid to the reaction solution after the oxidation or sulfurization to give a reaction solution comprising an oligonucleotide (e) wherein the 5'-hydroxy group is not protected; and (5) neutralizing, where necessary, the reaction solution comprising the oligonucleotide (e) by adding a base;

(6) adding a polar solvent to the reaction solution comprising the oligonucleotide (e) and purifying the oligonucleotide (e) by solid-liquid separation or extraction; and (7) removing, where necessary, all protecting groups of the obtained oligonucleotide and isolating an unprotected oligonucleotide.

The oligonucleotide chain can be elongated by repeating the cycle of steps (1), (3), (4) and (6) (preferably steps (1) to (6)). A production method of oligonucleotide including steps (1), (3), (4) and (6) is encompassed in the present invention.

Step (1) (Condensation)

In this step, a nucleoside, nucleotide or oligonucleotide (a) or a substituted nucleotide or oligonucleotide (α), in each of which a 5'-hydroxy group is not protected, at least one of a 3'-hydroxy group and the like is protected by a protecting group unremovable under acidic conditions but removable under basic conditions, and a nucleoside, nucleotide or oligonucleotide (b) wherein a 3'-hydroxy group or 3'-amino group is phosphoramidited, a 5'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are condensed to give a phosphite triester product (c) wherein the 5'-hydroxy group is protected by the temporary protecting group removable under acidic conditions.

In a preferable embodiment of this step, a nucleoside, nucleotide or oligonucleotide (a) wherein a 5'-hydroxy group is not protected, at least one group selected from an amino group and an imino group of a nucleic acid base, a 2'-hydroxy group and a 3'-hydroxy group of a ribose residue, and a 3'-hydroxy group of a deoxyribose residue is protected by a protecting group unremovable under acidic conditions but removable under basic conditions, and other groups are optionally protected by a protecting group used for nucleic acid synthesis, or a substituted nucleotide or oligonucleotide (α) wherein a 5'-hydroxy group is not protected, one hydroxy group of a 3'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis, and a nucleoside, nucleotide or oligonucleotide (b) wherein a 3'-hydroxy group is phosphoramidited, a 5'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are used.

The organic group for $L^{n1}$ means a group in which a hydrocarbon group or a carbon atom in a hydrocarbon group is replaced by a hetero atom. Examples of the hetero atom include oxygen atom, nitrogen atom, sulfur atom and the like. The organic group may have a substituent such as hydroxy group, amino group, oxo group (=O) or the like. The hydroxy group and the amino group that the organic group may have are preferably protected by a protecting group. The shape of the organic group may be a chain (linear or branched chain), a ring or a combination of these.

The organic group may have a group having functionality to cells. The group having functionality to cells is preferably bonded to a terminal of the main chain or a side chain of the organic group. Examples of the group having functionality to cells include "a group that improves cellular membrane permeability of a compound by improving liposolubility of the compound", "a group that improves intracellular uptake of a compound via cellular membrane receptor" and the like. Examples of the "group that improves cellular membrane permeability of a compound by improving liposolubility of the compound" include cholesterol residue, tocopherol residue and the like. Examples of the "group that improves intracellular uptake of a compound via cellular membrane receptor" include N-acetylgalactosamine residue and the like.

Specific examples of —$OL^{n1}$-OH include the following (in the following formulas, * shows the bonding position to phosphorus atom and Ac is an acetyl group).

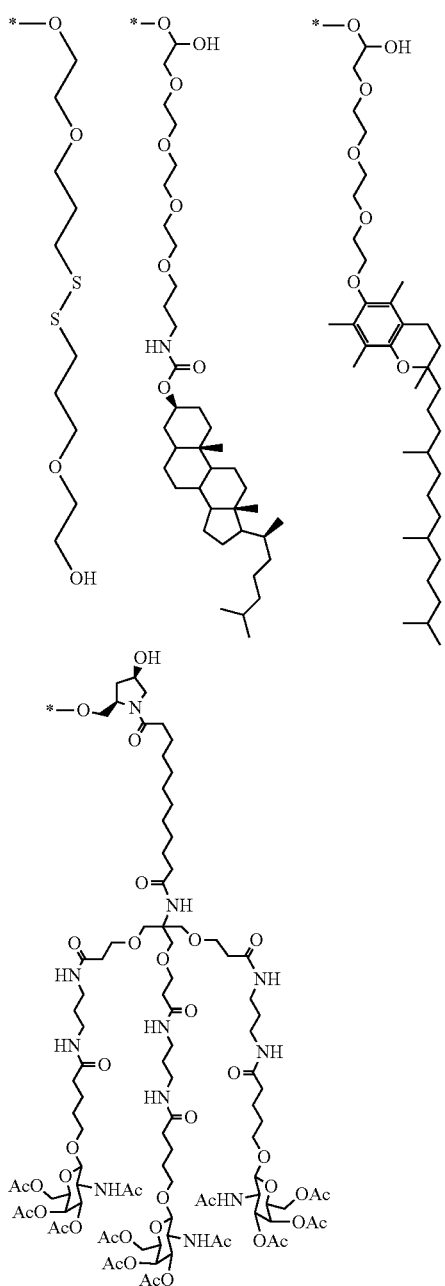

$L^{n1}$ is preferably a $C_{2-6}$ alkylene group, more preferably an ethylene group.

In a more preferable embodiment of this step, a nucleoside or oligonucleotide (a) wherein a 5'-hydroxy group is not protected, at least one group selected from an amino group and an imino group of a nucleic acid base, a 2'-hydroxy group and a 3'-hydroxy group of a ribose residue, and a 3'-hydroxy group of a deoxyribose residue is protected by a protecting group unremovable under acidic conditions but removable under basic conditions, and other groups are optionally protected by a protecting group used for nucleic acid synthesis, and a nucleoside or oligonucleotide (b) wherein a 3'-hydroxy group is phosphoramidited, a 5'-hydroxy group is protected by a temporary protecting group removable under acidic conditions, and other groups are optionally protected by a protecting group used for nucleic acid synthesis are used.

While the concentration of the nucleoside, nucleotide or oligonucleotide (a) or the substituted nucleotide or oligonucleotide (α) used in this step in the solution is not particularly limited as long as it is dissolved in a solvent, it is preferably 1 to 30 wt %.

The amino groups of the nucleoside, nucleotide or oligonucleotide (a), the substituted nucleotide or oligonucleotide (α) and the nucleoside, nucleotide or oligonucleotide (b) are preferably protected by the aforementioned protecting groups. As the protecting group, cetyl group, phenoxyacetyl group, 4-isopropylphenoxyacetyl group, benzoyl group, isobutyryl group, (2-hexyl)decanoyl group, dimethylformamidinyl group, and 1-(dimethylamino)ethylidene group are preferable. When the nucleoside, nucleotide or oligonucleotide (a) and the nucleoside, nucleotide or oligonucleotide (b) has plural amino groups, only one kind of the amino-protecting group may be used or two or more kinds thereof may be used.

In the nucleoside, nucleotide or oligonucleotide (a), at least one group selected from an amino group and an imino group of a nucleic acid base, a 2'-hydroxy group, a 3'-hydroxy group and a 3'-amino group of a ribose residue, and a 3'-hydroxy group and a 3'-amino group of a deoxyribose residue is protected by a protecting group unremovable under acidic conditions but removable under basic conditions. In the nucleoside, nucleotide or oligonucleotide (a), at least one group selected from an amino group and an imino group of a nucleic acid base, a 3'-hydroxy group of a ribose residue, and a 3'-hydroxy group of a deoxyribose residue, more preferably a 3'-hydroxy group of a ribose residue or a 3'-hydroxy group of a deoxyribose residue, is preferably protected by the aforementioned protecting group.

In the substituted nucleotide or oligonucleotide (α), the hydroxy group of —$OL^{n1}$-OH is protected by a protecting group unremovable under acidic conditions but removable under basic conditions.

The "protecting group unremovable under acidic conditions but removable under basic conditions" of the nucleoside, nucleotide or oligonucleotide (a) and the substituted nucleotide or oligonucleotide (α), and the "protecting group unremovable under acidic conditions but removable under basic conditions" that the nucleoside, nucleotide or oligonucleotide (b) optionally has are each independently and preferably a protecting group having a linear aliphatic hydrocarbon group having a carbon number of not less than 10 or an organic group having at least one aliphatic hydrocarbon group having one or more branched chains and having a total carbon number of not less than 14 and not more than 300 (hereinafter sometimes to be abbreviated as an "anchor"), to efficiently perform step (6) (solid-liquid separation or extraction).

The anchor imparts hydrophobicity to the nucleoside, nucleotide or oligonucleotide (a) and the substituted nucleotide or oligonucleotide (α) (and the nucleoside, nucleotide or oligonucleotide (b) in some cases) and improves solubility in non-polar solvents. It can also decrease solubility in polar solvents. The nucleoside, nucleotide or oligonucleotide (a) and the substituted nucleotide or oligonucleotide (α) which are each protected by such anchor can perform a condensation reaction in the liquid phase of a non-polar solvent. By adding a polar solvent to the reaction solution in the subsequent step (6), the anchor-protected oligonucleotide (e) precipitates and solid-liquid separation thereof can be performed. Alternatively, in step (6), a polar solvent is added to the reaction solution, layers are separated between the polar solvent and non-polar solvent, and the oligonucleotide (e) is transferred to the non-polar solvent, whereby the extraction thereof can be performed. As such anchor, for example, those described in JP-A-2010-275254, WO 2012/157723, and WO 2013/122236, all of which are incorporated herein by reference in their entireties, can be used.

When purification by solid-liquid separation is performed in step (6), the anchor is preferably a protecting group having a linear aliphatic hydrocarbon group having a carbon number of not less than 10. When purification by extraction is performed in step (6), the anchor is preferably a protecting group having an organic group having at least one aliphatic hydrocarbon group having one or more branched chains and having a total carbon number of not less than 14 and not more than 300.

An anchor preferable for solid-liquid separation is explained first. Examples of the anchor preferable for solid-liquid separation include a protecting group having a $C_{6-14}$ hydrocarbon ring bonded, via a linker, to a hydrocarbon group wherein a linear aliphatic hydrocarbon group having a carbon number of not less than 10 is bonded via a single bond or a linker.

The aforementioned linear aliphatic hydrocarbon group having a carbon number of not less than 10 is preferably selected from a linear $C_{10-40}$ alkyl group and a linear $C_{10-40}$ alkenyl group, more preferably a linear $C_{10-40}$ alkyl group, further preferably a linear $C_{10-30}$ alkyl group, particularly preferably a linear $C_{12-28}$ alkyl group, most preferably a linear $C_{14-26}$ alkyl group.

The aforementioned linker is preferably selected from —O—, —C(=O)—, —C(=O)O—, —OC(=O)—, —C(=O)NH—, —NHC(=O)—, —S—, —SO—, —SO$_2$—, and —Si(R')(R")O—, —Si(R')(R")— (R', R" are each independently a hydrogen atom or a $C_{1-22}$ hydrocarbon group), more preferably selected from —O—, —C(=O)—, —C(=O)O—, —OC(=O)—, —C(=O)NH— and —NHC(=O)—, further preferably —O—.

The aforementioned $C_{6-14}$ hydrocarbon ring is preferably selected from a benzene ring, a naphthalene ring and a cyclohexane ring, more preferably selected from a benzene ring and a cyclohexane ring, further preferably a benzene ring.

The anchor preferable for solid-liquid separation is preferably a protecting group having a benzene ring bonded, via —O—, to a hydrocarbon group wherein a linear $C_{10-40}$ alkyl group is bonded via a single bond or —O—.

An anchor preferable for extraction is explained now. The "branched chain" of the "organic group having at least one aliphatic hydrocarbon group having one or more branched chains and having a total carbon number of not less than 14 and not more than 300" is a linear or branched chain saturated aliphatic hydrocarbon group, and is preferably a $C_{1-6}$ alkyl group, more preferably a $C_{1-4}$ alkyl group, further preferably a methyl group or an ethyl group. The "branched chain" is optionally substituted by one or more halogen atoms.

The "aliphatic hydrocarbon group" of the "organic group having at least one aliphatic hydrocarbon group having one or more branched chains and having a total carbon number of not less than 14 and not more than 300" is a linear saturated or unsaturated aliphatic hydrocarbon group, and is a $C_{2-300}$ alkyl group (preferably $C_{3-100}$ alkyl group, more preferably $C_{3-60}$ alkyl group), a $C_{2-300}$ alkenyl group (preferably $C_{3-100}$ alkenyl group, more preferably $C_{3-60}$ alkenyl group) or a $C_{2-300}$ alkynyl group (preferably $C_{3-100}$ alkynyl group, more preferably $C_{3-60}$ alkynyl group).

The position of the "aliphatic hydrocarbon group having one or more branched chains" of the "organic group having at least one aliphatic hydrocarbon group having one or more branched chains and having a total carbon number of not less than 14 and not more than 300" is not particularly limited, and may be present on the terminal (monovalent group) or a position other than the terminal (for example, divalent group).

Examples of the "aliphatic hydrocarbon group having one or more branched chains" include branched isomers of propyl group, butyl group, pentyl group, hexyl group, heptyl group, octyl group, nonyl group, decyl group, undecyl group, dodecyl group (lauryl group), tridecyl group, myristyl group, cetyl group, stearyl group, arachyl group, behenyl group, oleyl group, linolyl group, lignoceryl group and the like, and is a monovalent group having one or more branched chains and a divalent group induced therefrom. The "aliphatic hydrocarbon group having one or more branched chains" is preferably a 3,7,11-trimethyldodecyl group, a 3,7,11,15-tetramethylhexadecyl group (hereinafter sometimes to be also referred to as 2,3-dihydrophytyl group), a 2,2,4,8,10,10-hexamethylundecan-5-yl group or the like.

When the "organic group having at least one aliphatic hydrocarbon group having one or more branched chains and having a total carbon number of not less than 14 and not more than 300" contains a plurality of "aliphatic hydrocarbon groups having one or more branched chains", they may be the same or different.

The moiety other than the "aliphatic hydrocarbon group having one or more branched chains" in the "organic group having at least one aliphatic hydrocarbon group having one or more branched chains and having a total carbon number of not less than 14 and not more than 300" can be determined freely. For example, it optionally has a moiety such as —O—, —S—, —CO—, —NH—, —COO—, —OCONH—, —CONH—, —NHCO—, and a hydrocarbon group (monovalent group or divalent group) and the like. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as alkyl group, alkenyl group, alkynyl group, cycloalkyl group, aryl group, aralkyl group and the like, and divalent groups derived therefrom are used. As the "alkyl group", a $C_{1-6}$ alkyl group is preferable, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group is preferable, for example, vinyl, 1-propenyl, allyl, isopropenyl, butenyl, isobutenyl and the like can be mentioned. As the "alkynyl group", a $C_{2-6}$ alkynyl group is preferable, for example, ethynyl, propargyl, 1-propynyl and the like can be mentioned. As the "cycloalkyl group", a $C_{3-6}$ cycloalkyl group is preferable, for example, cyclopropyl, cyclobutyl, cyclopentyl, cyclohexyl can be mentioned. As the "aryl group", a $C_{6-14}$ aryl group is preferable, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable, for example, benzyl, 1-phenylethyl, 2-phenylethyl, 1-phenylpropyl, naphthylmethyl, 1-naphthylethyl, l-naphthylpropyl and the like can be mentioned. Of these, a $C_{7-16}$ aralkyl group ($C_{6-10}$ aryl-$C_{1-6}$ alkyl group) is more preferable, and benzyl is particularly preferable. The "hydrocarbon group" is optionally substituted by a substituent selected from a halogen atom (chlorine atom, bromine atom, fluorine atom, iodine atom), an oxo group and the like.

The "total number" in the "organic group having at least one aliphatic hydrocarbon group having one or more branched chains and having a total carbon number of not less than 14 and not more than 300" is not less than 14, preferably not less than 16, more preferably not less than 18, and not more than 300, preferably not more than 200, more preferably not more than 160. The number of the branched chain in the "organic group having at least one aliphatic hydrocarbon group having one or more branched chains and having a total carbon number of not less than 14 and not more than 300" is not particularly limited, and not less than 2 is preferable, not less than 3 is more preferable, not less than 4 is more preferable, not less than 8 is more preferable, not less than 10 is further preferable. When the number of the branched chain is higher, nucleoside or oligonucleotide protected by an anchor having an organic group having at least one aliphatic hydrocarbon group having one or more branched chains and having a total carbon number of not less than 14 and not more than 300 is dissolved well in an organic solvent (particularly, non-polar solvent) even when the oligonucleotide chain is long.

As the "organic group having at least one aliphatic hydrocarbon group having one or more branched chains and having a total carbon number of not less than 14 and not more than 300", a group having the same or different divalent group represented by the formula (A):

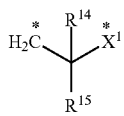

(A)

wherein
* is the bonding position to the adjacent atom;
$R^{14}$ and $R^{15}$ are each independently a hydrogen atom or a $C_{1-4}$ alkyl group; and
$X^1$ is a single bond or a $C_{1-4}$ alkylene group, provided that $R^{14}$ and $R^{15}$ are not hydrogen atoms at the same time, is preferable.

Examples of the group having the divalent group represented by the formula (A) include a group represented by any of the following formulas (B) to (D). In the definition of each symbol in the formulas (B) to (D), the carbon number, number of repeat units ($m_1$, $n_0$ to $n_2$) and the like are shown for convenience, and can be appropriately changed within the range of the above-mentioned definitions so that the total number can be not less than 14 (preferably not less than 16, more preferably not less than 18) and not more than 300 (preferably not more than 200, more preferably not more than 160). The formulas (B) to (D) are explained in order below.

The formula (B) is as described below.

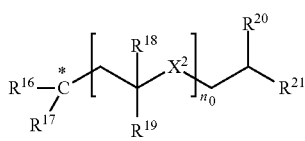

(B)

wherein
* is the bonding position to the adjacent atom;
$R^{16}$ and $R^{17}$ are hydrogen atoms or joined to show =O;
$n_0$ is an integer of 2 to 40;

$R^{18}$ and $R^{19}$ in the number of $n_0$ are each independently a hydrogen atom or a $C_{1-4}$ alkyl group;
$X^2$ in the number of $n_0$ are each independently a single bond or a $C_{1-4}$ alkylene group;
$R^{20}$ is a hydrogen atom or a $C_{1-4}$ alkyl group; and
$R^{21}$ is a $C_{1-4}$ alkyl group,
provided that $R^{18}$ and $R^{19}$ are not hydrogen atoms at the same time, and when $n_0$ is 2, $R^{20}$ is a $C_{1-4}$ alkyl group.

As the group of the formula (B), a group wherein
$R^{16}$ and $R^{17}$ are each a hydrogen atom;
$n_0$ is an integer of 2 to 40;
$R^{18}$ and $R^{19}$ in the number of $n_0$ are each independently a hydrogen atom, a methyl group or an ethyl group;
$X^2$ in the number of $n_0$ are each independently a single bond, a methylene group or an ethylene group; and
$R^{20}$ is a hydrogen atom, a methyl group or an ethyl group (provided that $R^{18}$ and $R^{19}$ are not hydrogen atoms at the same time, and when $n_0$ is 2, $R^{20}$ is methyl or an ethyl group) is preferable.

The group of the formula (B) is more preferably a branched isomer having a carbon number of 14 to 160 of myristyl group, cetyl group, stearyl group, arachyl group, behenyl group or the like, of which a 2,3-dihydrophytyl group, a 3,7,11-trimethyldodecyl group, and a 2,2,4,8,10,10-hexamethyl-5-dodecanoyl group are particularly preferable.

The formula (C) is as described below.

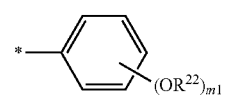

(C)

wherein
* is the bonding position to the adjacent atom;
$OR^{22}$ in the number of $m_1$ are each independently a hydroxy group substituted by a group represented by the formula (B); and
$m_1$ is an integer of 1 to 3.]

The "group represented by the formula (B)" in the formula (C) is as described above except that * therein is the bonding position to O (i.e., adjacent atom).

In the group of the formula (C), $R^{22}$ is more preferably a branched isomer group having a carbon number of 14 to 30 of myristyl group, cetyl group, stearyl group, arachyl group, behenyl group or the like, of which a 2,3-dihydrophytyl group, a 3,7,11-trimethyldodecyl group are particularly preferable.

The formula (D) is as described below.

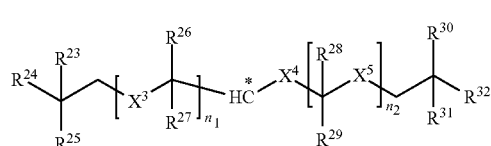

(D)

wherein
* is the bonding position to Q;
$n_1$ is an integer of 1 to 10;
$n_2$ is an integer of 1 to 10;
$R^{26}$ and $R^{27}$ in the number of $n_1$ are each independently a hydrogen atom or a $C_{1-4}$ alkyl group;

$X^3$ in the number of $n_1$ are each independently a single bond or a $C_{1-4}$ alkylene group;

$R^{28}$ and $R^{29}$ in the number of $n_2$ are each independently a hydrogen atom or a $C_{1-4}$ alkyl group;

$X^5$ in the number of $n_2$ are each independently a single bond or a $C_{1-4}$ alkylene group;

$X^4$ is a single bond or a $C_{1-4}$ alkylene group; and $R^{23}$, $R^{24}$, $R^{25}$, $R^{30}$, $R^{31}$ and $R^{32}$ are each independently a hydrogen atom or a $C_{1-4}$ alkyl group, provided that $R^{26}$ and $R^{27}$, and/or $R^{28}$ and $R^{29}$ are not hydrogen atoms at the same time, and when $n_1+n_2$ is 2, two or more of $R^{23}$, $R^{24}$ and $R^{25}$ are each independently a $C_{1-4}$ alkyl group, or two or more of $R^{30}$, $R^{31}$ and $R^{32}$ are each independently a $C_{1-4}$ alkyl group.

As the group of the formula (D), a group wherein $n_1$ is an integer of 1 to 5;

$n_2$ is an integer of 1 to 5;

$R^{26}$ and $R^{27}$ in the number of $n_1$ are each independently a hydrogen atom, a methyl group or an ethyl group;

$X^3$ in the number of $n_1$ are each independently a single bond, a methylene group or an ethylene group;

$R^{28}$ and $R^{29}$ in the number of $n_2$ are each independently a hydrogen atom, a methyl group or an ethyl group;

$X^5$ in the number of $n_2$ are each independently a single bond, a methylene group or an ethylene group;

$X^4$ is a single bond, a methylene group or an ethylene group; and $R^{23}$, $R^{24}$, $R^{25}$, $R^{30}$, $R^{31}$ and $R^{32}$ are each independently a hydrogen atom or a $C_{1-4}$ alkyl group, provided that $R^{26}$ and $R^{27}$, and/or $R^{28}$ and $R^{29}$ are not hydrogen atoms at the same time, and when $n_1+n_2$ is 2, two or more of $R^{23}$, $R^{24}$ and $R^{25}$ are each independently a $C_{1-4}$ alkyl group, or two or more of $R^{30}$, $R^{31}$ and $R^{32}$ are each independently a $C_{1-4}$ alkyl group is more preferable.

As a particularly preferable group of the formula (D), a group wherein $n_1$ is an integer of 1 to 5;

$n_2$ is an integer of 1 to 5;

$R^{26}$ and $R^{27}$ in the number of $n_1$ are each independently a hydrogen atom or a methyl group;

$X^3$ in the number of $n_1$ are each independently a single bond or a methylene group;

$R^{28}$ and $R^{29}$ in the number of $n_2$ are each independently a hydrogen atom or a methyl group;

$X^5$ in the number of $n_2$ are each independently a single bond or a methylene group;

$X^4$ is a single bond or a methylene group; and $R^{23}$, $R^{24}$, $R^{25}$, $R^{31}$, $R^{31}$ and $R^{32}$ are methyl groups, provided that $R^{26}$ and $R^{27}$, and/or $R^{28}$ and $R^{29}$ are not hydrogen atoms at the same time can be mentioned.

Specific examples of the "organic group having at least one aliphatic hydrocarbon group having one or more branched chains and having a total carbon number of not less than 14 and not more than 300" include the following groups. In each group, * shows a bonding position; in the formula, $n_3$ is an integer of not less than 3; and $n_4$ is appropriately determined such that the total number of the groups is not less than 14 and not more than 300.

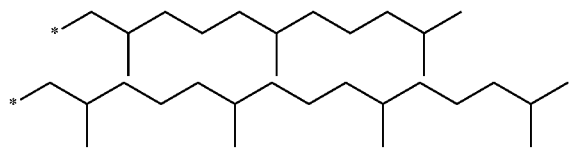

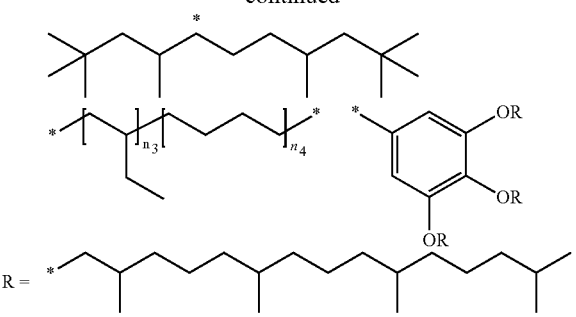

Specific preferable examples of the "organic group having at least one aliphatic hydrocarbon group having one or more branched chains and having a total carbon number of not less than 14 and not more than 300" include the following groups:

3,7,11,15-tetramethylhexadecyl group (alias: 2,3-dihydrophytyl group);

3,7,11-trimethyldodecyl group;

2,2,4,8,10,10-hexamethyl-5-dodecanoyl group;

3,4,5-tri(3',7',11',15'-tetramethylhexadecyloxy)benzyl group; and 3,5-di(3',7',11',15'-tetramethylhexadecyloxy)benzyl group.

The anchor is more preferably a group represented by the following formula (g-I) (hereinafter sometimes to be abbreviated as "anchor (g-I)").

$$**L-Y-Z \qquad (g\text{-}I)$$

wherein

** is the bonding position to the protected group;

L is a single bond, or a group represented by the formula (a1) or (a1'):

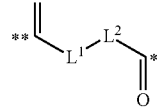
(a1)

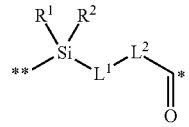
(a1')

wherein

* is the bonding position to Y;

** is as defined above;

$R^1$ and $R^2$ are each independently a $C_{1-22}$ hydrocarbon group;

$L^1$ is an optionally substituted divalent $C_{1-22}$ hydrocarbon group;

$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;

Y is a single bond, an oxygen atom or NR (wherein R is a hydrogen atom, an alkyl group or an aralkyl group); and Z is a group represented by the formula (a2), the formula (a2') or the formula (a2"):

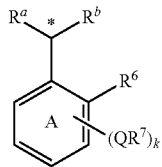

(a2)

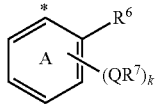

(a2')

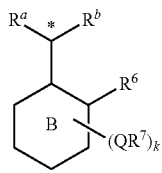

(a2")

wherein

* indicates a bonding position;

$R^6$ is a hydrogen atom, or when $R^b$ is a group represented by the following formula (a3), $R^6$ of ring A or ring B is optionally shows, together with $R^8$, a single bond or —O— to form, together with ring A or ring B and ring C, a fused ring;

k is an integer of 1 to 4;

Q in the number of k are each independently —O—, —C(=O)—, —C(=O)O—, —OC(=O)—, —C(=O)NH— or —NHC(=O)—;

$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;

ring A and ring B, each independently, optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and $R_b$ is a hydrogen atom, or a group represented by the formula (a3):

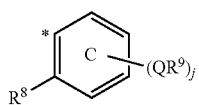

(a3)

wherein

* indicates a bonding position;

j is an integer of 0 to 4;

Q in the number of j are each independently as defined above;

$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;

$R^8$ is a hydrogen atom, or optionally shows, together with $R^6$ of ring A or ring B, a single bond or —O— to form, together with ring A or ring B and ring C, a fused ring; and ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or $R^a$ and $R^b$ are joined to form an oxo group.

The linear aliphatic hydrocarbon groups having a carbon number of not less than 10, that $R^7$ in the formula (a2), the formula (a2') and the formula (a2"), and $R^9$ in the formula (a3) have, are each independently preferably selected from linear $C_{10-40}$ alkyl group and linear $C_{10-40}$ alkenyl group, more preferably linear $C_{10-40}$ alkyl group, further preferably linear $C_{10-30}$ alkyl group, particularly preferably linear $C_{12-28}$ alkyl group, most preferably linear $C_{14-26}$ alkyl group.

The linkers that $R^7$ in the formula (a2), the formula (a2') and the formula (a2"), and $R^9$ in the formula (a3) have are each independently preferably —O—, —C(=O)—, —C(=O)O—, —OC(=O)—, —C(=O)NH— or —NHC(=O)—, more preferably —O—.

The "hydrocarbon group wherein a linear aliphatic hydrocarbon group having a carbon number of not less than 10 is bonded via a single bond or a linker" for $R^7$ in the formula (a2), the formula (a2') and the formula (a2"), and $R^9$ in the formula (a3) is preferably a linear $C_{10-40}$ alkyl group, a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—.

The "organic groups having at least one aliphatic hydrocarbon groups having one or more branched chains and having a total carbon number of not less than 14 and not more than 300", each which is one embodiment of $R^7$ in the formula (a2), the formula (a2') and the formula (a2"), and $R^9$ in the formula (a3), are each independently preferably a group having a divalent group represented by the above-mentioned formula (A), more preferably a group represented by any of the above-mentioned formulas (B)-(D), further preferably a group represented by the above-mentioned formula (B), particularly preferably a 2,3-dihydrophytyl group, a 3,7,11-trimethyldodecyl group, or a 2,2,4,8,10,10-hexamethyl-5-dodecanoyl group.

Q in the formula (a2), the formula (a2'), the formula (a2") and the formula (a3) is preferably —O—, —C(=O)NH— or —NHC(=O)—, more preferably —O—.

In the formula (g-I), a preferable embodiment of L represented by the formula (a1) is a group wherein $L^1$ is a divalent $C_{1-22}$ hydrocarbon group or $CH_2$—O-1,4-phenylene-O—$CH_2$; and $L^2$ is a single bond or a group represented by *C(=O)N($R^3$)—$R^4$—N($R^5$) wherein * is the bonding position to $L^1$, **** is the bonding position to C=O, $R^4$ is a $C_{1-6}$ alkylene group, $R^3$ and $R^5$ are each independently a hydrogen atom or an optionally substituted $C_{1-6}$ alkyl group, or $R^3$ and $R^5$ are optionally joined to form an optionally substituted $C_{1-6}$ alkylene group.

Another preferable embodiment of L represented by the formula (a1) is a group wherein $L^1$ is a divalent $C_{1-22}$ hydrocarbon group; and $L^2$ is a single bond.

Another preferable embodiment of L represented by the formula (a1) is a group wherein
$L^1$ is an ethylene group; and
$L^2$ is a group represented by *C(=O)N($R^3$)—$R^4$—N($R^5$) wherein * is the bonding position to L, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring.

Another preferable embodiment of L represented by the formula (a1) is a group wherein
$L^1$ is an ethylene group; and
$L^2$ is a group represented by *C(=O)N($R^3$)—$R^4$—N($R^5$) wherein * is the bonding position to $L^1$, **** is the bonding position to C=O, and N($R^3$)—$R^4$—N($R^5$) moiety forms a 1,4-piperazinediyl group.

Another preferable embodiment of L represented by the formula (a1) is a group wherein
$L^1$ is an ethylene group; and
$L^2$ is a group represented by *C(=O)N($R^3$)—$R^4$—N($R^5$) wherein * is the bonding position to $L^1$, **** is the bonding position to C=O, $R^4$ is a pentylene group or a hexylene group, and $R^3$ and $R^5$ are each independently a hydrogen atom or a methyl group.

Particularly preferable embodiment of L represented by the formula (a1) is a succinyl group which is easily available and economical.

In the formula (g-I), L represented by the formula (a1') is explained below.

$L^1$ in the formula (a1') is preferably a divalent $C_{6-10}$ aromatic hydrocarbon group, more preferably a phenylene group.

$L^2$ in the formula (a1') is preferably a single bond.

A preferable combination of $L^1$ and $L^2$ in the formula (a1') is a combination of a divalent $C_{6-10}$ aromatic hydrocarbon group for $L^1$ and a single bond for $L^2$. A more preferable combination of $L^1$ and $L^2$ in the formula (a1') is a combination of a phenylene group for $L^1$ and a single bond for $L^2$.

$R^1$ and $R^2$ in the formula (a1') are each independently preferably a $C_{1-22}$ alkyl group, more preferably a $C_{1-10}$ alkyl group.

A preferable embodiment of L represented by the formula (a1') is a group wherein
$R^1$ and $R^2$ are each independently a $C_{1-22}$ alkyl group;
$L^1$ is a divalent $C_6$-10 aromatic hydrocarbon group; and
$L^2$ is a single bond.

Another preferable embodiment of L represented by the formula (a1') is a group wherein
$R^1$ and $R^2$ is are each independently a $C_{1-10}$ alkyl group;
$L^1$ is a phenylene group; and
$L^2$ is a single bond.

When Y in the formula (g-I) is NR, the aforementioned R is preferably a hydrogen atom, a $C_{1-6}$ alkyl group or a $C_{7-16}$ aralkyl group, more preferably a hydrogen atom, methyl, ethyl or benzyl, further preferably a hydrogen atom. Y is preferably a single bond, an oxygen atom or NR, more preferably a single bond or an oxygen atom.

Z in the formula (g-I) is preferably a group represented by the formula (a2) or the formula (a2"), more preferably a group represented by the formula (a2"). Using an anchor having Z represented by the formula (a2") (i.e., structure of cyclohexylmethyl group), the solubility of the nucleoside, nucleotide or oligonucleotide (a) and the like in non-polar solvents can be strikingly improved as compared to an anchor having Z represented by the formula (a2) (i.e., structure of benzyl group). As a result, the production method of the present invention can be performed at a higher concentration and productivity is strikingly improved.

In the formula (a2), $R^6$ is preferably a hydrogen atom. In the formula (a2), $R^a$ and $R^b$ are each preferably a hydrogen atom, or are joined to form an oxo group.

An embodiment preferable for solid-liquid separation of Z represented by the formula (a2) is a group wherein
$R^a$ and $R^b$ are hydrogen atoms;
$R^6$ is a hydrogen atom;
k is an integer of 1 to 3;
Q in the number of k are —O—; and
$R^7$ in the number of k are each independently a linear $C_{10-40}$ alkyl group.

Another embodiment preferable for solid-liquid separation of Z represented by the formula (a2) is a group wherein
$R^a$ and $R^b$ are hydrogen atoms;
$R^6$ is a hydrogen atom;
k is an integer of 1 to 3;
Q in the number of k are —O—; and
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring A optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

Another embodiment preferable for solid-liquid separation of Z represented by the formula (a2) is a group wherein
$R^a$ is a hydrogen atom; and
$R^b$ is a group represented by the formula (a3) wherein * shows the bonding position, j is an integer of 0-3, Q in the number of j are —O—, $R^9$ in the number of j are each independently a linear $C_{10-40}$ alkyl group, $R^6$ and $R^8$ are each a hydrogen atom.

Another embodiment preferable for solid-liquid separation of Z represented by the formula (a2) is a group wherein
$R^a$ is a hydrogen atom; and
$R^b$ is a group represented by the formula (a3) wherein * shows the bonding position, j is an integer of 0 to 3, Q in the number of j are —O—, $R^9$ in the number of j are each independently a linear $C_{10-40}$ alkyl group, $R^8$ shows, together with $R^6$, a single bond or —O— to form, together with ring A and ring C, a fused ring.

Another embodiment preferable for solid-liquid separation of Z represented by the formula (a2) is a group wherein
$R^a$ and $R^b$ are joined to form an oxo group;
$R^6$ is a hydrogen atom;
k is an integer of 1 to 3;
Q in the number of k are —O—; and
$R^7$ in the number of k are each independently a linear $C_{10-40}$ alkyl group.

Another embodiment preferable for solid-liquid separation of Z represented by the formula (a2) is a group wherein
$R^a$ and $R^b$ are joined to form an oxo group;
$R^6$ is a hydrogen atom;
k is an integer of 1 to 3;
Q in the number of k are —O—; and
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring A optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

In the formula (a2"), $R^6$ is preferably a hydrogen atom. In the formula (a2"), $R^a$ and $R^b$ are each preferably a hydrogen atom, or are joined to form an oxo group.

A embodiment preferable for solid-liquid separation of Z represented by the formula (a2") is a group wherein
$R^a$ and $R^b$ are hydrogen atoms;
$R^6$ is a hydrogen atom;
k is an integer of 1 to 3;
Q in the number of k are —O—; and
$R^7$ in the number of k are each independently a linear $C_{10-40}$ alkyl group.

Another embodiment preferable for solid-liquid separation of Z represented by the formula (a2") is a group wherein
$R^a$ and $R^b$ is a hydrogen atom;
$R^6$ is a hydrogen atom;
k is an integer of 1 to 3;
Q in the number of k are —O—;
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

Another embodiment preferable for solid-liquid separation of Z represented by the formula (a2") is a group wherein
$R^a$ is a hydrogen atom;
$R^b$ is a group represented by the formula (a3) wherein * shows the bonding position, j is an integer of 0 to 3, Q in the number of j are —O—, $R^9$ in the number of j is are each independently a $C_{10-40}$ alkyl group, and $R^6$ and $R^8$ are hydrogen atoms.

Another embodiment preferable for solid-liquid separation of Z represented by the formula (a2") is a group wherein
$R^a$ is a hydrogen atom;
$R^b$ is a group represented by the formula (a3) wherein * shows the bonding position, j is an integer of 0 to 3, Q in the number of j is —O—, $R^9$ in the number of j are each independently a linear $C_{10-40}$ alkyl group, $R^8$ shows, together with $R^6$, a single bond or —O— to form, together with ring B and ring C, a fused ring.

Another embodiment preferable for solid-liquid separation of Z represented by the formula (a2") is a group wherein
$R^a$ and $R^b$ are joined to form an oxo group;
$R^6$ is a hydrogen atom;
k is an integer of 1 to 3;
Q in the number of k are —O—; and
$R^7$ in the number of k are each independently a linear $C_{10-40}$ alkyl group.

Another embodiment preferable for solid-liquid separation of Z represented by the formula (a2") is a group wherein
$R^a$ and $R^b$ are joined to form an oxo group;
$R^6$ is a hydrogen atom;
k is an integer of 1 to 3;
Q in the number of k are —O—;
$R^7$ in the number of k are each independently a benzyl group to which 1 to 3 linear $C_{10-40}$ alkyl groups are bonded via —O—, or a cyclohexylmethyl group to which 1 to 3 linear $C_{10-40}$ alkyl groups are bonded via —O—; and
ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom.

Anchor (g-I) preferable for solid-liquid separation is preferably a group wherein
L is a succinyl group, or a group represented by the formula (a1') (in the formula (a1'), $R^1$ and $R^2$ are each independently a $C_{1-10}$ alkyl group, $L^1$ is a divalent phenylene group, $L^2$ is a single bond), and
Y—Z is a 3,4,5-tris(octadecyloxy)benzyloxy group, a 3,5-bis(docosyloxy)benzyloxy group, a 3,5-bis[3',4',5'-tris(octadecyloxy)benzyloxy]benzyloxy group, a 3,4,5-tris[3',4',5'-tris(octadecyloxy)benzyloxy]benzyloxy group, a 3,4,5-tris(octadecyloxy)benzylamino group, a 2,4-bis(docosyloxy)benzylamino group, 3,5-bis(docosyloxy)benzylamino group, a bis(4-docosyloxyphenyl)methylamino group, a 4-methoxy-2-[3',4',5'-tris(octadecyloxy)benzyloxy]benzylamino group, a 4-methoxy-2-[3',4',5'-tris(octadecyloxy)cyclohexylmethyloxy]benzylamino group, a 2,4-bis(dodecyloxy)benzylamino group, a phenyl(2,3,4-tris(octadecyloxy)phenyl)methylamino group, a bis[4-(12-docosyloxydodecyloxy)phenyl]methylamino group, a 3,5-bis[3',4',5'-tris(octadecyloxy)benzyloxy]benzylamino group, a 3,4,5-tris[3',4',5'-tris(octadecyloxy)benzyloxy]benzylamino group, a 3,4,5-tris(octadecyloxy)cyclohexylmethyloxy group, a 3,5-bis(docosyloxy)cyclohexylmethyloxy group, a 3,5-bis[3',4',5'-tris(octadecyloxy)cyclohexylmethyloxy]cyclohexylmethyloxy group, a 3,4,5-tris[3',4',5'-tris(octadecyloxy)cyclohexylmethyloxy]cyclohexylmethyloxy group, a 3,4,5-tris(octadecyloxy)cyclohexylmethylamino group, a 2,4-bis(docosyloxy)cyclohexylmethylamino group, a 3,5-bis(docosyloxy)cyclohexylmethylamino group, a bis(4-docosyloxycyclohexyl)methylamino group, a 4-methoxy-2-[3',4',5'-tris(octadecyloxy)cyclohexylmethyloxy]cyclohexylmethylamino group, a 4-methoxy-2-[3',4',5'-tris(octadecyloxy)cyclohexylmethyloxy]cyclohexylmethylamino group, a 2,4-bis(dodecyloxy)cyclohexylmethylamino group, phenyl(2,3,4-tris(octadecyloxy)cyclohexyl)methylamino group, a bis[4-(12-docosyloxydodecyloxy)cyclohexyl]methylamino group, a 3,5-bis[3',4',5'-tris(octadecyloxy)cyclohexylmethyloxy]cyclohexylmethylamino group or a 3,4,5-tris[3',4',5'-tris(octadecyloxy)cyclohexylmethyloxy]cyclohexylmethylamino group, or a group wherein
L-Y is a single bond or a succinyl-1,4-piperazinediyl group, and
Z is a 3,4,5-tris(octadecyloxy)benzoyl group, a 3,5-bis(docosyloxy)benzoyl group, a 3,5-bis[3',4',5'-tris(octadecyloxy)benzyloxy]benzoyl group or a 3,4,5-tris[3',4',5'-tris(octadecyloxy)benzyloxy]benzoyl group.

Anchor (g-I) preferable for solid-liquid separation is more preferably a group wherein
L is a succinyl group, and
Y—Z is a 3,4,5-tris(octadecyloxy)benzyloxy group, a 3,5-bis(docosyloxy)benzyloxy group, a 3,5-bis[3',4',5'-tris(octadecyloxy)benzyloxy]benzyloxy group, a 3,4,5-tris[3',4',5'-tris(octadecyloxy)benzyloxy]benzyloxy group, a 3,4,5-tris(octadecyloxy)benzylamino group, a 2,4-bis(docosyloxy)benzylamino group, a 3,5-bis(docosyloxy)benzylamino group, a bis(4-docosyloxyphenyl)methylamino group, a 4-methoxy-2-[3',4',5'-tris(octadecyloxy)benzyloxy]benzylamino group, a 4-methoxy-2-[3',4',5'-tris(octadecyloxy)cyclohexylmethyloxy]benzylamino group, a 2,4-bis(dodecyloxy)benzylamino group, a phenyl(2,3,4-tris(octadecyloxy)phenyl)methylamino group, a bis[4-(12-docosyloxydodecyloxy)phenyl]methylamino group, a 3,5-bis[3',4',5'-tris(octadecyloxy)benzyloxy]benzylamino group, a 3,4,5-tris[3',4',5'-tris(octadecyloxy)benzyloxy]benzylamino group, a 3,4,5-tris(octadecyloxy)cyclohexylmethyloxy group, a 3,5-bis(docosyloxy)cyclohexylmethyloxy group, a 3,5-bis[3',4',5'-tris(octadecyloxy)cyclohexylmethyloxy]cyclohexylmethyloxy group, a 3,4,5-tris[3',4',5'-tris(octadecyloxy)cyclohexylmethyloxy]cyclohexylmethyloxy group, a 3,4,5-tris(octadecyloxy)cyclohexylmethylamino group, a 2,4-bis(docosyloxy)cyclohexylmethylamino group, a 3,5-bis(docosyloxy)cyclohexylmethylamino group, a bis(4-docosyloxycyclohexyl)methylamino group, a 4-methoxy-2-[3',4',5'-tris(octadecyloxy)cyclohexylmethyloxy]cyclohexylmethylamino group, a 4-methoxy-2-[3',4',5'-tris(octadecyloxy)cyclohexylmethyloxy]cyclohexylmethylamino group, a 2,4-bis(dodecyloxy)cyclohexylmethylamino group, phenyl(2,3,4-tris(octadecyloxy)cyclohexyl)methylamino group, a bis[4-(12-docosyloxydodecyloxy)cyclohexyl]methylamino group, a 3,5-bis[3',4',5'-tris(octadecyloxy)cyclohexylmethyloxy]cyclohexylmethylamino group or a 3,4,5-tris[3',4',5'-tris(octadecyloxy)cyclohexylmethyloxy]cyclohexylmethylamino group, or a group wherein L-Y is a single bond or a succinyl-1,4-piperazinediyl group, and Z is a 3,4,5-tris(octadecyloxy)benzoyl group, a 3,5-bis(docosyloxy)benzoyl group, a 3,5-bis[3',4',5'-tris(octadecyloxy)benzyloxy]benzoyl group or a 3,4,5-tris[3',4',5'-tris(octadecyloxy)benzyloxy]benzoyl group.

Anchor (g-I) preferable for solid-liquid separation is further preferably a group wherein L is a succinyl group, and Y—Z is a 3,4,5-tris(octadecyloxy)benzyloxy group, a 3,4,5-tris(octadecyloxy)cyclohexylmethyloxy group, a 3,5-bis(docosyloxy)cyclohexylmethyloxy group, a 3,5-bis[3',4',5'-tris(octadecyloxy)cyclohexylmethyloxy]cyclohexylmethyloxy group, a 3,4,5-tris[3',4',5'-tris(octadecyloxy)cyclohexylmethyloxy]cyclohexylmethyloxy group, a 3,4,5-tris(octadecyloxy)cyclohexylmethylamino group, a 2,4-bis(docosyloxy)cyclohexylmethylamino group, a 3,5-bis(docosyloxy)cyclohexylmethylamino group, a 4-methoxy-2-[3',4',5'-tris(octadecyloxy)cyclohexylmethyloxy]cyclohexylmethylamino group, a 4-methoxy-2-[3',4',5'-tris(octadecyloxy)cyclohexylmethyloxy]cyclohexylmethylamino group, a 2,4-bis(dodecyloxy)cyclohexylmethylamino group, a 3,5-bis[3',4',5'-tris(octadecyloxy)cyclohexylmethyloxy]cyclohexylmethylamino group or a 3,4,5-tris[3',4',5'-tris(octadecyloxy)cyclohexylmethyloxy]cyclohexylmethylamino group, or a group wherein L-Y is a single bond or a succinyl-1,4-piperazinediyl group, and Z is a 3,4,5-tris(octadecyloxy)benzoyl group.

Anchor (g-I) preferable for solid-liquid separation is particularly preferably a group wherein L is a succinyl group, and Y—Z is a 3,4,5-tris(octadecyloxy)benzyloxy group, a 3,4,5-tris(octadecyloxy)cyclohexylmethyloxy group or a phenyl(2,3,4-tris(octadecyloxy)phenyl)methylamino group, or a group wherein L-Y is a succinyl-1,4-piperazinediyl group, and Z is a 3,4,5-tris(octadecyloxy)benzoyl group.

Anchor (g-I) preferable for solid-liquid separation is most preferably a group wherein L is a succinyl group, and Y—Z is a 3,4,5-tris(octadecyloxy)benzyloxy group or a 3,4,5-tris(octadecyloxy)cyclohexylmethyloxy group, or a group wherein L-Y is a succinyl-1,4-piperazinediyl group, and Z is a 3,4,5-tris(octadecyloxy)benzoyl group.

Anchor (g-I) preferable for extraction is preferably a 2-{2,4-di(2',3'-dihydrophytyloxy)benzylaminocarbonyl}ethylcarbonyl group; a 3,5-di(2',3'-dihydrophytyloxy)benzyloxysuccinyl group; a 4-(2',3'-dihydrophytyloxy)benzyloxysuccinyl group; a 2-{1-[(2-chloro-5-(2',3'-dihydrophytyloxy)phenyl)]benzylaminocarbonyl}ethylcarbonyl group; a 3,4,5-tri(2',3'-dihydrophytyloxy)benzyloxysuccinyl group; a 2-{3,4,5-tri(2',3'-dihydrophytyloxy)benzylaminocarbonyl}ethylcarbonyl group; a 2-35 {4-(2',3'-dihydrophytyloxy)benzylaminocarbonyl}ethylcarbonyl group; a 2-{2-[3',4',5'-tri(2'',3''-dihydrophytyloxy)benzyloxy]-4-methoxybenzylaminocarbonyl}ethylcarbonyl group; a 2-{4-(2',3'-dihydrophytyloxy)-2-methoxybenzylaminocarbonyl}ethylcarbonyl group; a 4-(2',3'-dihydrophytyloxy)-2-methylbenzyloxysuccinyl group; a 2-{4-(2',3'-dihydrophytyloxy)-2-methylbenzylaminocarbonyl}ethylcarbonyl group; a 4-[2,2,4,8,10,10-hexamethyl-5-dodecanoylamino]benzyloxysuccinyl group; a 2-{4-[2,2,4,8,10,10-hexamethyl-5-dodecanoylamino]benzylaminocarbonyl}ethylcarbonyl group; a 4-(3,7,11-trimethyldodecyloxy)benzyloxysuccinyl group; a 2-{4-(3,7,11-trimethyldodecyloxy)benzylaminocarbonyl}ethylcarbonyl group; a 2-{3,5-di(2',3'-dihydrophytyloxy)benzylaminocarbonyl}ethylcarbonyl group; a 2-{1-[2,3,4-tri(2',3'-dihydrophytyloxy)phenyl]benzylaminocarbonyl} ethylcarbonyl group; a 2-{1-[4-(2',3'-dihydrophytyloxy)phenyl]-4'-(2',3'-dihydrophytyloxy)benzylaminocarbonyl}ethylcarbonyl group; a 3,4,5-tris[3,4,5-tri (2',3'-dihydrophytyloxy)benzyl]benzyloxysuccinyl group; or a 2-{3,4,5-tris[3,4,5-tri (2',3'-dihydrophytyloxy)benzyl]benzylaminocarbonyl} ethylcarbonyl group.

An alcohol compound or amine compound represented by the formula: Z—Y—H and used for forming an anchor can be produced by, for example, the following step or a step analogous thereto.

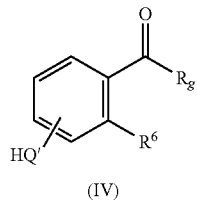

(IV)

(Q' = O, S, CO₂, NH)

↓ (a)

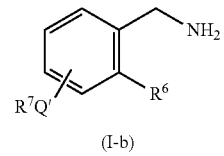

(I-b)

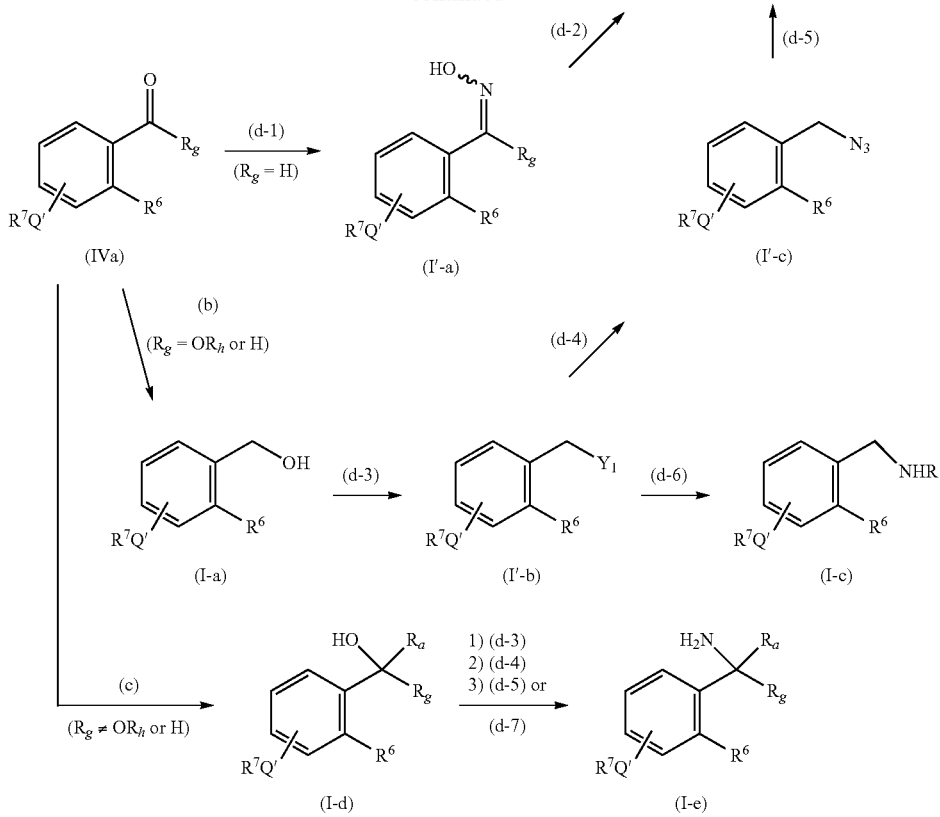

wherein Q' is —O—, —S—, —C(=O)O— or —NH—, $R_g$ is a hydrogen atom, an $OR_h$ group (wherein $R_h$ is an alkyl group such as $C_1$-6 alkyl group or the like, an aralkyl group such as benzyl group or the like, or the like) or a group represented by the formula (a3):

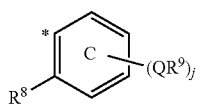

wherein each symbol is as defined above,
$Y_1$ is a leaving group such as halogen atom or the like, and other symbols are as defined above.

Step (a)

In this step, $R^7$ is introduced into Q'H (wherein Q' is —O—, —S—, —C(=O)O— or —NH—) of a compound represented by the formula (IV) (hereinafter to be abbreviated as compound (IV)) to produce a compound represented by the formula (IVa) (hereinafter to be abbreviated as compound (IVa)). When Q' is —O—, —S— or —NH—, this reaction is performed in a solvent that does not influence the reaction, in the presence or absence of a base and using a halide (chloride, bromide or iodide) corresponding to $R^7$, a carboxylic acid or acid halide corresponding to $R^7$ or an alkylsulfonyloxylation product (e.g., methanesulfonyloxylation product etc.) or arylsulfonyloxylation product (e.g., p-toluenesulfonyloxylation product etc.) corresponding to $R^7$. When Q' is —O—, this reaction can also be performed under the Mitsunobu reaction condition wherein compound (IV) and a hydroxide corresponding to $R^7$ are reacted in the presence of triphenylphosphine and diisopropyl azodicarboxylate. Furthermore, when Q' is —C(=O)O—, for example, compound (IVa) can be synthesized by reacting compound (IV) and an amine or hydroxide corresponding to $R^7$ in the presence of the below-mentioned condensing agent.

Examples of the base include alkali metal salts such as sodium carbonate, sodium hydrogen carbonate, potassium carbonate, sodium hydride, potassium hydride, potassium tert-butoxide and the like; amines such as pyridine, triethylamine, N,N-dimethylaniline, 1,8-diazabicyclo[5.4.0]-7-undecene and the like, and the like, of which sodium carbonate, potassium carbonate, sodium hydride and the like are preferable.

Examples of the solvent include aromatic hydrocarbons such as toluene, xylene and the like; ethers such as tetrahydrofuran, dioxane and the like; amides such as dimethylformamide, dimethylacetamide and the like; halogenated hydrocarbons such as chloroform, dichloromethane and the like; nitriles such as acetonitrile and the like, N-methylpyrrolidone and the like or a mixture thereof. Of these, dimethylformamide, tetrahydrofuran, toluene, N-methylpyrrolidone and the like are preferable.

The reaction temperature is preferably 50 to 150° C., more preferably 60 to 130° C. The reaction time is preferably 2 to hr, more preferably 3 to 10 hr.

Step (b)

In this step, compound (IVa) is reduced to produce a compound represented by the formula (I-a) (hereinafter to be abbreviated as compound (I-a)). This reduction reaction can be performed by a method using a reducing agent.

Examples of the reducing agent to be used for the reduction reaction include metal hydride (sodium borohydride, lithium borohydride, sodium cyanoborohydride, sodium triacetoxyborohydride, dibutylaluminum hydride, aluminum hydride, lithium aluminum hydride etc.) and the like, of which sodium borohydride, dibutylaluminum hydride and the like are preferable.

This reaction is performed in a solvent that does not influence the reaction. Examples of the solvent include alcohols such as methanol, ethanol and the like; ethers such as diethyl ether, tetrahydrofuran, dioxane and the like; aromatic hydrocarbons such as toluene, xylene and the like; or a mixture thereof, of which tetrahydrofuran, toluene and the like are preferable. The reaction temperature is preferably 0 to 100° C., more preferably 30 to 70° C. The reaction time is preferably 1 to 24 hr, more preferably 2 to 5 hr.

Step (c)

In this step, compound (IVa) (in the formula (IVa), $R_g$ is not a hydrogen atom or an $OR_h$ group) is reduced in the same manner as in the above-mentioned step (b).

Step (d-1)

In this step, compound (IVa) (in the formula (IVa), $R_g$ is a hydrogen atom) is oximated to produce a compound represented by the formula (I'-a) (hereinafter to be abbreviated as compound (I'-a)).

This oximation reaction is performed by reacting compound (IVa) and hydroxylamine acid addition salt in a solvent that does not influence the reaction in the presence of a base.

Examples of the hydroxylamine acid addition salt include mineral acid salts such as hydrochloride, sulfate, nitrate and the like, organic acid salts such as acetate, trifluoroacetate, methanesulfonate, trifluoromethanesulfonate, p-toluenesulfonate and the like, and the like, and hydrochloride is particularly preferable.

Examples of such base include alkali metal salts such as potassium hydroxide, sodium hydroxide, sodium hydrogen carbonate, potassium carbonate and the like; organic amines such as pyridine, triethylamine, diisopropylethylamine, N,N-dimethylaniline, 1,8-diazabicyclo[5.4.0]undec-7-ene and the like, and the like, of which triethylamine, diisopropylethylamine and the like are preferable.

Examples of the solvent include halogen solvents such as chloroform, dichloromethane and the like; aromatic hydrocarbons such as toluene, xylene and the like; ethers such as tetrahydrofuran, dioxane and the like; and/or mixtures thereof, of which dichloromethane, chloroform, toluene and the like are preferable. The reaction temperature is preferably 10 to 100° C., more preferably 20 to 60° C. The reaction time is preferably 0.5 to 30 hr, more preferably 2 to 20 hr.

Step (d-2)

In this step, compound (I'-a) is reduced by a catalytic hydrogenation reaction in the presence of a metal catalyst such as palladium-carbon, Raney-nickel or the like, or a reducing agent similar to one in the aforementioned step (b) such as metal hydride or the like to produce a compound represented by the formula (I-b) (hereinafter to be abbreviated as compound (I-b)).

Compound (I-b) can also be produced via step (d-3), step (d-4) and step (d-5).

Step (d-3)

In this step, compound (I-a) is halogenated using, for example, a chlorinating agent such as acetyl chloride, thionyl chloride or the like or a brominating agent such as acetyl bromide, phosphorus tribromide, diphenylphosphine/bromine or the like to produce a compound represented by the formula (I'-b) (hereinafter to be abbreviated as compound (I'-b)).

Examples of the solvent include halogenated hydrocarbons such as chloroform, dichloromethane and the like; aromatic hydrocarbons such as toluene, xylene and the like; ethers such as tetrahydrofuran, dioxane and the like; mixtures thereof, of which chloroform, tetrahydrofuran, toluene and the like are preferable. The reaction temperature is preferably 10 to 150° C., more preferably 30 to 80° C. The reaction time is preferably 0.5 to 30 hr, more preferably 2 to 20 hr.

Step (d-4)

In this step, compound (I'-b) is azidated using an azidating agent such as sodium azide or the like to produce a compound represented by the formula (I'-c) (hereinafter to be abbreviated as compound (I'-c)). This reaction is performed by reacting compound (I'-b) with an azidating agent in a solvent that does not influence the reaction.

Examples of the solvent include halogenated hydrocarbons such as chloroform, dichloromethane and the like; aromatic hydrocarbons such as toluene, xylene and the like; ethers such as tetrahydrofuran, dioxane and the like; amides such as N,N-dimethylformamide and the like; mixtures thereof, of which chloroform, N,N-dimethylformamide and the like are preferable. The reaction temperature is preferably 10 to 150° C., more preferably 20 to 100° C. The reaction time is preferably 0.5 to 30 hr, more preferably 2 to 20 hr.

Step (d-5)

In this step, compound (I'-c) is aminated to produce compound (I-b). This reaction is performed by reacting compound (I'-c) with triphenylphosphine in a solvent that does not influence the reaction in the presence of water, or by a catalytic hydrogenation reduction.

The amount of triphenylphosphine to be used is preferably 1 to 10 mol, particularly preferably 1 to 5 mol, per 1 mol of compound (I'-c). The amount of water to be used is preferably 1 to 10 mol, particularly preferably 1 to 5 mol, per 1 mol of compound (I'-c).

Examples of the solvent include aromatic hydrocarbons such as toluene, xylene and the like; ethers such as tetrahydrofuran, dioxane and the like; and mixtures thereof, of which toluene, tetrahydrofuran and the like are preferable. The reaction temperature is preferably 10 to 150° C., more preferably 20 to 100° C. The reaction time is preferably 0.5 to hr, more preferably 2 to 20 hr.

Step (d-6)

In this step, compound (I'-b) is reacted with $RNH_2$ (R are as defined above) to produce a compound represented by the formula (I-c) wherein Y is a —NHR group (hereinafter to be abbreviated as compound (I-c)). In this step, compound (I'-b) is reacted with an amine represented by R—$NH_2$ in a solvent that does not influence the reaction, where necessary, in the presence of a base such as a tertiary amine (triethylamine, diisopropylethylamine or the like) or the like.

Examples of the solvent include aromatic hydrocarbons such as toluene, xylene and the like; ethers such as tetrahydrofuran, dioxane and the like; and halogen solvents such as chloroform, dichloromethane and the like or, mixtures thereof, of which toluene, tetrahydrofuran, chloroform and the like are preferable. The reaction temperature is preferably 10 to 100° C., more preferably 20 to 60° C. The reaction time is preferably 0.5 to 30 hr, more preferably 2 to 20 hr.

Step (d-7)

In this step, compound (I-d) is reacted with a compound having a —$CONH_2$ group or —$OCONH_2$ group and treated with a base to produce compound (I-e). The reaction of compound (I-d) and a compound having a —$CONH_2$ group or —OCONH$_2$ group is performed in a solvent that does not influence the reaction and using an acid catalyst.

Examples of the acid catalyst include methanesulfonic acid, trifluoromethanesulfonic acid, toluenesulfonic acid and the like, of which methanesulfonic acid or toluenesulfonic acid is preferable. The amount of the acid catalyst to be used is preferably 0.05 to 0.5 mol, particularly preferably 0.1 to 0.3 mol, per 1 mol of compound (I-d).

Examples of the compound having a —CONH$_2$ group or —OCONH$_2$ group include Fmoc-NH$_2$, HCONH$_2$, CF$_3$CONH$_2$, AcNH$_2$, EtOCONH$_2$, Cbz-NH$_2$ and the like, of which Fmoc-NH$_2$, EtOCONH$_2$ and the like are preferable. Here, "Fmoc-" means a 9-fluorenylmethoxycarbonyl group (hereinafter to be also referred to as Fmoc group), and "Cbz-" means a benzyloxycarbonyl group (hereinafter to be also referred to as Cbz group).

As a reagent to be used as a material of step (a) (i.e., hydroxide, halide, alkylsulfonyloxylation product (e.g., methanesulfonyloxylation product etc. corresponding to R$^7$) or arylsulfonyloxylation product (e.g., p-toluenesulfonyloxylation product etc.), hereinafter to be abbreviated as "reagent of step (a)"), a commercially available product can be used. The reagent of step (a) can be produced by, for example, (1) halogenation, alkylsulfonyloxylation or arylsulfonyloxylation of a hydroxide corresponding to R$^7$, or (2) a reduction reaction (e.g., catalytic hydrogenation reaction in the presence of a metal catalyst such as platinum-carbon (Pt/C), palladium-carbon (Pd/C), rhodium-carbon (Rh/C), Raney-nickel or the like, etc.) of an unsaturated hydroxide corresponding to R$^7$, and subsequent halogenation, alkylsulfonyloxylation or arylsulfonyloxylation.

In the production of the reagent of step (a), examples of the reagent to be used for conversion to a leaving group from a hydroxyl group include, in addition to halogenating agents such as chlorinating agents (thionyl chloride, N-chlorosuccinimide (NCS) and the like), brominating agents (hydrobromic acid, acetyl bromide, N-bromosuccinimide (NBS), phosphorus tribromide, diphenylphosphine/bromine and the like) and the like, alkylsulfonylating agents such as methanesulfonyl chloride, trifluoromethanesulfonyl chloride and the like, arylsulfonylating agents such as benzenesulfonyl chloride, p-toluenesulfonyl chloride and the like, and the like, of which thionyl chloride, hydrobromic acid and the like as halogenating agents are preferable.

This reaction is performed in a solvent that does not influence the reaction. Examples of the solvent include water; halogenated hydrocarbons such as chloroform, dichloromethane and the like; aromatic hydrocarbons such as benzene, toluene, xylene and the like; nitriles such as acetonitrile, propionitrile and the like; ethers such as tetrahydrofuran, 1,4-dioxane, diethyl ether and the like, of which water, halogenated hydrocarbons such as chloroform and the like are preferable. The reaction temperature is preferably 10 to 120° C., more preferably 50 to 100° C. The reaction time is preferably 1 to 72 hr, more preferably 3 to 24 hr.

The aforementioned compound represented by Z—Y—H wherein Q' is a single bond can also be produced by, for example, the following method. That is, introduction of R$^7$ on the benzene ring can be performed by (1) Friedel-Crafts reaction using a halide (chloride, bromide, or iodide) corresponding to R$^7$, a carboxylic acid or acid halide corresponding to R$^7$, (2) a method comprising subjecting a compound corresponding to the above-mentioned compound (IV) (a compound wherein a Q'H group is replaced by a —CHO group) to carbon homologation by a Wittig reaction and, followed by catalytic hydrogenation and the like, or (3) conventional organic synthesis reactions such as cross coupling using a metal catalyst and the like.

In each of the above-mentioned schemes, the carbon number of organic group shown by R$^7$, the kind of halogen atom, reaction reagent and the like are shown for convenience, and can be appropriately changed within the range of the above-mentioned definitions.

Examples of the nucleoside, nucleotide or oligonucleotide (a) used in this step include a compound represented by the following formula (a-I) (i.e., nucleoside or oligonucleotide).

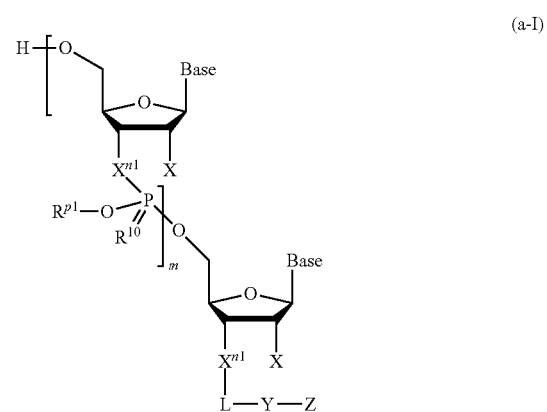

(a-I)

wherein m is an integer of not less than 0;

Base in the number of m+1 are each independently optionally protected nucleic acid base;

X in the number of m+1 are each independently a hydrogen atom, a halogen atom, an optionally protected hydroxy group, or a divalent organic group bonded to 2-position carbon atom and 4-position carbon atom;

X$^{n1}$ in the number of m+1 are each independently an oxygen atom or NH;

R$^{10}$ in the number of m are each independently an oxygen atom or a sulfur atom;

R$^{p1}$ in the number of m are each independently is a protecting group of phosphoric acid group;

L, Y and Z are as defined above.

In the following, a compound represented by the formula (a-I) is sometimes to be abbreviated as "compound (a-I)". Also, compounds represented by other formulas are sometimes abbreviated similarly.

The amino group of the nucleic acid base is preferably protected by a protecting group. As the protecting group, acetyl group, phenoxyacetyl group, 4-isopropylphenoxyacetyl group, benzoyl group, isobutyryl group, (2-hexyl) decanoyl group, dimethylformamidinyl group, and =NC(R$^{11}$)—N(R$^{12}$)(R$^{13}$) group wherein R$^1$ is a methyl group, R$^{12}$ and R$^{13}$ are each independently a C$_{1-5}$ alkyl group, or R$^{11}$ and R$^{12}$ are optionally joined to form, together with the carbon atom and nitrogen atom bonded thereto, a 5-membered or 6-membered nitrogen-containing hydrocarbon ring are preferable. Examples of the aforementioned=NC(R$^{11}$)—N(R$^{12}$)(R$^{13}$) group include a 1-(dimethylamino)ethylidene group. When compound (a-I) has plural amino groups, the amino-protecting group may be only one kind or two or more kinds.

When m is 0, compound (a-I) is a nucleoside, and when m is one or more, compound (a-I) is an oligonucleotide. m is preferably not more than 49, more preferably not more than 29, further preferably not more than 19, particularly preferably not more than 4, and most preferably not more than 2.

As the halogen atom for X, a fluorine atom or a chlorine atom is preferable, and a fluorine atom is more preferable.

The protecting group of the optionally protected hydroxy group for X is not particularly limited and, for example, any protecting group described in PROTECTIVE GROUPS IN ORGANIC SYNTHESIS, 3rd ed., JOHN WILLY&SONS (1999), which is incorporated herein by reference in its entirety, and the like can be mentioned. Specifically, methyl group, benzyl group, p-methoxybenzyl group, tert-butyl group, methoxymethyl group, methoxyethyl group, 2-tetrahydropyranyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, trimethylsilyl group, triethylsilyl group, triisopropylsilyl group, tert-butyldimethylsilyl group, [(triisopropylsilyl)oxy]methyl (Tom) group, 1-(4-chlorophenyl)-4-ethoxypiperidin-4-yl (Cpep) group and the like can be mentioned. The protecting group of the optionally protected hydroxy group is preferably a triethylsilyl group, a triisopropylsilyl group or a tert-butyldimethylsilyl group, particularly preferably a tert-butyldimethylsilyl group, from the aspects of economic efficiency and easy availability.

The "divalent organic group bonded to 2-position carbon atom and 4-position carbon atom" for X is not particularly limited as long as it is bonded to 2-position carbon atom and 4-position carbon atom of nucleoside. Examples of the divalent organic group include an optionally substituted $C_{2-7}$ alkylene group, and a divalent organic group constituted of an optionally substituted $C_{1-7}$ alkylene group and a divalent linker selected from —O—, —NR$^{33}$— (R$^{33}$ is a hydrogen atom or a $C_{1-6}$ alkyl group), —S—, —CO—, —COO—, —OCONR$^{34}$— (R$^{34}$ is a hydrogen atom or a $C_{1-6}$ alkyl group) and —CONR$^{35}$— (R$^{35}$ is a hydrogen atom or a $C_{1-6}$ alkyl group), and the like. Examples of the substituent that the $C_{1-7}$ alkylene group and $C_{2-7}$ alkylene group optionally have include a methylidene group (CH$_2$=).

As the "divalent organic group bonded to 2-position carbon atom and 4-position carbon atom", an optionally substituted $C_{2-7}$ alkylene group, —OR$^i$— (R$^i$ is a $C_{1-6}$ alkylene group bonded to 4-position carbon atom), —O—NR$^{33}$—R$^j$— (R$^j$ is a $C_{1-6}$ alkylene group bonded to 4-position carbon atom, R$^{33}$ is as defined above), —O—R$^k$—O—R$^l$—(R$^k$ is a $C_{1-6}$ alkylene group, R$^l$ is a $C_{1-6}$ alkylene group bonded to and crosslinked with 4-position carbon atom) are preferable, —OR$^i$— (R$^i$ is as defined above), —O—NR$^{33}$—R$^j$— (R$^j$ and R$^{33}$ are as defined above), —O—R$^k$—O—R$^l$— (R$^k$ and R$^l$ are as defined above) are more preferable. $C_{1-6}$ alkylene groups for R$^i$, R$^j$, R$^k$ and R$^l$ are preferably each independently a methylene group or an ethylene group.

As the "divalent organic group bonded to 2-position carbon atom and 4-position carbon atom", —O—CH$_2$—, —O—CH$_2$—CH$_2$—, —O—NR$^{33}$—CH$_2$— (R$^{33}$ is as defined above), —O—CH$_2$—O—CH$_2$— are more preferable, —O—CH$_2$—, —O—CH$_2$—CH$_2$—, —O—NH—CH$_2$—, —O—N(CH$_3$)—CH$_2$—, —O—CH$_2$—O—CH$_2$— (in each of which the left side is bonded to 2-position carbon atom and the right side is bonded to 4-position carbon atom) are further preferable.

X in the number of m+1 are each independently preferably a hydrogen atom, a halogen atom or an optionally protected hydroxy group, more preferably a hydrogen atom or an optionally protected hydroxy group.

The protecting group of phosphoric acid group for R$^{p1}$ is not particularly limited as long as it is removable under basic conditions under and can be used as a protecting group of phosphoric acid group. A group represented by —CH$_2$CH$_2$WG (WG is an electron-withdrawing group) is preferable.

Examples of the electron-withdrawing group for WG include cyano group, nitro group and the like, preferably cyano group.

R$^{p1}$ in the number of m are preferably each independently a group represented by —CH$_2$CH$_2$WG.

X$^{n1}$ in the number of m+1 are preferably oxygen atoms.

Explanations of L, Y and Z are as mentioned above.

Compound (a-I) is preferably a compound represented by the following formula (a-i) (definition and explanation of symbols in the following formula are as mentioned above).

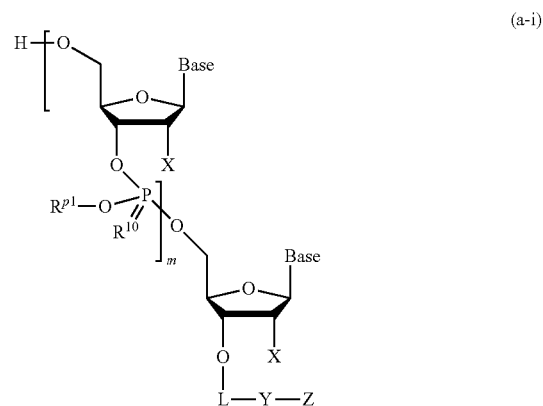

(a-i)

Compound (a-I) can be produced by a method known per se or a method analogous thereto. For example, compound (a-I) wherein m is 0, X$^{n1}$ is an oxygen atom, L is a succinyl group can be produced by, for example, as in the following formulas, first reacting nucleoside (i) having 5'-hydroxy group protected by a temporary protecting group Q" and succinic anhydride in the presence of a base to synthesize nucleoside (ii), then condensing the obtained nucleoside (ii) and compound Z—Y—H in the presence of a condensing agent to synthesize nucleoside having protected 3'- and 5'-hydroxy groups, and removing the temporary protecting group Q" with an acid.

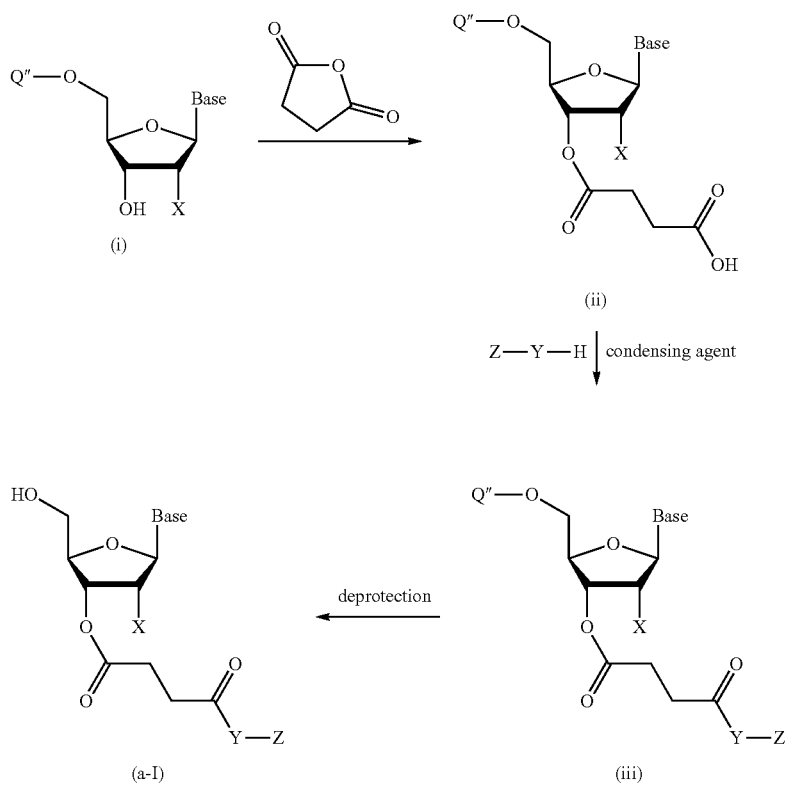

The conversion reaction from nucleoside (i) to nucleoside (ii) is advantageously performed in a solvent inert to the reaction. Such solvent is not particularly limited as long as the reaction proceeds, and halogenated solvents such as dichloromethane, 1,2-dichloroethane, chloroform, carbon tetrachloride and the like, aromatic solvents such as benzene, toluene, xylene and the like, or aliphatic solvents such as pentane, hexane, heptane, octane and the like, or ether solvents such as diethyl ether, tetrahydrofuran, cyclopentyl methyl ether and the like, and mixed solvents thereof are preferable. Of these, dichloromethane or chloroform is particularly preferable.

While the base to be used for the synthesis of nucleoside (ii) is not particularly limited, an organic base is preferable, and triethylamine is more preferable.

The condensation reaction for synthesizing nucleoside (iii) is advantageously performed in a solvent inert to the reaction. Such solvent is not particularly limited as long as the reaction proceeds, and halogenated solvents such as dichloromethane, 1,2-dichloroethane, chloroform, carbon tetrachloride and the like, aromatic solvents such as benzene, toluene, xylene and the like, aliphatic solvents such as pentane, hexane, heptane, octane and the like, and these combination are preferable. Of these, dichloromethane and chloroform are particularly preferable.

As the condensing agent to be used for the condensation reaction of nucleoside (ii) and Z—Y—H, dicyclohexylcarbodiimide (DCC), diisopropylcarbodiimide (DIC), N-ethyl-N'-3-dimethylaminopropylcarbodiimide and hydrochloride thereof (EDC. HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like can be mentioned. Of these, HBTU, HCTU, N-ethyl-N'-3-dimethylaminopropylcarbodiimide and hydrochloride thereof (EDC. HCl) are preferable.

The amount of the condensing agent to be used is, for example 1 to 10 mol, preferably 1 to 5 mol, per 1 mol of nucleoside (ii). The amount of Z—Y—H to be used is, for example 1 to 10 mol, preferably 1 to 5 mol, per 1 mol of nucleoside (ii). The reaction temperature is not particularly limited as long as the reaction proceeds, and −10° C. to 50° C. is preferable, 0° C. to 30° C. is more preferable. The reaction time is, for example 30 min to 70 hr.

Removal of the temporary protecting group Q from nucleoside (iii) (deprotection) can be performed in the same manner as in step (4) of the present invention.

Compound (a-I) wherein L is other than a succinyl group can also be synthesized by performing a similar reaction by using the corresponding acid anhydride, corresponding dicarboxylic acid halide, active ester of the corresponding dicarboxylic acid or the like instead of succinic anhydride in the above-mentioned synthesis method. Compound (a-I) wherein $X''^1$ is NH can also be synthesized by performing a similar reaction by using nucleoside wherein a 3'-hydroxy group is an amino group instead of nucleoside (i) in the above-mentioned synthesis method. Compound (a-I) wherein m is one or more can be synthesized by repeating a 5'-terminal elongation process by using compound (a-I) wherein m is 0 as a starting material.

Of compounds (a-i), a compound represented by the formula (a-II) (i.e., nucleoside or oligonucleotide) is preferable.

(a-II)

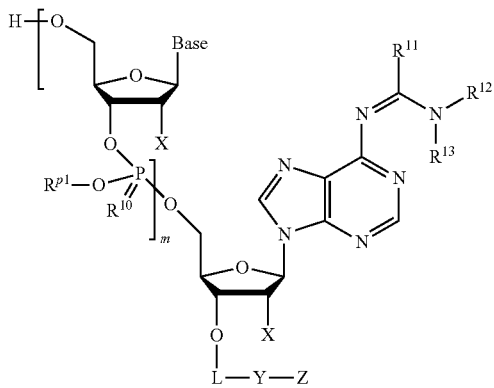

wherein m, Base in the number of m, X in the number of m+1, $R^{10}$ in the number of m, $R^{p1}$ in the number of m, L, Y and Z are each independently as defined above;

$R^1$ is a methyl group, $R^{12}$ and $R^{13}$ are each independently a $C_{1-5}$ alkyl group, or $R^{11}$ and $R^{12}$ are optionally joined to form, together with the carbon atom and nitrogen atom bonded thereto, a 5-membered or 6-membered nitrogen-containing hydrocarbon ring.

In the formula (a-II), preferably, $R^{p1}$ in the number of m are each independently a group represented by —CH$_2$CH$_2$WG.

In the formula (a-II), m is preferably 0. That is, of compounds (a-II), a compound represented by the formula (a-III) (i.e., nucleoside) is preferable (definition and explanation of the symbols in the following formula are as mentioned above).

(a-III)

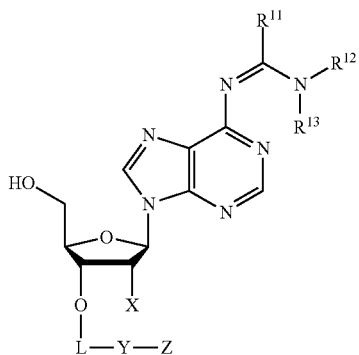

In the formula (a-II) and the formula (a-III), $R^{11}$ is preferably a methyl group and $R^{12}$ and $R^{13}$ are preferably each independently a $C_{1-5}$ alkyl group, and $R^{11}$, $R^{12}$ and $R^{13}$ are more preferably methyl groups.

Explanations of other symbols in the formula (a-II) and the formula (a-III) are as mentioned above.

In the present invention, when oligonucleotide wherein the first residue has adenine as a nucleic acid base is produced, production of a branched product and the like can be suppressed by using compound (a-II) (particularly, compound (a-III)) as a nucleoside, nucleotide or oligonucleotide (a) which is a starting material. As used herein, the branch product refers to a byproduct produced when an amino-protecting group of the nucleic acid base of the object compound is detached and the amino group and a monomer are bonded.

In compounds (a-i), a compound represented by the formula (a-IV) (i.e., nucleoside or oligonucleotide) is preferable.

(a-IV)

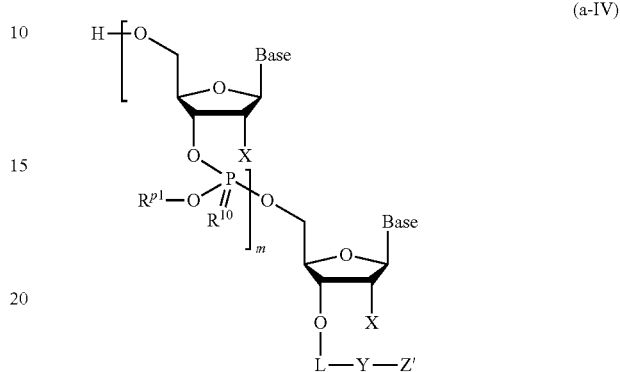

wherein m, Base in the number of m+1, X in the number of m+1, $R^{10}$ in the number of m, $R^{p1}$ in the number of m, L and Y are each independently as defined above;

Z' is a group represented by the formula (a2"):

(a2")

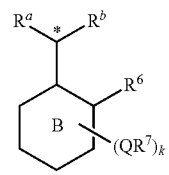

wherein

* indicates a bonding position;

$R^6$ is a hydrogen atom or when $R^b$ is a group represented by the following formula (a3), it optionally shows, together with $R^8$, a single bond or —O— to form, together with ring B and ring C, a fused ring;

k is an integer of 1 to 4;

Q in the number of k are each independently —O—, —C(=O)—, —C(=O)O—, —OC(=O)—, —C(=O)NH— or —NHC(=O)—;

$R^7$ in the number of k are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;

ring B optionally has, in addition to QR$^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and $R_b$ is a hydrogen atom, or a group represented by the formula (a3):

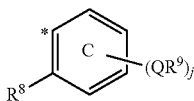

(a3)

wherein * indicates a bonding position;
j is an integer of 0 to 4;
Q in the number of j are each independently as defined above;
$R^9$ in the number of j are each independently a hydrocarbon group wherein a linear aliphatic hydrocarbon group having a carbon number of not less than 10 is bonded via a single bond or a linker, or an organic group having at least one aliphatic hydrocarbon group having one or more branched chains and having a total carbon number of not less than 14 and not more than 300;
$R^8$ is a hydrogen atom, or optionally shows, together with $R^6$, a single bond or —O— to form a fused ring with ring B and ring C; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group.
In the formula (a-IV), $R^{p1}$ in the number of m are preferably each independently a group represented by —CH$_2$CH$_2$WG.
In the formula (a-IV), m is preferably 0.
Explanations of other symbols in the formula (a-IV) are as mentioned above.
In compounds (a-IV), a compound represented by the following formula (a-V) (i.e., nucleoside) is preferable (definition and explanation of the symbols in the following formula are as mentioned above).

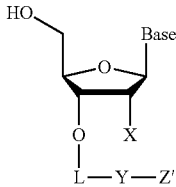

(a-V)

In compounds (a-I), compound (a-IV) (particularly, compound (a-V)) having Z' represented by the formula (a2") (i.e., structure of cyclohexylmethyl group) in the anchor shows high solubility in non-polar solvents as compared to other compounds (a-I) having Z represented by the formula (a2) (i.e., structure of benzyl group) in the anchor. Therefore, using compound (a-IV) (particularly, compound (a-V)), the production method of the present invention can be performed at a higher concentration and the productivity is strikingly improved. Explanation of Z' represented by the formula (a2") is the same as that of Z represented by the aforementioned the formula (a2").
In the formulas (a-IV) and (a-V), a combination wherein L is a succinyl group or a group represented by the formula (a1') (in the formula (a1'), $R^1$ and $R^2$ are each independently a $C_{1-10}$ alkyl group, $L^1$ is a divalent phenylene group, and $L^2$ is a single bond), and Y—Z' is 3,4,5-tris(octadecyloxy)cyclohexylmethyloxy group, 3,5-bis(docosyloxy)cyclohexylmethyloxy group, 3,5-bis[3',4',5'-tris(octadecyloxy)cyclohexylmethyloxy]cyclohexylmethyloxy group, 3,4,5-tris[3',4',5'-tris(octadecyloxy)cyclohexylmethyloxy]cyclohexylmethyloxy group, 3,4,5-tris(octadecyloxy)cyclohexylmethylamino group, 2,4-bis(docosyloxy)cyclohexylmethylamino group, 3,5-bis(docosyloxy)cyclohexylmethylamino group, 4-methoxy-2-[3',4',5'-tris(octadecyloxy)cyclohexylmethyloxy]cyclohexylmethylamino group, 4-methoxy-2-[3',4',5'-tris(octadecyloxy)cyclohexylmethyloxy]cyclohexylmethylamino group, 2,4-bis(dodecyloxy)cyclohexylmethylamino group, 3,5-bis[3',4',5'-tris(octadecyloxy)cyclohexylmethyloxy]cyclohexylmethylamino group, or 3,4,5-tris[3',4',5'-tris(octadecyloxy)cyclohexylmethyloxy]cyclohexylmethylamino group is preferable for solid-liquid separation.
In the formulas (a-IV) and (a-V), a combination wherein L is a succinyl group, and
Y—Z' is 3,4,5-tris(octadecyloxy)cyclohexylmethyloxy group, 3,5-bis(docosyloxy)cyclohexylmethyloxy group, 3,5-bis[3',4',5'-tris(octadecyloxy)cyclohexylmethyloxy]cyclohexylmethyloxy group, 3,4,5-tris[3',4',5'-tris(octadecyloxy)cyclohexylmethyloxy]cyclohexylmethyloxy group, 3,4,5-tris(octadecyloxy)cyclohexylmethylamino group, 2,4-bis(docosyloxy)cyclohexylmethylamino group, 3,5-bis(docosyloxy)cyclohexylmethylamino group, 4-methoxy-2-[3',4',5'-tris(octadecyloxy)cyclohexylmethyloxy]cyclohexylmethylamino group, 4-methoxy-2-[3',4',5'-tris(octadecyloxy)cyclohexylmethyloxy]cyclohexylmethylamino group, 2,4-bis(dodecyloxy)cyclohexylmethylamino group, 3,5-bis[3',4',5'-tris(octadecyloxy)cyclohexylmethyloxy]cyclohexylmethylamino group, or 3,4,5-tris[3',4',5'-tris(octadecyloxy)cyclohexylmethyloxy]cyclohexylmethylamino group is more preferable for solid-liquid separation.
In the formulas (a-IV) and (a-V), a combination wherein L is a succinyl group, and
Y—Z' is 3,4,5-tris(octadecyloxy)cyclohexylmethyloxy group, 3,5-bis(docosyloxy)cyclohexylmethyloxy group, 3,5-bis[3',4',5'-tris(octadecyloxy)cyclohexylmethyloxy]cyclohexylmethyloxy group, or 3,4,5-tris[3',4',5'-tris(octadecyloxy)cyclohexylmethyloxy]cyclohexylmethyloxy group is more preferable for solid-liquid separation.
In the formulas (a-IV) and (a-V), a combination wherein L is a succinyl group, and
Y—Z' is 3,4,5-tris(octadecyloxy)cyclohexylmethyloxy group is particularly preferable for solid-liquid separation.
Examples of the nucleoside, nucleotide or oligonucleotide (a) include a compound represented by the following formula (a-VI) (i.e., nucleoside or oligonucleotide).

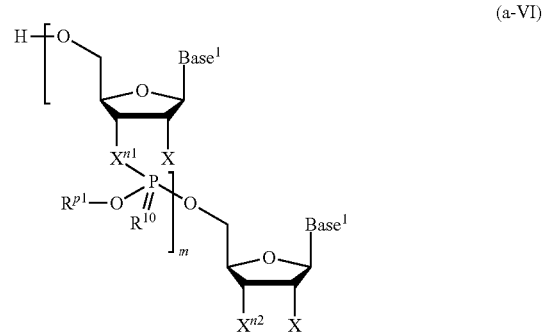

(a-VI)

wherein at least one of Base¹ in the number of m+1 is a nucleic acid base protected by -L-Y—Z, and the rest is an optionally protected nucleic acid base;

$X^{n1}$ in the number of m are each independently an oxygen atom or NH;

$X^{n2}$ is a protected hydroxy or amino group;

m, X in the number of m+1, $R^{10}$ in the number of m, $R^{p1}$ in the number of m, L, Y and Z are each independently as defined above.

In the formula (a-VI), at least one of Base¹ in the number of m+1 is a nucleic acid base protected by -L-Y—Z. Explanations of the nucleic acid base and -L-Y—Z are as mentioned above.

Explanation of the optionally protected nucleic acid base is also as mentioned above.

The protecting group of the protected hydroxy group ($X^{n2}$) is not particularly limited and, for example, any protecting group described in PROTECTIVE GROUPS IN ORGANIC SYNTHESIS, 3rd ed., JOHN WILLY&SONS (1999), which is incorporated herein by reference in its entirety, and the like can be mentioned. Specifically, methyl group, benzyl group, p-methoxybenzyl group, tert-butyl group, methoxyethyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, triethylsilyl group, triisopropylsilyl group, tert-butyldimethylsilyl group, [(triisopropylsilyl)oxy]methyl (Tom) group, 1-(4-chlorophenyl)-4-ethoxypiperidin-4-yl (Cpep) group and the like can be mentioned. The hydroxy-protecting group is preferably a triethylsilyl group, triisopropylsilyl group or tert-butyldimethylsilyl group, more preferably a tert-butyldimethylsilyl group from the aspects of economic efficiency and easy availability. Protection and deprotection of the hydroxy group are well known and can be performed by, for example, the method described in the aforementioned PROTECTIVE GROUPS IN ORGANIC SYNTHESIS.

The protecting group of the protected amino group ($X^{n2}$) is not particularly limited and, for example, the protecting groups described in Greene's PROTECTIVE GROUPS in ORGANIC SYNTHESIS, 4th ed., Wiley-Interscience (2006), which is incorporated herein by reference in its entirety, and the like can be mentioned. Specific examples of each protecting group include pivaloyl group, pivaloyloxymethyl group, acetyl group, trifluoroacetyl group, phenoxyacetyl group, 4-isopropylphenoxyacetyl group, 4-tert-butylphenoxyacetyl group, benzoyl group, isobutyryl group, (2-hexyl)decanoyl group, dimethylformamidinyl group, 1-(dimethylamino)ethylidene group and 9-fluorenylmethyloxycarbonyl group. The amino-protecting group is preferably a acetyl group, phenoxyacetyl group, 4-isopropylphenoxyacetyl group, benzoyl group, isobutyryl group, (2-hexyl)decanoyl group, dimethylformamidinyl group, or 1-(dimethylamino)ethylidene group. Protection and deprotection of the amino group are well known and can be performed by, for example, the method described in the aforementioned PROTECTIVE GROUPS in ORGANIC SYNTHESIS.

In the formula (a-VI), $X^{n1}$ in the number of m are preferably oxygen atoms.

In the formula (a-VI), $X^{n2}$ is preferably a protected hydroxy group.

In the formula (a-VI), $R^{p1}$ in the number of m are preferably each independently a group represented by —CH₂CH₂WG.

In the formula (a-VI), explanations of other symbols are as mentioned above.

Compound (a-VI) is preferably a compound represented by the following formula (a-vi).

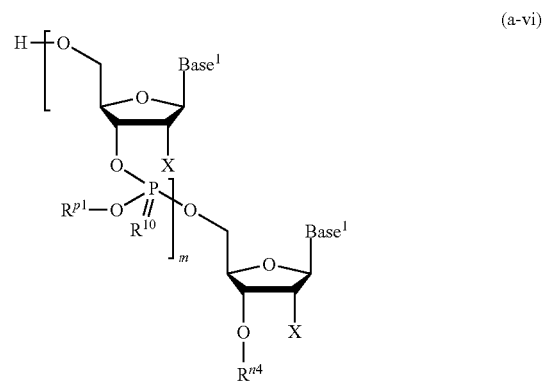

(a-vi)

wherein $R^{n4}$ is a hydroxy-protecting group;

m, Base¹ in the number of m+1, X in the number of m+1, $R^{10}$ in the number of m, $R^{p1}$ in the number of m, L, Y and Z are each independently as defined above.

Explanation of $R^{n4}$ in the formula (a-vi) is the same as that of the hydroxy-protecting group for $X^{n2}$.

Explanations of other symbols in the formula (a-vi) are as mentioned above.

Examples of the substituted nucleotide or oligonucleotide (α) include a compound represented by the following formula (a-VII).

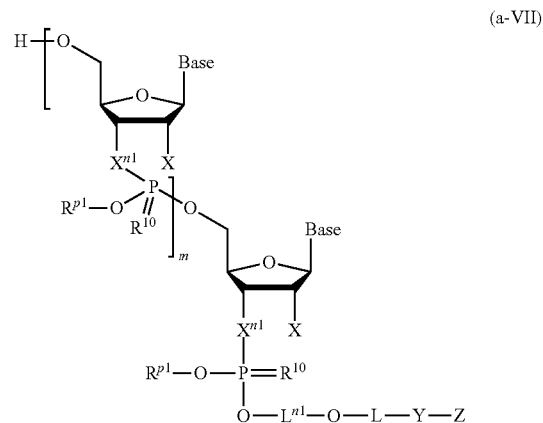

(a-VII)

wherein

X in the number of m+1$^{n1}$ are each independently an oxygen atom or NH;

$L^{n1}$ is an organic group;

m, Base in the number of m+1, X in the number of m+1, $R^{10}$ in the number of m+1, $R^{p1}$ in the number of m+1, L, Y and Z are each independently as defined above.

In the formula (a-VII), $L^{n1}$ is preferably a $C_{2-6}$ alkylene group, more preferably an ethylene group.

In the formula (a-VII), $X^{n1}$ in the number of m+1 are preferably oxygen atoms.

In the formula (a-VII), $R^{p1}$ in the number of m+1 are preferably each independently a group represented by —CH₂CH₂WG.

Explanations of other symbols in the formula (a-VII) are as mentioned above.

Compound (a-VII) is preferably a compound represented by the following formula (a-vii) (definition and explanation of the symbols in the following formula are as mentioned above).

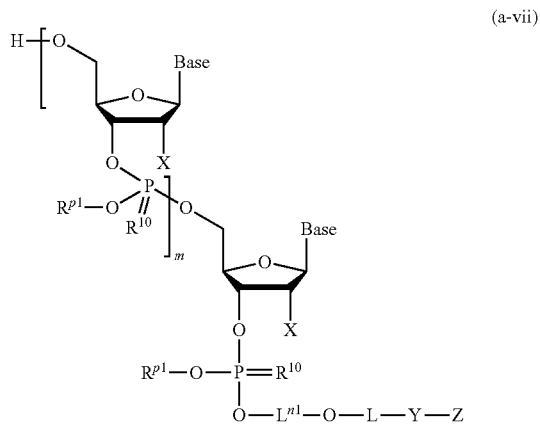

(a-vii)

Compound (a-VII) can be produced by a method known per se or a method analogous thereto. Compound (a-VII) wherein m is 0, $X^{n1}$ is an oxygen atom, and L is a succinyl group can be produced, for example, by the following steps.

(i) condensing compound Z—Y—H and succinic anhydride to produce Z—Y—CO(CH$_2$)$_2$COOH, (ii) condensing the obtained Z—Y—CO(CH$_2$)$_2$COOH and a compound represented by formula: HO-L$^{n1}$-OQ'' (wherein Q'' is a temporary protecting group and L$^{n1}$ is an organic group) in the presence of a condensing agent, and deprotecting same to produce Z—Y—CO(CH$_2$)$_2$CO—O-L$^{n1}$-OH, (iii) reacting the obtained Z—Y—CO(CH$_2$)$_2$CO—O-L$^{n1}$-OH with phosphoramidited nucleoside to produce compound (a-VII) wherein m is 0, $X^{n1}$ is an oxygen atom and L is a succinyl group.

The aforementioned condensation reaction and deprotection are well known to those of ordinary skill in the art and those of ordinary skill in the art can perform them by appropriately setting the conditions.

Compound (a-VII) wherein L is other than a succinyl group can also be produced by performing a similar reaction by using the corresponding acid anhydride, corresponding dicarboxylic acid halide, active ester of corresponding dicarboxylic acid or the like instead of succinic anhydride. Compound (a-VII) wherein $X^{n1}$ is NH can be produced by performing a similar reaction by using nucleoside wherein 3'-amino group is phosphoramidited. Compound (a-VII) wherein m is one or more can be produced by repeating an elongation process using compound (a-VII) wherein m is 0 as the starting material.

The nucleoside, nucleotide or oligonucleotide (a) or the substituted nucleotide or oligonucleotide (α) used in this step is preferably compound (a-I), compound (a-VI) or compound (a-VII), more preferably compound (a-i), compound (a-vi) or compound (a-vii), still more preferably compound (a-i) or compound (a-vi), further preferably compound (a-i), still further preferably compound (a-II) or compound (a-IV), particularly preferably compound (a-III) or compound (a-V).

The nucleoside, nucleotide or oligonucleotide (b) used in this step has a 5'-hydroxy group protected by a temporary protecting group. The temporary protecting group of hydroxy group is not particularly limited as long as it can be deprotected under acidic conditions and can be used as a hydroxy-protecting group. Examples thereof include trityl group, 9-(9-phenyl)xanthenyl group, 9-phenylthioxanthenyl group, bis(C$_{1-6}$ alkoxy)trityl groups such as 1,1-bis(4-methoxyphenyl)-1-phenylmethyl group (dimethoxytrityl group) and the like, mono(C$_{1-18}$ alkoxy)trityl groups such as 1-(4-methoxyphenyl)-1,1-diphenylmethyl group (monomethoxytrityl group) and the like, and the like. Among these, the temporary protecting group of hydroxy group is preferably a monomethoxytrityl group or a dimethoxytrityl group, more preferably a dimethoxytrityl group, in view of easiness of deprotection and easy availability.

A nucleoside, nucleotide or oligonucleotide (b) can be synthesized according to a known method for reacting a phosphoramiditing reagent (e.g., M. H. Caruthers et al., Method in Enzymology 1987, 154, 287-313; S. L. Beaucage and M. H. Caruthers, Tetrahedron Letters 1981, 22, 1859-1862, which are incorporated herein by reference in their entireties). A phosphoramiditing reagent is commercially available and can also be obtained easily. For example, a nucleoside, nucleotide or oligonucleotide (b) wherein a 3'-amino group is phosphoramidited can be synthesized by reacting a nucleoside, nucleotide or oligonucleotide (b) having a 3'-amino group and 2-cyanoethyl N,N-diisopropylchlorophosphoramidite in a halogen solvent such as dichloromethane or the like.

As one embodiment of the production method of a nucleoside, nucleotide or oligonucleotide (b), a method for producing nucleoside, nucleotide or oligonucleotide (b) wherein a 3'-hydroxy group is phosphoramidited (hereinafter sometimes to be abbreviated as "phosphoramidited compound (b)") from a phosphoramidited nucleoside, nucleotide or oligonucleotide (b) having a 3'-hydroxy group (hereinafter sometimes to be abbreviated as "compound (b)") is explained below.

This production method includes reactions for monoselectively activating a phosphitylating agent precursor having two nitrogen substituents on a trivalent phosphorus to give a phosphitylating agent, and phosphitylating a 3'-hydroxy group of compound (b) by using the phosphitylating agent in the presence of a base. That is, this production method is a production method of phosphoramidited compound (b) including the following step (P1) and step (P2).

(P1) A step including reacting a phosphitylating agent precursor represented by the following formula (p1):

(p1)

wherein $X^{p1}$ is an oxygen atom or a sulfur atom;

$R^{p2}$ is an aromatic ring, a hydroxy-protecting group or a protecting group of thiol group;

$R^{p3}$ and $R^{p4}$ are each independently an alkyl group, and the alkyl group may form, together with the adjacent nitrogen atom, a ring, with an activator in a solvent to prepare a phosphitylating agent represented by the following formula (p2):

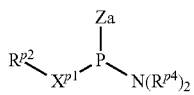

(p2)

wherein

Za is a group derived from the activator; and other symbols are as defined above, and (P2) a step including reacting compound (b) with the phosphitylating agent obtained in step (P1) in a solvent in the presence of a base to phosphitylate the 3'-hydroxy group of the compound (b).

Step (P1)

In the formula (p1), as the aromatic ring for $R^{p2}$, phenyl, 4-nitrophenyl, 2,4-dinitrophenyl, pentafluorophenyl, pentachlorophenyl, 2-bromophenyl, 4-bromophenyl, 2-methylphenyl, 2,6-dimethylphenyl and the like can be mentioned, and 4-nitrophenyl is preferable.

In the formula (p1), examples of the hydroxy-protecting group or the protecting group of thiol group for $R^{p2}$ include $C_{1-6}$ alkyl group (e.g., methyl, ethyl, n-propyl, isopropyl, n-butyl, isobutyl, s-butyl, t-butyl, pentyl, isopentyl); cyanated $C_{1-6}$ alkyl group (e.g., 2-cyanoethyl, 2-cyano-1,1-dimethylethyl); ethyl group substituted by a substituted silyl group (e.g., 2-methyldiphenylsilylethyl, 2-trimethylsilylethyl, 2-triphenylsilylethyl); halogenated $C_{1-6}$ alkyl group (e.g., 2,2,2-trichloroethyl, 2,2,2-tribromoethyl, 2,2,2-trifluoroethyl); $C_{2-6}$ alkenyl group (e.g., ethenyl, 1-propenyl, 2-propenyl, 1-methyl-2-propenyl, 1-methyl-1-propenyl); $C_3$-6 cycloalkyl group (e.g., cyclopropyl, cyclobutyl, cyclopentyl, cyclohexyl); cyanated $C_{1-6}$ alkenyl group (e.g., 2-cyanobutenyl); $C_{7-11}$ aralkyl group (e.g., benzyl, (x-naphthylmethyl, 3-naphthylmethyl); and $C_{6-10}$ aryl group (e.g., phenyl, indenyl, naphthyl), more preferably cyanated $C_{1-6}$ alkyl group, particularly preferably 2-cyanoethyl.

In the formula (p1), $R^{p3}$ and $R^{p4}$ are each independently an alkyl group, and the alkyl group may form, together with the adjacent nitrogen atom, a ring (e.g., pyrrolidine). $R^{p3}$ and $R^{p4}$ are each preferably an isopropyl group.

As the phosphitylating agent precursor, the following compound is particularly preferable.

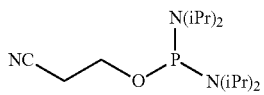

A phosphitylating agent is obtained by reacting a phosphitylating agent precursor with an activator.

An activator is an acid capable of substituting an amine on phosphoramidite to afford a reactive substituent with a hydroxy group and the like. To be specific, a weakly acidic activator with pKa of not less than 5, more preferably at least one kind selected from an azole compound with pKa of not less than 5 and a C-substituted product thereof. As the azole compound, tetrazole, triazole, imidazole and the like can be mentioned, as the C-substituted product, a compound di-substituted with a halogen atom such as dicyanoimidazole, bis(trifluoromethyl)imidazole, dichloroimidazole or the like is used. Particularly preferred are dicyanoimidazole and dichloroimidazole.

In the formula (p2), Za is a group derived from the activator and, for example, a group obtained by removing one hydrogen atom from the activator. When dicyanoimidazole is used as an activator, Za is dicyanoimidazolyl and when dichloroimidazole is used as an activator, Za is dichloroimidazolyl.

The solvent to be used in this step is not particularly limited as long as a phosphitylating agent precursor can be dissolved and an activator becomes poorly soluble, and is generally free of an acidic or basic functional group. As used herein, being "poorly soluble" approximately means that the concentration of the activator in a solvent is not more than 6 M. Specifically, toluene, benzene, o-xylene, m-xylene, p-xylene, ethylbenzene, pentane, hexane, heptane, octane, cyclopentane, cyclohexane, diethyl ether, diisopropyl ether, tert-butyl methyl ether, cyclopentyl methyl ether, carbon tetrachloride and the like can be mentioned, toluene and cyclohexane are preferable, and toluene is particularly preferable.

The reaction temperature and reaction time of this step are not particularly limited as long as the substrate or resultant product is not precipitated, and are generally not more than 40° C., preferably 0 to 30° C., more preferably 5 to 15° C., particularly preferably about 10° C., generally 0.5 to 24 hr, preferably 1 to 12 hr, more preferably 1 to 6 hr.

The amount of the activator and phosphitylating agent precursor to be used is not particularly limited as long as the phosphitylating agent precursor is activated, and it is generally an excess amount, preferably 1.5 to 10 molar equivalents, relative to the phosphitylating agent precursor. By reacting an excess amount of an activator with a phosphitylating agent precursor in a solvent, the phosphitylating agent precursor is activated and diisopropylamine by-produced in phosphitylating is simultaneously precipitated as a salt with the activator. Therefore, where necessary, a step for separating insoluble materials such as precipitate and the like can be performed between step (P1) and the following step (P2), and is preferably performed.

Step (P2)

In this step, phosphoramidited compound (b) is produced by phosphitylating the 3'-hydroxy group of compound (b) by reacting compound (b) with the phosphitylating agent obtained in step (P1) in a solvent in the presence of a base.

As the solvent to be used in this step, those similar to the solvent used in step (P1) (e.g., toluene) can be used. As the solvent to be used in this step, for example, dichloromethane, chloroform and the like can be mentioned. A mixed solvent of toluene and dichloromethane is preferable.

As a base to be used in this step, a base having basicity sufficient for neutralization of an acid (activator) produced by the reaction, and free of removal of cyanoethyl on phosphoric acid or formation of a P—N bond is selected. As such base, specifically, base with pKa 5 to 8, preferably, collidine, N-methylmorpholine, diethylaniline and the like can be used. When a base with pKa high than 8 is used, removal of cyana becomes remarkable, and when a base with pKa less than 5 is used, an activator regenerated as the reaction proceeds is not trapped sufficiently and a byproduct is produced.

In step (P2), a phosphitylating agent precursor may not be added but is preferably added.

Examples of the nucleoside, nucleotide or oligonucleotide (b) include a compound represented by the following formula (b-I) (i.e., nucleoside or oligonucleotide).

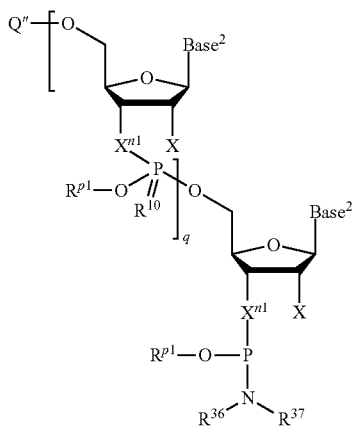

(b-I)

wherein
q is an integer of not less than 0;
Base$^2$ in the number of q+1 are each independently a nucleic acid base optionally protected by a protecting group selected from -L-X—Z and protecting groups used for nucleic acid synthesis;
X in the number of q+1, $R^{p1}$ in the number of q+1, $R^{10}$ in the number of q, L, X and Z are each independently as defined above;
$X^{n1}$ in the number of q+1 are each independently an oxygen atom or NH;
Q" is a temporary protecting group of hydroxy group removable under acidic conditions;
$R^{36}$ and $R^{37}$ are each independently an alkyl group, or a 5- or 6-membered saturated cyclic amino group formed together with the adjacent nitrogen atom, and the saturated cyclic amino group, optionally has, as a ring-constituting atom, one oxygen atom or sulfur atom besides nitrogen atom.
$R^{36}$ and $R^{37}$ are preferably each independently a $C_{1-10}$ alkyl group, or a 5- or 6-membered saturated cyclic amino group formed together with the adjacent nitrogen atom, more preferably a $C_{1-10}$ alkyl group, further preferably a $C_{1-6}$ alkyl group.
Explanation of the temporary protecting group of hydroxy group removable under acidic conditions is as mentioned above. Q" is preferably a monomethoxytrityl group or a dimethoxytrityl group, more preferably a dimethoxytrityl group.
The amino group of the nucleic acid base in the formula (b-I) is preferably protected by a protecting group. As the protecting group, a protecting group selected from -L-X—Z and protecting groups used for nucleic acid synthesis can be mentioned. Explanations of L, X and Z are as mentioned above. As the protecting group used for nucleic acid synthesis, acetyl group, phenoxyacetyl group, 4-isopropylphenoxyacetyl group, benzoyl group, isobutyryl group, (2-hexyl)decanoyl group, dimethylformamidinyl group, and =NC($R^{11}$)—N($R^{12}$) ($R^{13}$) group wherein $R^{11}$ is a methyl group, $R^{12}$ and $R^{13}$ are each independently a $C_{1-5}$ alkyl group, or $R^{11}$ and $R^{12}$ are optionally joined to form, together with the carbon atom and nitrogen atom bonded thereto, a 5-membered or 6-membered nitrogen-containing hydrocarbon ring is preferable. Examples of the aforementioned =NC ($R^{11}$)—N($R^{12}$) ($R^{13}$) group include a1-(dimethylamino)ethylidene group. When compound (b-I) has plural amino groups, the amino-protecting group may be only one kind or two or more kinds.

When q is 0, compound (b-I) is a nucleoside, and when q is one or more, compound (b-I) is an oligonucleotide. As compound (b-I) used in this step, q is preferably not more than 49, more preferably not more than 29, further preferably not more than 19, particularly preferably not more than 4, and most preferably not more than 2.
X in the number of q+1 are each independently preferably a hydrogen atom, a halogen atom or an optionally protected hydroxy group, more preferably a hydrogen atom or an optionally protected hydroxy group.
Base$^2$ are each independently preferably a nucleic acid base optionally protected by a protecting group selected from protecting groups used for nucleic acid synthesis.
$R^{p1}$ in the number of q+1 are preferably each independently a group represented by —CH$_2$CH$_2$WG.
$X^{n1}$ in the number of q+1 are preferably oxygen atoms.
Explanations of L, X and Z are as mentioned above.
Compound (b-I) is preferably a compound represented by the following formula (b-i).

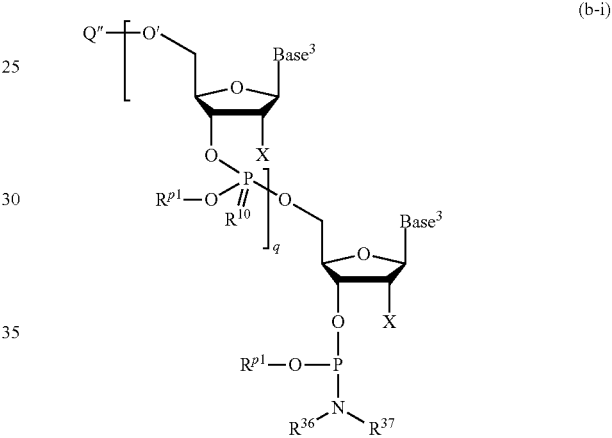

(b-i)

wherein
Base$^3$ in the number of q+1 are each independently a nucleic acid base optionally protected by protecting groups used for nucleic acid synthesis,
q, X in the number of q+1, $R^{p1}$ in the number of q+1, $R^{10}$ in the number of q, Q", $R^{36}$ and $R^{37}$ are each independently as defined above.
In the formula (b-i), explanations of the protecting groups used for nucleic acid synthesis, q, X in the number of q+1, $R^{p1}$ in the number of q+1, $R^{10}$ in the number of q, Q", $R^{36}$ and $R^{37}$ are as mentioned above.
A combination of the nucleoside, nucleotide or oligonucleotide (a) or substituted nucleotide or the oligonucleotide (α), and the nucleoside, nucleotide or oligonucleotide (b) used in this step is
preferably a combination of compound (a-I), compound (a-VI) or compound (a-VII) and compound (b-I),
more preferably a combination of compound (a-i), compound (a-vi) or compound (a-vii) and compound (b-i),
still more preferably a combination of compound (a-i) or compound (a-vi) and compound (b-i),
further preferably a combination of compound (a-i) and compound (b-i),
still further preferably a combination of compound (a-II) or compound (a-IV) and compound (b-i),
particularly preferably a combination of compound (a-III) or compound (a-V) and compound (b-i).

When the progress of the condensation reaction in this step is slow, a condensing agent (e.g., pyridine. trifluoroacetate, tetrazole, 5-benzylthio-1H-tetrazole, 4,5-dicyanoimidazole etc.) may be added.

This step is performed in a non-polar solvent. Examples of the non-polar solvent include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Only one kind of non-polar solvent may be used, or two or more kinds thereof may be used in combination. As the non-polar solvent, halogenated solvent, aromatic solvents, ester solvent, aliphatic solvent, and a combination of these are preferable; dichloromethane, chloroform, 1,2-dichloroethane, benzene, toluene, xylene, mesitylene, hexane, pentane, heptane, nonane, cyclohexane, ethyl acetate, isopropyl acetate and a combination of these are more preferable; and chloroform, dichloromethane, toluene, and a combination of these are further preferable. The same applies to the non-polar solvents used in this step and the following steps.

The amount of the nucleoside, nucleotide or oligonucleotide (b) used in this step is, for example 1 to 10 mol, preferably 1 to 5 mol, per 1 mol of the amount of the nucleoside, nucleotide or oligonucleotide (a) or the substituted nucleotide or oligonucleotide (α) used in this step.

The reaction temperature in this step is not particularly limited as long as the reaction proceeds, and is preferably 0° C. to 100° C., more preferably 20° C. to 50° C. The reaction time varies depending on the kind of the material to be used, reaction temperature and the like and is, for example 5 min to 24 hr.

Step (2) (Quench of Phosphoramidited Nucleoside, Nucleotide or Oligonucleotide (b))

In the present invention, step (3) (oxidation or sulfurization) and step (4) (deprotection) are performed after step (1) (condensation). Therefore, to suppress production of a byproduct in steps (3) and (4), the nucleoside, nucleotide or oligonucleotide (b) is preferably quenched before step (3). Therefore, the production method of the present invention preferably contains step (2) for adding a quencher to the reaction solution after condensation.

A quencher of phosphoramidited nucleoside or oligonucleotide, which is known in the field of the production method of oligonucleotide, can be used as a quencher in this step. Only one kind of a quencher may be used, or two or more kinds thereof may be used in combination. Examples of the quencher include alcohols, phenols and amines.

Examples of the alcohols usable as a quencher include optionally halogenated monovalent alcohols such as methanol, 2-propanol, t-butanol, 2,2,2,-trifluoroethanol, tetrahydrofurfuryl alcohol, furfurylalcohol, 2,3-O-isopropylidene-D-ribofuranose, 3'-O-triisopropylsilyl-thymidine and the like, optionally halogenated polyhydric alcohols such as ethylene glycol, diethylene glycol and the like.

Examples of the phenols usable as a quencher include 4-nitrophenol and pentafluorophenol. Examples of the amines usable as a quencher include morpholine.

The quencher is preferably at least one selected from alcohols and amines, more preferably at least one selected from methanol, 2-propanol, t-butanol, 2,2,2-trifluoroethanol, tetrahydrofurfuryl alcohol, and morpholine. To prevent falling off of the amino-protecting group of nucleic acid base in the oligonucleotide (e) during deprotection in step (4) (deprotection), the quencher is further preferably at least one selected from 2-propanol, t-butanol and 2,2-trifluoroethanol.

The amount of the quencher to be used in this step is preferably 1 to 20 mol, more preferably 1 to 10 mol, further preferably 1 to 5 mol, per 1 mol of the amount of the nucleoside, nucleotide or oligonucleotide (b) to be used in step (1).

The temperature of the reaction solution after addition of a quencher is not particularly limited as long as the nucleoside, nucleotide or oligonucleotide (b) can be quenched and is preferably 5° C. to 40° C., more preferably 15° C. to 30° C. The stirring time of the reaction solution after addition of a quencher varies depending on the kind of the quencher to be used, temperature and the like and is, for example 10 min to 3 hr.

Step (3) (Oxidation or Sulfurization)

In this step, the phosphite triester product (c) wherein the 5'-hydroxy group is protected by a temporary protecting group removable under acidic conditions is reacted with an oxidant or sulfurizing agent to convert the phosphite triester bond thereof to a phosphate triester bond or thiophosphate triester bond to give the oligonucleotide (d) wherein the 5'-hydroxy group is protected by a temporary protecting group removable under acidic conditions. When an oxidant is used, only one kind thereof may be used, or two or more kinds thereof may be used in combination. When a sulfurizing agent is used, only one kind thereof may be used, or two or more kinds thereof may be used in combination.

The oxidant to be used in this step is not particularly limited as long as it has an ability to oxidize a phosphite triester bond into a phosphate triester bond without oxidizing other moiety, at least one selected from iodine, (1S)-(+)-(10-camphanylsulfonyl)oxaziridine, tert-butyl hydroperoxide (TBHP), 2-butanone peroxide, 1,1-dihydroperoxycyclododecane, bis(trimethylsilyl)peroxide and m-chloroperbenzoic acid is preferably used.

To achieve a good oxidation reaction, the oxidant is preferably at least one selected from iodine, (1S)-(+)-(10-camphanylsulfonyl)oxaziridine, tert-butyl hydroperoxide, 2-butanone peroxide and 1,1-dihydroperoxycyclododecane, more preferably at least one selected from iodine, (1S)-(+)-(10-camphanylsulfonyl)oxaziridine, tert-butyl hydroperoxide, and 2-butanone peroxide, further preferably at least one selected from iodine and tert-butyl hydroperoxide, particularly preferably iodine. Such oxidant can be used by diluting with a suitable solvent at a concentration of 0.05 to 2 M. Such diluent solvent is not particularly limited as long as it is inert to the reaction and pyridine, THF, dichloromethane, water, and a combination of these can be mentioned. Of these, for example, iodine/water/pyridine-THF or iodine/pyridine-acetic acid, peroxidative agent (TBHP)/dichloromethane or tert-butyl hydroperoxide/nonane is preferably used.

The sulfurizing agent to be used in this step is not particularly limited as long as it has an ability to convert a phosphite triester bond to a thiophosphate triester bond, and 5-[(N,N-dimethylaminomethylidene)amino]-3H-1,2,4-dithiazole-3-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), 3-amino-1,2,4-dithiazole-5-thione (ADTT) and sulfur are preferable.

Since a good reaction proceeds, 5-[(N,N-dimethylaminomethylidene)amino]-3H-1,2,4-dithiazole-3-thione, 3H-1,2-benzodithiol-3-one-1,1-dioxide, 3H-1,2-benzodithiol-3-one, and phenylacetyl disulfide are more preferable, 5-[(N,N-dimethylaminomethylidene)amino]-3H-1,2,4-dithiazole- 3-thione and 3H-1,2-benzodithiol-3-one-1,1-dioxide are further preferable, and 5-[(N,N-dimethylaminomethylidene)amino]-3H-1,2,4-dithiazole-3-thione is particularly preferable. Such sulfurizing agent can be used by diluting with a suitable solvent at a concentration of 0.05 to 2 M. Such diluent solvent is not particularly limited as long as it is inert to the reaction and, for example, dichloromethane, acetonitrile, pyridine or a mixed solvent of any of these can be mentioned.

The amount of the oxidant or sulfurizing agent to be used is, for example 1 to 50 mol, preferably 1 to 5 mol, per 1 mol of the phosphite triester product (c).

The reaction temperature is not particularly limited as long as the reaction proceeds, and 0° C. to 100° C. is preferable, 20° C. to 50° C. is more preferable. The reaction time varies depending on the kind of the phosphite triester product (c), the kind of the oxidant or sulfurizing agent to be used, reaction temperature and the like and is, for example 1 min to 3 hr.

In the production method of the present invention in which step (4) (deprotection) is performed after step (3) (oxidation or sulfurization) without performing solid-liquid separation, the present inventors have found that when 5-[(N,N-dimethylaminomethylidene)amino]-3H-1,2,4-dithiazole-3-thione (DDTT) is used as the sulfurizing agent, a side reaction in which a decomposition product of DDTT is added to a 5'-hydroxy group during step (4) occurs, and the condensation reaction thereafter is inhibited. To solve this problem, the present inventors have conducted intensive studies and found that, when DDTT is used in step (3), the aforementioned side reaction can be suppressed by adding a mixture of a carboxylic acid and an organic base (neutralized salt), an inorganic acid or an amine to the reaction solution after step (1) and before step (4). Only one kind of the aforementioned carboxylic acid, organic base, inorganic acid and amine may be used or two or more kinds thereof may be used in combination.

The carboxylic acid in the aforementioned mixture is preferably a $C_{2-5}$ carboxylic acid optionally substituted by a halogen atom such as acetic acid, chloroacetic acid, dichloroacetic acid, trichloroacetic acid, fluoroacetic acid, difluoroacetic acid, trifluoroacetic acid, propionic acid, butyric acid, valeric acid or the like, more preferably a acetic acid optionally substituted by a halogen atom, further preferably acetic acid.

The organic base in the aforementioned mixture is preferably at least one selected from pyridines optionally substituted by 1 to 3 $C_{1-3}$ alkyl groups and imidazoles optionally substituted by 1 to 3 $C_{1-3}$ alkyl groups such as pyridine, 2,4,6-trimethylpyridine, imidazole, N-methylimidazole and the like, more preferably a pyridine optionally substituted by 1 to 3 $C_{1-3}$ alkyl groups, further preferably 2,4,6-trimethylpyridine.

In the aforementioned mixture, the amount of the organic base is preferably the same as or more than the amount of carboxylic acid. In the aforementioned mixture, the amount of the basic nitrogen atom of the organic base is more preferably 1 to 5 mol, further preferably 1 to 2 mol, particularly preferably 1 mol, per 1 mol of the carboxy group of carboxylic acid. When imidazole is used as the organic base, the 3-position nitrogen atom alone is counted as the basic nitrogen atom.

The amount of the aforementioned mixture to be used is determined based on the amount of carboxylic acid contained in the mixture (i.e., amount of neutralized salt). The amount of the carboxylic acid is preferably 1 to 10 mol, more preferably 1 to 5 mol, further preferably 1 to 3 mol, per 1 mol of the amount of DDTT to be used in step (3).

The aforementioned side reaction can also be suppressed by adding an inorganic acid instead of the aforementioned mixture of a carboxylic acid and an organic base (neutralized salt). Examples of the inorganic acid include hydrochloric acid, hydrofluoric acid, hydrobromic acid. Of these, hydrochloric acid and hydrofluoric acid are preferable, hydrochloric acid is more preferable. The amount of the inorganic acid to be used is preferably 1.0 to 20 mol, more preferably 1.5 to 10 mol, further preferably 2.0 to 5.0 mol, per 1 mol of the amount of DDTT to be used in step (3).

The aforementioned side reaction can also be suppressed by adding an amine instead of the aforementioned mixture of a carboxylic acid and an organic base (neutralized salt). Examples of the amine include aniline, 2-chloroaniline, 3-chloroaniline, 2,4-dichloroaniline, 2-fluoroaniline, 4-methoxyaniline, 4-nitroaniline, 2,6-dichloroaniline, 2,6-dimethylaniline. Of these, 2-chloroaniline and 2,6-dimethylaniline are preferable, 2,6-dimethylaniline is more preferable. The amount of the amine to be used is preferably 1.0 to 20 mol, more preferably 1.5 to 10 mol, further preferably 2.0 to 5.0 mol, per 1 mol of the amount of DDTT to be used in step (3).

Step (4) (Deprotection)

In this step, the temporary protecting group of the oligonucleotide (d) is removed with an acid to give an oligonucleotide (e) wherein the 5'-hydroxy group is not protected. Only one kind of acid may be used, or two or more kinds thereof may be used in combination.

The acid to be used in this step is not particularly limited as long as good deprotection can be achieved, and trifluoroacetic acid, dichloroacetic acid, trifluoromethanesulfonic acid, trichloroacetic acid, methanesulfonic acid, hydrochloric acid, acetic acid, p-toluenesulfonic acid or the like is preferably used. To achieve a good reaction, trifluoroacetic acid, dichloroacetic acid, trifluoromethanesulfonic acid, trichloroacetic acid are more preferable, trifluoroacetic acid, dichloroacetic acid, trifluoromethanesulfonic acid are further preferable, trifluoroacetic acid, trifluoromethanesulfonic acid are still further preferable, trifluoroacetic acid is particularly preferable. These acids may be diluted with the aforementioned non-polar solvents. When the aforementioned acid is used, a particular base may be combined to appropriately adjust the acidity and the mixture is used. The amount of the acid to be used in this step is, for example 1 to 100 mol, preferably 1 to 40 mol, per 1 mol of the oligonucleotide (d).

The reaction temperature in this step is not particularly limited as long as the reaction proceeds, and is preferably −10° C. to 50° C., more preferably 0° C. to 40° C. The reaction time varies depending on the oligonucleotide (d) used, the kind of acid, the kind of non-polar solvent, reaction temperature and the like, and it is, for example 5 min to 5 hr.

In this step, a cation scavenger is preferably used in or after the removal reaction of the temporary protecting group of the 5'-hydroxy group of the oligonucleotide (d). That is, the removal reaction of the temporary protecting group is preferably performed in the presence of a cation scavenger or a cation scavenger is preferably added to the reaction solution after the removal reaction of the temporary protecting group. Only one kind of the cation scavenger may be used, or two or more kinds thereof may be used in combination.

The cation scavenger is not particularly limited as long as re-protection (returning to material) by a temporary protecting group removed or a side reaction with the deprotected functional group does not proceed. A pyrrole derivative such as pyrrole, 2-methylpyrrole, 3-methylpyrrole, 2,3-dimethylpyrrole, 2,4-dimethylpyrrole or the like; an indole derivative such as indole, 3-methylindole, 4-methylindole, 5-methylindole, 6-methylindole, 7-methylindole, 5,6-dimethylindole, 6,7-dimethylindole or the like; a furan derivative such as 2-methylfuran, 2,3-dimethylfuran, 2-methyl-3-(methylthio)furan, menthofuran or the like can be used. Since a good cation trap effect can be obtained, pyrrole, 2-methylpyrrole, 3-methylpyrrole, 2,3-dimethylpyrrole, 2,4-dimethylpyrrole, indole, 3-methylindole, 4-methylindole, 5-methylindole, 6-methylindole, 7-methylindole, 5,6-dimethylindole, 6,7-dimethylindole, 2-methylfuran, 2,3-dimethylfuran, 2-methyl-3-(methylthio)furan, menthofuran are preferable, pyrrole, 3-methylpyrrole, 2,4-dimethylpyrrole, indole, 4-methylindole, 5-methylindole, 6-methylindole, 7-methylindole, 5,6-dimethylindole, 6,7-dimethylindole are more preferable, pyrrole, 3-methylpyrrole, indole are further preferable, pyrrole, indole are still further preferable, and pyrrole is particularly preferable. The amount of the cation scavenger to be used in this step is, for example 1 to 50 mol, preferably 5 to 20 mol per 1 mol of the oligonucleotide (d).

Step (5) (Neutralization)

To neutralize the acid used in step (4) after step (4) (deprotection), a base may be added to the reaction solution. However, in the production method of the present invention, step (6) (solid-liquid separation or extraction) and washing are performed as necessary after step (4), whereby the acid used in step (4) can be removed from the oligonucleotide (e). Therefore, step (5) is not essential.

In this step, only one kind of base may be used, or two or more kinds thereof may be used in combination. As the base to be used, an organic base is preferable. As the organic base, pyridine, 2,4,6-trimethylpyridine, benzimidazole, 1,2,4-triazole, N-phenylimidazole, 2-amino-4,6-dimethylpyrimidine, 1,10-phenanthrolin, imidazole, N-methylimidazole, 2-chlorobenzimidazole, 2-bromobenzimidazole, 2-methylimidazole, 2-phenylbenzimidazole, N-phenylbenzimidazole, 5-nitrobenzimidazole are preferable, pyridine, 2,4,6-trimethylpyridine, benzimidazole, 1,2,4-triazole, N-phenylimidazole, N-methylimidazole, 2-amino-4,6-dimethylpyrimidine, 1,10-phenanthrolin are more preferable, pyridine, 2,4,6-trimethylpyridine, benzimidazole, 1,2,4-triazole, N-phenylimidazole are further preferable, pyridine, 2,4,6-trimethylpyridine, benzimidazole, 1,2,4-triazole are particularly preferable, and pyridine, 2,4,6-trimethylpyridine, benzimidazole are most preferable.

The amount of the base to be used in this step is, for example 1 to 10 mol, preferably 1 to 3 mol, per 1 mol of the amount of the acid to be used in step (4).

Step (6) (Solid-Liquid Separation or Extraction)

In this step, a polar solvent is added to the reaction solution containing the oligonucleotide (e), or the oligonucleotide (e) is precipitated and purified (solid-liquid separation), or a polar solvent is added to the reaction solution to separate the layers between polar solvent and non-polar solvent, and the oligonucleotide (e) is transferred to the non-polar solvent layer and purified (extraction). In both solid-liquid separation and extraction, only one kind of the polar solvent may be used, or two or more kinds thereof may be used in combination.

The solid-liquid separation is explained. Examples of the polar solvent to be used in solid-liquid separation include alcohol solvents such as methanol, ethanol, isopropanol and the like; nitrile solvents such as acetonitrile, propionitrile and the like; ketone solvents such as acetone, 2-butanone and the like; polar ether solvents such as 1,4-dioxane, tetrahydrofuran and the like; amide solvents such as dimethylformamide, dimethylacetamide, N-methylpiperidone and the like, sulfoxide solvents such as dimethyl sulfoxide and the like; water, and the like, and a mixed solvent. Of these, nitrile solvents are preferable, and acetonitrile is more preferable.

To increase the collection rate of the oligonucleotide (e), the amount of the polar solvent to be added in the solid-liquid separation is preferably 1 to 20 mL, more preferably 1 to 10 mL, further preferably 1 to 5 mL, per 1 mL of the non-polar solvent contained in the reaction solution.

The polar solvent may contain water to minimize loss of the oligonucleotide (e) in a polar solvent. In this case, the content of water in the polar solvent is preferably 1 to 10% (v/v), more preferably 3 to 8% (v/v). When the content of water is too low, loss of the oligonucleotide (e) in the polar solvent may increase, and when the water content is too high, removal of impurity in a polar solvent tends to be insufficient.

To increase collection rate of the oligonucleotide (e), a precipitation promoter (e.g., 3,4,5-tris(octadecyloxy)benzyl 2,2-dimethylpropanoate) described in WO 2016/117663, which is incorporated herein by reference in its entirety, may also be used.

Extraction is explained now. While an extraction operation is not particularly limited, it preferably includes adding a polar solvent to the reaction solution containing the oligonucleotide (e) to separate the layers between polar solvent and non-polar solvent and transferring the oligonucleotide (e) to the non-polar solvent layer. By this extraction, impurities such as remaining materials, byproducts and the like can be transferred to the polar solvent layer and removed.

Examples of the polar solvent to be used for extraction include alcohol solvents such as methanol, ethanol, isopropanol and the like, nitrile solvents such as acetonitrile, propionitrile and the like, ketone solvents such as acetone, 2-butanone and the like, polar ether solvents such as 1,4-dioxane, tetrahydrofuran and the like, amide solvents such as N,N-dimethylformamide, N,N-dimethylacetamide, N-methylpiperidone and the like, sulfoxide solvents such as dimethyl sulfoxide and the like, water, and the like, and a mixed solvent of two or more kinds thereof. Of these, amide solvents, nitrile solvents, and combination of these are preferable, acetonitrile, N,N-dimethylformamide, N-methylpiperidone, and combination of these are more preferably used. Of these, nitrile solvents are preferable, and acetonitrile is more preferable.

The polar solvent used for extraction may contain water to improve separation ability from non-polar solvent. In this case, the content of water in the polar solvent is preferably 1 to 10% (v/v), more preferably 3 to 8% (v/v). When the water content is too low, the separation ability may not be improved much. When the water content is too high, solubility of impurity in a polar solvent decreases and the removal efficiency thereof tends to decrease.

For extraction, a non-polar solvent may be added as necessary to the reaction solution together with the polar solvent. Only one kind of non-polar solvent may be used, or two or more kinds thereof may be used in combination. As the non-polar solvent to be added as necessary, halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like can be mentioned. Of these, aromatic solvents, aliphatic solvents, or a combination of these is preferable, benzene, toluene, hexane, pentane, heptane, nonane, cyclohexane, a combination of these or the like is preferable, toluene, heptane, nonane or a combination of these is more preferable, toluene, heptane or a combination of these is further preferable, and heptane is particularly preferable.

After layer separation between polar solvent and non-polar solvent, impurity can be removed by an operation to remove the polar solvent layer. The amount of impurity may be further decreased by adding a polar solvent to the non-polar solvent layer after removal of the polar solvent layer, stirring the mixture to separate the layers, and performing an operation to remove the polar solvent.

The amount of the polar solvent to be used for one extraction operation is preferably 0.1 to 10 mL, more preferably 0.2 to 5 mL, further preferably 0.2 to 1 mL, per 1 mL of the non-polar solvent.

The Oligonucleotide (e) can be isolated by concentrating the obtained non-polar solvent layer.

Step (7) (Deprotection and Isolation)

The production method of the present invention may also include a step for removing all protecting groups of the oligonucleotide obtained after step (6) (solid-liquid separation or extraction), and isolating unprotected oligonucleotide. As a deprotection method, for example, all protecting groups of the oligonucleotide can be removed according to the deprotection method described in PROTECTIVE GROUPS IN ORGANIC SYNTHESIS, 3rd ed., JOHN WILLY&SONS (1999), which is incorporated herein by reference in its entirety, and the like. To be specific, anchor, and phenoxyacetyl group, acetyl group and the like, all of which are protecting groups of nucleic acid base; and cyanoethyl group and the like protecting a phosphoric acid skeleton can all be removed by a treatment with aqueous ammonia, aqueous ammonia/ethanol solution, or a mixture of aqueous ammonia and aqueous methylamine solution. In addition, 5' hydroxy-protecting group can be removed by a treatment with the acid used in step (4) or an appropriately diluted solution of such acid. Unprotected (i.e., without a protecting group) oligonucleotide is easily degraded by an enzyme, and therefore, unprotected oligonucleotide is preferably isolated under control of air cleanliness.

The progress of the reaction in each of the above-mentioned steps can be confirmed by a method similar to conventional liquid phase organic synthesis reaction. That is, the reaction can be traced by thin layer silica gel chromatography, high performance liquid chromatography or the like. 5'-3' Synthesis The production method of the present invention directed to 5'-3' synthesis includes the following steps (1'), (3'), (4') and (6'). The production method may further include the following steps (2'), (5') and (7') as necessary.

(1') condensing, in a non-polar solvent, a nucleoside, nucleotide or oligonucleotide (b') wherein a 5'-hydroxy group is phosphoramidited, a 3'-hydroxy group or 3'-amino group is protected by a temporary protecting group removable under acidic conditions, and other groups are optionally protected by a protecting group selected from protecting groups unremovable under acidic conditions but removable under basic conditions and protecting groups used for nucleic acid synthesis, and a nucleoside, nucleotide or oligonucleotide (a') wherein a 3'-hydroxy group or 3'-amino group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are optionally protected by a protecting group used for nucleic acid synthesis, or a substituted nucleotide or oligonucleotide ($\alpha'$) wherein a 3'-hydroxy group or 3'-amino group is not protected, one hydroxy group of a 5'-phosphoric acid group is replaced by —$OL^{n1}$-OH wherein $L^{n1}$ is an organic group, the hydroxy group of —$OL^{n1}$-OH is protected by a protecting group unremovable under acidic conditions but removable under basic conditions, and other groups are optionally protected by a protecting group used for nucleic acid synthesis by adding the nucleoside, nucleotide or oligonucleotide (b') to a reaction solution comprising the nucleoside, nucleotide or oligonucleotide (a') or the substituted nucleotide or oligonucleotide ($\alpha$) to give a reaction solution comprising a phosphite triester product (c') wherein the 3'-hydroxy group or 3'-amino group is protected by the temporary protecting group removable under acidic conditions;

(2') adding a quencher as necessary to the reaction solution after condensation;

(3') oxidizing or sulfurizing the phosphite triester product (c') by adding an oxidant or a sulfurizing agent to the reaction solution comprising the phosphite triester product (c') to give a reaction solution comprising an oligonucleotide (d') wherein the 3'-hydroxy group or 3'-amino group is protected by the temporary protecting group removable under acidic conditions;

(4') removing the temporary protecting group of the 3'-hydroxy group or 3'-amino group by adding an acid to the is reaction solution after the oxidation or sulfurization to give a reaction solution comprising an oligonucleotide (e') wherein the 3'-hydroxy group or 3'-amino group is not protected;

(5') neutralizing the reaction solution comprising the oligonucleotide (e) as necessary by adding a base;

(6') adding a polar solvent as necessary to the reaction solution comprising the oligonucleotide (e') and obtaining the precipitated oligonucleotide (e'); and (7') removing all protecting groups of the obtained oligonucleotide as necessary and isolating an unprotected oligonucleotide.

The oligonucleotide chain can be elongated by repeating the cycle of steps (1'), (3'), (4') and (6') (preferably steps (1')-(6')). The production method of oligonucleotide including steps (1'), (3') and (4') is encompassed in the present invention.

The explanation of the production method of the present invention directed to 5'-3' synthesis is basically the same as the explanation of the production method of the present invention directed to the aforementioned 3'-5' synthesis except that a nucleotide or oligonucleotide (a') or a substituted nucleotide or oligonucleotide ($\alpha'$), in each of which a 3'-hydroxy group or 3'-amino group is not protected, and a nucleoside, nucleotide or oligonucleotide (b') wherein a 5'-hydroxy group is phosphoramidited are used to produce an oligonucleotide (e') wherein a 3'-hydroxy group or 3'-amino group is not protected. In other words, the explanations of steps (1') to (7'), the nucleoside, nucleotide or oligonucleotide (a'), the substituted nucleotide or oligonucleotide ($\alpha'$), the nucleoside, nucleotide or oligonucleotide (b'), the phosphite triester product (c'), the oligonucleotide (d') and the oligonucleotide (e') are basically the same as those of the aforementioned steps (1) to (7), the nucleoside, nucleotide or oligonucleotide (a), the substituted nucleotide or oligonucleotide (α), the nucleoside, nucleotide or oligonucleotide (b), the phosphite triester product (c), the oligonucleotide (d) and the oligonucleotide (e) except that the protection embodiments of the 3'-hydroxy group or 3'-amino group and the 5'-hydroxy group and the like are exchanged. The differences in the 5'-3' synthesis from the 3'-5' synthesis are explained below Step (1') (Condensation)

The nucleoside, nucleotide or oligonucleotide (b') used in this step has a 3'-hydroxy group or 3'-amino group protected by a temporary protecting group removable under acidic conditions. The explanation of the temporary protecting group of hydroxy group is the same as that in step (1).

Examples of the temporary protecting group of amino group include trityl group, monomethoxytrityl group, dimethoxytrityl group and the like. Of these, trityl group and monomethoxytrityl group are preferable.

In a preferable embodiment of this step, a nucleoside, nucleotide or oligonucleotide (a') wherein a 3'-hydroxy group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are optionally protected by a protecting group used for nucleic acid synthesis, or a substituted nucleotide or oligonucleotide (α') wherein a 3'-hydroxy group is not protected, one hydroxy group of a 5'-phosphoric acid group is replaced by —O$L^{n1}$-OH wherein $L^{n1}$ is an organic group, the hydroxy group of —O$L^{n1}$-OH is protected by a protecting group unremovable under acidic conditions but removable under basic conditions, and other groups are optionally protected by a protecting group used for nucleic acid synthesis, and a nucleoside, nucleotide or oligonucleotide (b') wherein a 5'-hydroxy group is phosphoramidited, a 3'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are used.

In a more preferable embodiment of this step, a substituted nucleotide or oligonucleotide (α') wherein a 3'-hydroxy group is not protected, one hydroxy group of a 5'-phosphoric acid group is replaced by —O$L^{n1}$-OH wherein $L^{n1}$ is an organic group, the hydroxy group of —O$L^{n1}$-OH is protected by a protecting group unremovable under acidic conditions but removable under basic conditions, and other groups are optionally protected by a protecting group used for nucleic acid synthesis, and a nucleoside or oligonucleotide (b') wherein a 5'-hydroxy group is phosphoramidited, a 3'-hydroxy group is protected by a temporary protecting group removable under acidic conditions, and other groups are optionally protected by a protecting group selected from protecting groups unremovable under acidic conditions but removable under basic conditions and protecting groups used for nucleic acid synthesis are used.

In a more preferable another embodiment of this step, a nucleoside or oligonucleotide (a') wherein a 3'-hydroxy group is not protected, at least one group selected from an amino group and an imino group of a nucleic acid base, a 2'-hydroxy group and a 5'-hydroxy group of a ribose residue, and a 5'-hydroxy group of a deoxyribose residue is protected by a protecting group unremovable under acidic conditions but removable under basic conditions, and other groups are optionally protected by a protecting group used for nucleic acid synthesis, and a nucleoside or oligonucleotide (b') wherein a 5'-hydroxy group is phosphoramidited, a 3'-hydroxy group is protected by a temporary protecting group removable under acidic conditions, and other groups are optionally protected by a protecting group used for nucleic acid synthesis are used.

The condensation of the 3'-hydroxy group of the nucleoside, nucleotide or oligonucleotide (a') or substituted nucleotide or oligonucleotide (α') and the phosphoramidited 5'-hydroxy group of the nucleoside, nucleotide or oligonucleotide (b') can be performed as in step (1). Therefore, the explanation of the condensation in step (1') is the same as that in step (1) except that the "nucleoside, nucleotide or oligonucleotide (a) or substituted nucleotide or oligonucleotide (α)" is replaced by the "nucleoside, nucleotide or oligonucleotide (α') or substituted nucleotide or oligonucleotide (α')" and the "nucleoside, nucleotide or oligonucleotide (b)" is replaced by the "nucleoside, nucleotide or oligonucleotide (b')".

The condensation of the 3'-amino group of the nucleoside, nucleotide or oligonucleotide (a') or substituted nucleotide or oligonucleotide (α') and the phosphoramidited 5'-hydroxy group of the nucleoside, nucleotide or oligonucleotide (b') can also be performed as in step (1). Therefore, the explanation of the condensation in step (1') is the same as that in step (1) except that the "nucleoside, nucleotide or oligonucleotide (a) or substituted nucleotide or oligonucleotide (α)" is replaced by the "nucleoside, nucleotide or oligonucleotide (a') or substituted nucleotide or oligonucleotide (α')" and the "nucleoside, nucleotide or oligonucleotide (b)" is replaced by the "nucleoside, nucleotide or oligonucleotide (b')".

Examples of the nucleoside, nucleotide or oligonucleotide (a') include a compound represented by the following formula (a-I') (i.e., nucleoside or oligonucleotide).

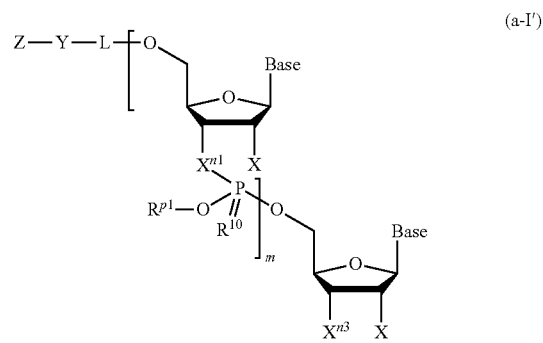

(a-I')

wherein m, Base in the number of m+1, X in the number of m+1, $R^{10}$ in the number of m, $R^{p1}$ in the number of m, L, Y and Z are each independently as defined above;

$X^{n1}$ in the number of m are each independently an oxygen atom or NH; and $X^{n3}$ is a hydroxy group or an amino group.

In the formula (a-I'), $X^{n1}$ in the number of m is preferably an oxygen atom.

In the formula (a-I'), $X^{n3}$ is preferably a hydroxy group.

In the formula (a-I'), $R^{p1}$ in the number of m are preferably each independently a group represented by —$CH_2CH_2WG$.

Explanations of other symbols in the formula (a-I') are as mentioned above.

Compound (a-I') is preferably a compound represented by the following formula (a-i') (definition and explanation of the symbols in the following formula are as mentioned above).

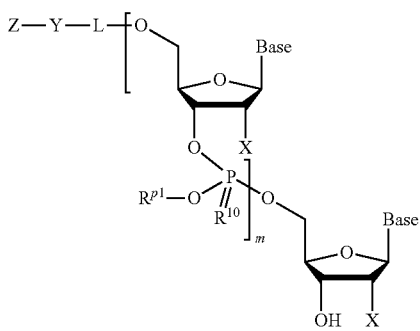
(a-i')

In compounds (a-i'), a compound represented by the formula (a-II') (i.e., nucleoside or oligonucleotide) is preferable (definition and explanation of the symbols in the following formula are as mentioned above).

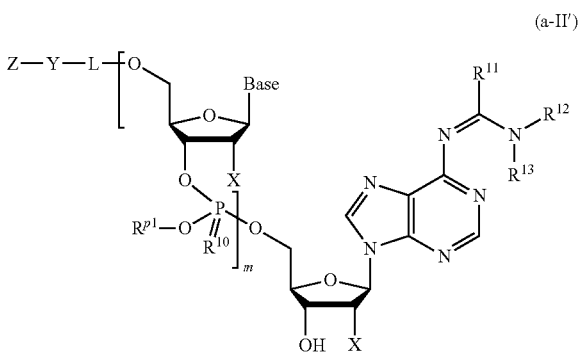
(a-II')

In the formula (a-II'), $R^{p1}$ in the number of m are preferably each independently a group represented by —$CH_2CH_2WG$.

In the formula (a-II'), m is preferably 0.

Explanations of other symbols in the formula (a-II') are as mentioned above.

In compounds (a-II'), a compound represented by the following formula (a-III') (i.e., nucleoside) is preferable (definition and explanation of the symbols in the following formula are as mentioned above).

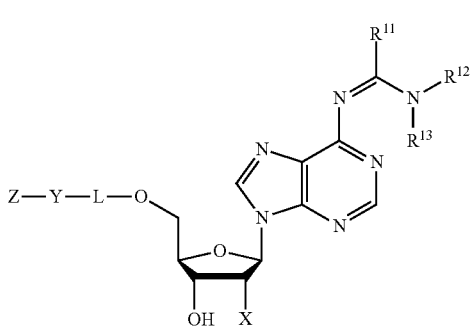
(a-III')

In compounds (a-I'), a compound represented by the following formula (a-IV') (i.e., nucleoside or oligonucleotide) is preferable (definition and explanation of the symbols in the following formula are as mentioned above).

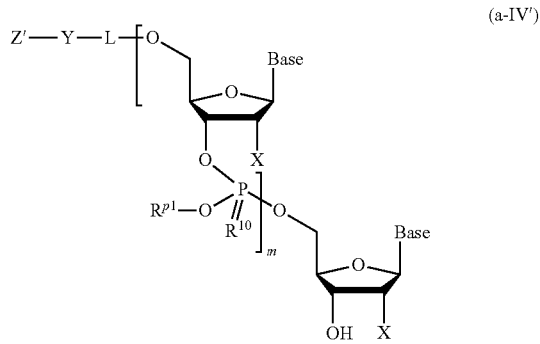
(a-IV')

In the formula (a-IV'), $R^{p1}$ in the number of m are preferably each independently a group represented by —$CH_2CH_2WG$.

In the formula (a-IV'), m is preferably 0. Explanations of other symbols in the formula (a-IV') are as mentioned above.

In compounds (a-IV'), a compound represented by the following formula (a-V') (i.e., nucleoside) is preferable (definition and explanation of the symbols in the following formula are as mentioned above).

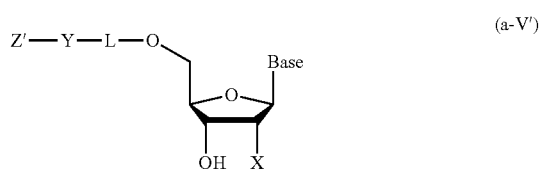
(a-V')

Examples of the nucleoside, nucleotide or oligonucleotide (a') include a compound represented by the following formula (a-VI') (i.e., nucleoside or oligonucleotide).

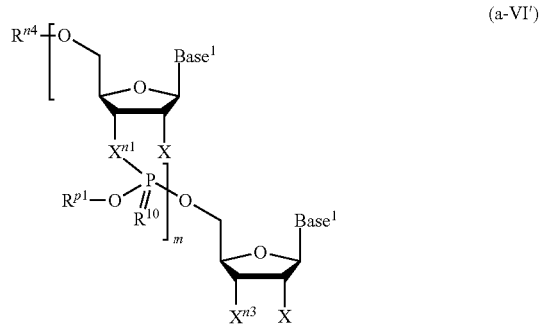
(a-VI')

wherein at least one of $Base^1$ in the number of m+1 is a nucleic acid base protected by -L-Y—Z, and the rest is an optionally protected nucleic acid base;

$X^{n1}$ in the number of m are each independently an oxygen atom or NH;

$X^{n3}$ is a hydroxy group or an amino group;

$R^{n4}$ is a hydroxy-protecting group;

m, X in the number of m+1, $R^{10}$ in the number of m, $R^{p1}$ in the number of m, L, Y and Z are each independently as defined above.

In the formula (a-VI'), $X^{n1}$ in the number of m are preferably oxygen atoms.

In the formula (a-VI'), $X^{n3}$ is preferably a hydroxy group.

In the formula (a-VI'), $R^{p1}$ in the number of m are preferably each independently a group represented by —CH$_2$CH$_2$WG.

In the formula (a-VI'), explanations of other symbols are as mentioned above.

Compound (a-VI') is preferably a compound represented by the following formula (a-vi') (definition and explanation of the symbols in the following formula are as mentioned above).

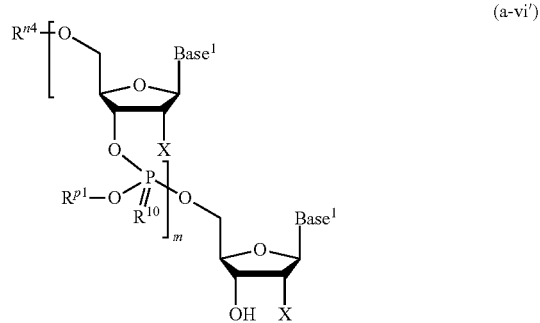

(a-vi')

Examples of the substituted nucleotide or oligonucleotide (α') include a compound represented by the following formula (a-VII').

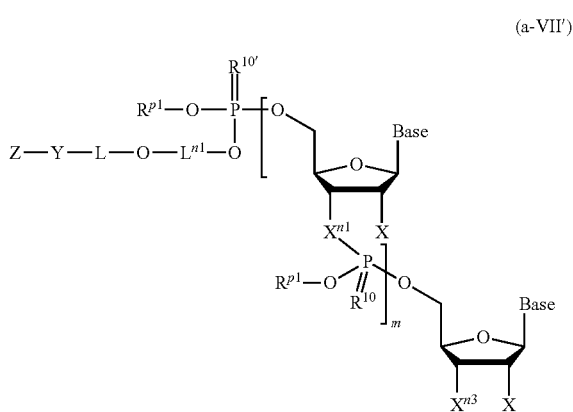

(a-VII')

wherein $X^{n1}$ in the number of m+1 are each independently an oxygen atom or NH;

$X^{n3}$ is a hydroxy group or an amino group;

$L^{n1}$ is an organic group;

m, Base in the number of m+1, X in the number of m+1, $R^{10}$ in the number of m+1, $R^{p1}$ in the number of m+1, L, Y and Z are each independently as defined above.

In the formula (a-VII'), $X^{n3}$ is preferably a hydroxy group.

In the formula (a-VII'), $R^{p1}$ in the number of m+1 are preferably each independently a group represented by —CH$_2$CH$_2$WG.

Explanations of other symbols in the formula (a-VII') are as mentioned above.

Compound (a-VII') is preferably a compound represented by the following formula (a-vii') (definition and explanation of the symbols in the following formula are as mentioned above).

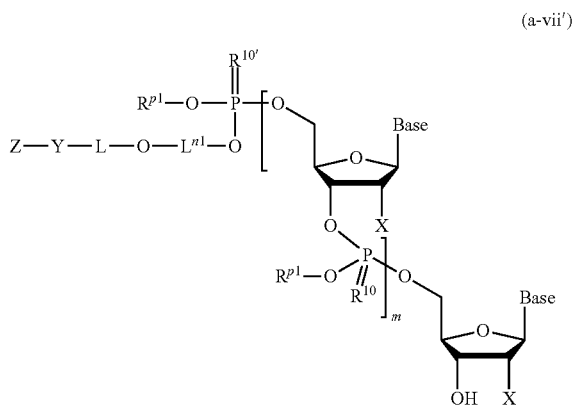

(a-vii')

The nucleoside, nucleotide or oligonucleotide (a') or substituted nucleotide or oligonucleotide (α') used in this step is preferably compound (a-I'), compound (a-VI') or compound (a-VII'), more preferably compound (a-i'), compound (a-vi') or compound (a-vii'), further preferably compound (a-i') or compound (a-vii'), particularly preferably compound (a-vii').

Examples of the nucleoside, nucleotide or oligonucleotide (b') include a compound represented by the following formula (b-I') (i.e., nucleoside or oligonucleotide).

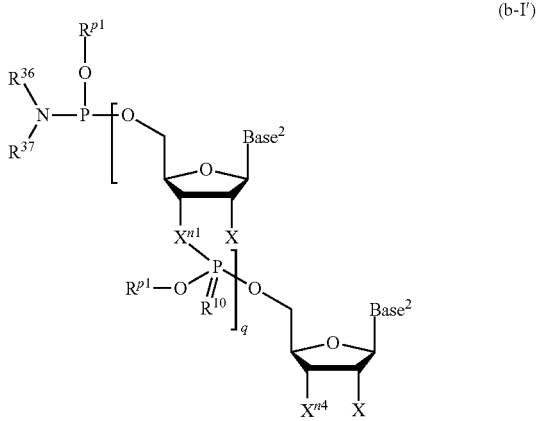

(b-I')

wherein

Base$^2$ in the number of q+1 are each independently a nucleic acid base optionally protected by a protecting group selected from -L-X—Z and protecting groups used for nucleic acid synthesis;

$X^{n1}$ in the number of are each independently an oxygen atom or NH;

$X^{n4}$ is a hydroxy group or an amino group, each of which is protected by a temporary protecting group removable under acidic conditions;

q, X in the number of q+1, $R^{p1}$ in the number of q+1, $R^{10}$ in the number of q, $R^{36}$, $R^{37}$ and Q" are each independently as defined above.

Explanations of the temporary protecting group of hydroxy group and the temporary protecting group of amino group in the formula (b-I') are as mentioned above. $X^{n4}$ is preferably a hydroxy group protected by a temporary protecting group removable under acidic conditions.

In the formula (b-I'), $R^{p1}$ in the number of q+1 are preferably each independently a group represented by —$CH_2CH_2WG$.

In the formula (b-I'), explanations of other symbols in are as mentioned above.

Compound (b-I') is preferably a compound represented by the following formula (b-i') (definition and explanation of the symbols in the following formula are as mentioned above).

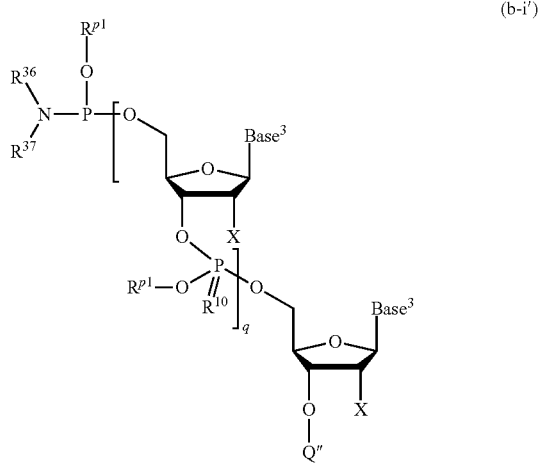

(b-i')

Explanations of the aforementioned compound (a-I')-compound (a-vii'), compounds (b-I') and (b-i') are basically the same as those of the aforementioned compound (a-I)-compound (a-vii), compounds (b-I) and (b-i) except that the protection embodiments the 3'-hydroxy group and the 5'-hydroxy group and the like are exchanged.

A combination of the nucleoside, nucleotide or oligonucleotide (a') or substituted nucleotide or the oligonucleotide (α'), and the nucleoside, nucleotide or oligonucleotide (b') used in this step is preferably a combination of compound (a-I'), compound (a-VI') or compound (a-VII') and compound (b-I'), more preferably a combination of compound (a-i'), compound (a-vi') or compound (a-vii') and compound (b-i'), further preferably a combination of compound (a-i') or compound (a-vii') and compound (b-i'), particularly preferably a combination of compound (a-vii') and compound (b-i').

Step (4') (Deprotection)

In this step, the temporary protecting group of the 3'-hydroxy group or 3'-amino group of the oligonucleotide (d') is removed with an acid to give an oligonucleotide (e') wherein the 3'-hydroxy group or 3'-amino group is not protected. Only one kind of acid may be used, or two or more kinds thereof may be used in combination.

Explanation of the removal of the temporary protecting group of hydroxy group is the same as that in step (1).

The acid to be used for removal of the temporary protecting group of amino group is not particularly limited as long as good deprotection can be achieved, and trifluoroacetic acid, dichloroacetic acid, trifluoromethanesulfonic acid, trichloroacetic acid, methanesulfonic acid, hydrochloric acid, acetic acid, p-toluenesulfonic acid or the like is preferably used. These acids may be diluted with the aforementioned non-polar solvents. The amount of the acid to be used for removal of the temporary protecting group of amino group is, for example 1 to 100 mol, preferably 1 to 40 mol, per 1 mol of the oligonucleotide (d'). The reaction temperature for removal of the temporary protecting group of amino group is not particularly limited as long as the reaction proceeds, and is preferably −10° C. to 50° C., more preferably 0° C. to 40° C. The reaction time of the temporary protecting group of amino group varies depending on the oligonucleotide (d') used, the kind of acid, the kind of non-polar solvent, reaction temperature and the like, and it is, for example 5 min to 5 hr.

Oligonucleotide

The oligonucleotide (e) or (e') obtained in step (6) or (6') (solid-liquid separation or extraction) or the unprotected oligonucleotide obtained in step (7) or (7') (deprotection and isolation) can also be led to a desired derivative by further applying an organic synthesis reaction. The oligonucleotide obtained by the production method of the present invention can be used for various applications such as pharmaceutical products (RNA, DNA, oligonucleic acid medicine etc.) for human or animal, functional food, food for specified health uses, food, chemical product, polymer material for living body or industrial use, and the like.

Nucleotide or Oligonucleotide

The present invention provides a compound represented by the following formula (I) (i.e., nucleotide or oligonucleotide) which is usable in the aforementioned step (1) or step (1').

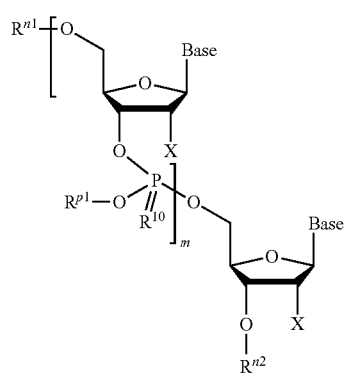

(I)

wherein m, Base in the number of m+1, X in the number of m+1, $R^{10}$ in the number of m, and $R^{p1}$ in the number of m are each independently as defined above; and one of $R^{n1}$ and $R^{n2}$ is a hydrogen atom, and the rest is a group represented by the formula (II) (definition of the symbols in the following formula are as mentioned above).

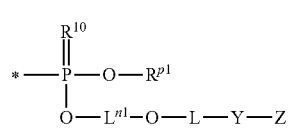

(II)

In the formula (I), $R^{n1}$ is preferably a group represented by the formula (II), and $R^{n2}$ is preferably a hydrogen atom.

In the formulas (I) and (II), $R^{p1}$ in the number of m+1 are preferably each independently a group represented by —CH$_2$CH$_2$WG.

In the formula (II), $L^{n1}$ is preferably a C$_{2-6}$ alkylene group, more preferably an ethylene group.

In the formula (I), m is preferably 0.

Explanations of other symbols in the formula (I) and the formula (II) are as mentioned above.

Compound (I) wherein $R^{n1}$ is a hydrogen atom and $R^{n2}$ is a group represented by the formula (II) corresponds to the aforementioned compound (a-vii). Compound (I) wherein $R^{n1}$ is a group represented by the formula (II) and $R^{n2}$ is a hydrogen atom corresponds to the aforementioned compound (a-vii').

An oligonucleotide obtained using compound (I) as a starting material has a modified phosphoric acid group at the 3'-position or 5'-position. It is known that an oligonucleotide thus modified acts to improve resistance to exonuclease (Bioorganic & Medicinal Chemistry 1997, 5, 2235-2243, which is incorporated herein by reference in its entirety).

Other features of the invention will become apparent in the course of the following descriptions of exemplary embodiments which are given for illustration of the invention and are not intended to be limiting thereof.

EXAMPLES

It is also possible to carry out the present invention by making appropriate modifications within the range that can conform to the above and the following gist, all of which are encompassed in the technical scope of the present invention.

The meanings of the abbreviations used in the below-mentioned Examples and the like are as described below.

In addition, rAOMe(Bz)-CE phosphoramidite and the like used in the below-mentioned Examples and the like are sometimes generically referred to as phosphoramidite monomer in the following.

The meanings of the abbreviations used in the below-mentioned Examples and the like are as described below.

DMTr: 4,4'-dimethoxytrityl
TOB: 3,4,5-tris(octadecyloxy)benzyloxy
SUC: succinyl
Ac-TOB: 3,4,5-tris(octadecyloxy)benzyl acetate
HO-dA-SUC-TOB: N$^6$-benzoyl-deoxyadenosin-3'-yl 3,4,5-tris(octadecyloxy)benzyl succinate
HO-dT-SUC-TOB: deoxythymidin-3'-yl 3,4,5-tris(octadecyloxy)benzyl succinate
HO-U-SUC-TOB: 2'-O-methyl-uridin-3'-yl 3,4,5-tris(octadecyloxy)benzyl succinate
MeOC(O)-TOB: methyl 3,4,5-tris(octadecyloxy)benzoate
HO—(CH$_2$)$_2$-SUC-TOB: 3,4,5-tris(octadecyloxy)benzyl 2-hydroxyethyl succinate
CSO: (1S)-(+)-(10-camphanylsulfonyl)oxaziridine
DBU: 1,8-diazabicyclo[5.4.0]-7-undecene
DDTT: 5-[(N,N-dimethylaminomethylidene)amino]-3H-1,2,4-dithiazole-3-thione
DPTT: dipentamethylenethiuram tetrasulfide
PADS: phenylacetyl disulfide
rA$_{OMe}$(Bz)-CE phosphoramidite: 5'-O-(4,4'-dimethoxytrityl)-N$^6$-benzoyl-2'-O-methyl-adenosine-3'-[O-(2-cyanoethyl)-(N,N-diisopropyl)]-phosphoramidite 2'-OMe-rA(Bz)-CE phosphoramidite: 5'-O-(4,4'-dimethoxytrityl)-N$^6$-benzoyl-2'-O-methyl-adenosine-3'-[O-(2-cyanoethyl)-(N,N-diisopropyl)]-phosphoramidite dG-CE phosphoramidite: 5'-O-(4,4'-dimethoxytrityl)-N$^2$-isobutyryl-deoxyadenosine-3'-[O-(2-cyanoethyl)-(N,N-diisopropyl)]-phosphoramidite dT-CE phosphoramidite: 5'-O-(4,4'-dimethoxytrityl)deoxythymidine-3'-[O-(2-cyanoethyl)-(N,N-diisopropyl)]-phosphoramidite U-CE phosphoramidite: 5'-O-(4,4'-dimethoxytrityl)-2'-O-methyl-uridine-3'-[O-(2-cyanoethyl)-(N,N-diisopropyl)]-phosphoramidite dT-5'-CE phosphoramidite: 3'-O-(4,4'-dimethoxytrityl)deoxythymidine-5'-[O-(2-cyanoethyl)-(N,N-diisopropyl)]-phosphoramidite Cm(Bz)-CE phosphoramidite: 5'-O-(4,4'-dimethoxytrityl)-N$^4$-benzoyl-2'-O-methyl-cytidine-3'-[O-(2-cyanoethyl)-(N,N-diisopropyl)]-phosphoramidite G$_{MOE}$(iBu)-CE phosphoramidite: 5'-O-(4,4'-dimethoxytrityl)-N$^2$-isobutyryl-2'-O-methoxyethyl-guanosine-3'-[O-(2-cyanoethyl)-(N,N-diisopropyl)]-phosphoramidite A$_{MOE}$(BZ)-CE phosphoramidite: 5'-O-(4,4'-dimethoxytrityl)-N$^6$-benzoyl-2'-O-methoxyethyl-adenosine-3'-[O-(2-cyanoethyl)-(N,N-diisopropyl)]-phosphoramidite T$_{MOE}$-CE phosphoramidite: 5'-O-(4,4'-dimethoxytrityl)-2'-O-methoxyethyl-thymidine-3'-[O-(2-cyanoethyl)-(N,N-diisopropyl)]-phosphoramidite 2'F-U-CE phosphoramidite: 5'-O-(4,4'-dimethoxytrityl)-2'-fluoro-uridine-3'-[O-(2-cyanoethyl)-(N,N-diisopropyl)]-phosphoramidite 2'F-G-CE phosphoramidite: 5'-O-(4,4'-dimethoxytrityl)-N$^2$-isobutyryl-2'-fluoro-guanosine-3'-[O-(2-cyanoethyl)-(N,N-diisopropyl)]-phosphoramidite N$^4$-benzoyl-5-Me-dC-CE phosphoramidite: 5'-O-(4,4'-dimethoxytrityl)-N$^4$-benzoyl-2'-deoxy-5-methylcytidine-3'-[O-(2-cyanoethyl)-(N,N-diisopropyl)]-phosphoramidite Example 1: Synthesis of phosphorothioate dimer (2'-O-methyl-uridine-3'-[O-(2-cyanoethyl)]phosphorothionyl 2'-O-methyl-uridin-3'-yl-[3,4,5-tris(octadecyloxy)benzyl]succinate)

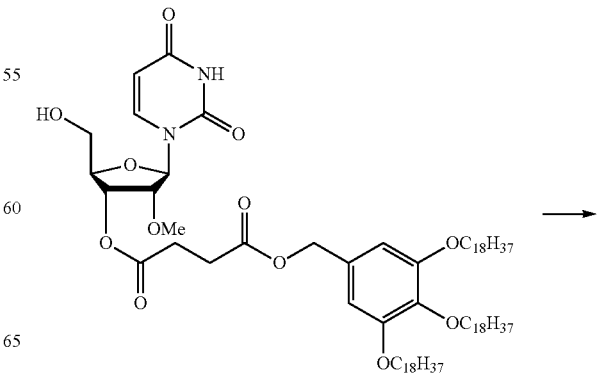

-continued

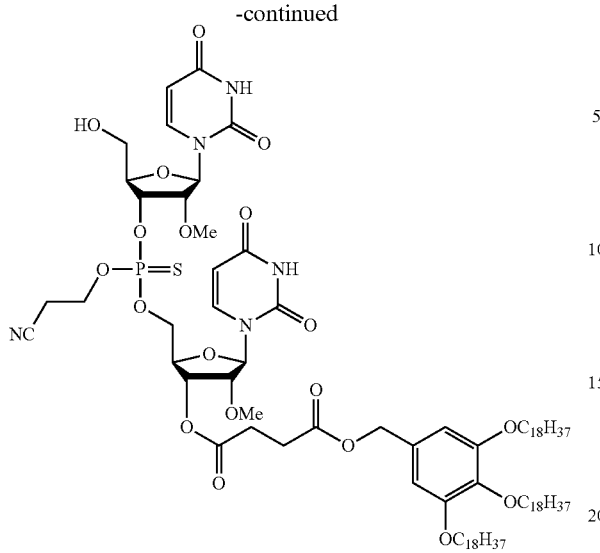

Under an argon atmosphere, in a 10 mL Schlenk tube were placed HO-U-SUC-TOB (82.2 mg, 66.0 μmol) and MeOC(O)-TOB (100 mg, 106 μmol) and they were dissolved in dehydrated dichloromethane (3.0 mL). To the obtained solution was added a mixed solution of 5-benzyl-thio-1H-tetrazole (37.8 mg, 197 μmol) and U-CE phosphoramidite (150 mg, 197 μmol) prepared by dissolving in dehydrated acetonitrile (0.5 mL), and the mixture was stirred at room temperature for 1 hr. To the reaction solution was added 2,2,2-trifluoroethanol (70.3 μL, 983 μmol), and the mixture was stirred at room temperature for 15 min. After stirring, PADS (178 mg, 590 μmol) was added and the mixture was stirred at room temperature for 2 hr. 5-Methoxyindole (193 mg, 1.31 mmol) and trifluoroacetic acid (45.2 μL, 590 μmol) were successively added, and the mixture was stirred at room temperature for 1.5 hr. Furthermore, 2,4,6-trimethylpyridine (85.5 μL, 649 μmol) was added, acetonitrile (10 mL) was added to the reaction solution, and the precipitated solid was collected by suction filtration using a KIRIYAMA ROHTO and dried to give a dimer (2'-O-methyl-uridine-3'-[O-(2-cyanoethyl)]phosphorothionyl 2'-O-methyl-uridin-3'-yl-[3,4,5-tris(octadecyloxy)benzyl]succinate) as a white solid (197 mg, yield 95%).

Example 2: Continuous synthesis of phosphorothioate 20-mer (SEQ ID NO: 1: 5'-TCCCGCCTGTGACATGCATT-3') in liquid (1) Synthesis of Phosphorothioate Dimer Wherein 3'-Hydroxy Group is Protected by Anchor

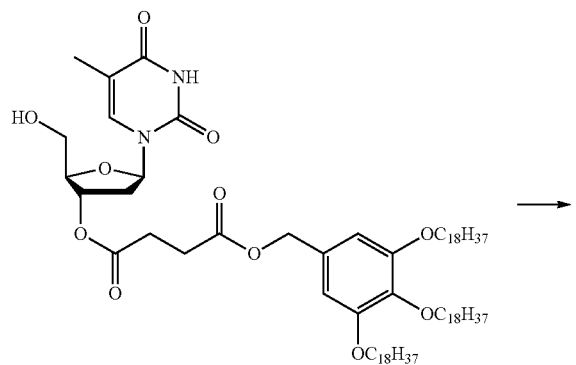

-continued

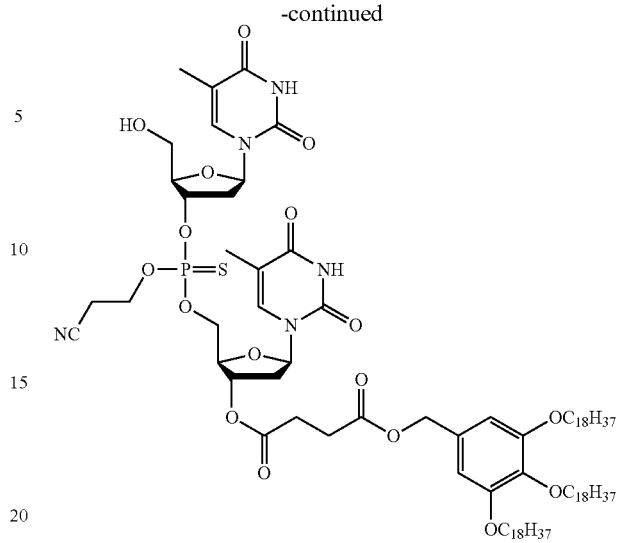

Under an argon atmosphere, in a 200 mL four-necked flask were placed HO-dT-SUC-TOB (619 mg, 0.500 mmol) and AcO-TOB (773 mg, 0.808 mmol) and they were dissolved in dehydrated dichloromethane (25 mL). To the obtained solution was added a mixed solution of 5-benzyl-thio-1H-tetrazole (288 mg, 1.50 mmol) and dT-CE phosphoramidite (1.12 g, 1.50 mmol) prepared by dissolving in dehydrated acetonitrile (2.0 mL), and the mixture was stirred at room temperature for 1.5 hr. To the reaction solution was added 2,2,2-trifluoroethanol (1.07 mL, 15.0 mmol), and the mixture was stirred at room temperature for 15 min. After stirring, a mixture of acetic acid (172 μL, 3.00 mmol) and 2,4,6-trimethylpyridine (594 μL, 4.50 mmol) was further added, and the mixture was stirred for 15 min at room temperature. DDTT (340 mg, 1.65 mmol) was added, and the mixture was stirred at room temperature for 30 min. After stirring, 5-methoxyindole (1.47 g, 10.0 mmol) and trifluoroacetic acid (689 μL, 9.00 mmol) were successively added, and the mixture was stirred at room temperature for 1.5 hr. Furthermore, 2,4,6-trimethylpyridine (1.31 mL, 9.90 mmol) was added, acetonitrile (150 mL) was added to the reaction solution and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (789 mg, yield 98%).

(2) Synthesis of Phosphorothioate 19-Mer Wherein 3'-Hydroxy Group is Protected by Anchor An operation similar to that in the above-mentioned (1) was further repeated 18 times to give a 19-mer (deoxycytidine 3'-[O-(2-cyanoethyl)]phosphorothionyl-$N^4$-benzoyl-deoxycytidine 3'-[O-(2-cyanoethyl)]phosphorothionyl-$N^4$-(2-hexyl)decanoyl-deoxycytidine 3'-[O-(2-cyanoethyl)]phosphorothionyl-$N^2$-isobutyryl-deoxyguanosine 3'-[O-(2-cyanoethyl)]phosphorothionyl-$N^4$-benzoyl-deoxycytidine 3'-[O-(2-cyanoethyl)]phosphorothionyl-$N^4$-(2-hexyl)decanoyl-deoxycytidine 3'-[O-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-N⁴-(2-hexyl)decanoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) (2.78 g).

(3) Synthesis of Phosphorothioate 20-Mer Wherein 3'-Hydroxy Group is Protected by Anchor and 5'-Hydroxy Group is Protected by DMTr Group Under an argon atmosphere, in a 200 mL four-necked flask was placed the 19-mer (2.78 g) obtained in the above-mentioned (2), and it was dissolved in dehydrated dichloromethane (25 mL). To the obtained solution was added a mixed solution of 5-benzylthio-1H-tetrazole (287 mg, 1.49 mmol) and dT-CE phosphoramidite (1.11 g, 1.49 mmol) prepared by dissolving in dehydrated acetonitrile (2.0 mL), and the mixture was stirred at room temperature for 1.5 hr. DDTT (338 mg, 1.64 mmol) was added, and the mixture was stirred at room temperature for 30 min. After stirring, acetonitrile (150 mL) was added to the reaction solution and the precipitated solid was collected by suction filtration using a KIRIYAMA ROHTO and dried to give a 20-mer (5'-O-(4,4'-dimethoxytrityl)-deoxythymidine 3'-[O-(2-cyanoethyl)]phosphorothionyl-N⁴-acetyl-deoxycytidine 3'-[O-(2-cyanoethyl)]phosphorothionyl-N⁴-acetyl-deoxycytidine 3'-[O-(2-cyanoethyl)]phosphorothionyl-N⁴-(2-hexyl)decanoyl-deoxycytidine 3'-[O-(2-cyanoethyl)]phosphorothionyl-N²-isobutyryl-deoxyguanosine 3'-[O-(2-cyanoethyl)]phosphorothionyl-N⁴-acetyl-deoxycytidine 3'-[O-(2-cyanoethyl)]phosphorothionyl-N⁴-(2-hexyl)decanoyl-deoxycytidine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-N⁶-benzoyl-deoxyadenosine 3'-[O-(2-cyanoethyl)]phosphorothionyl-N⁴-(2-hexyl)decanoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'[O-(2-cyanoethyl)]phosphorothionyl-N²-isobutyryl-deoxyguanosine 3'-[O-(2-cyanoethyl)]phosphorothionyl-N⁴-(2-hexyl)decanoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) as a white solid (2.79 g).

(4) Removal of DMTr Group

Under an argon atmosphere, in a 100 mL two-necked flask was placed the 20-mer (1.00 g) obtained in the above-mentioned (3) and it was dissolved in dehydrated dichloromethane (10 m). 5-Methoxyindole (245 mg, 1.66 mmol) and trifluoroacetic acid (100 µL, 1.31 mmol) were added and the mixture was stirred at room temperature for 1.5 hr, and neutralized with 2,4,6-trimethylpyridine (190 µL, 1.44 mmol). Acetonitrile (150 mL) was added, and the precipitated solid was collected by suction filtration using a KIRIYAMA ROHTO and dried to give a 20-mer wherein the DMTr group was removed (deoxythymidine 3'-[O-(2-cyanoethyl)]phosphorothionyl-N⁴-acetyl-deoxycytidine 3'-[O-(2-cyanoethyl)]phosphorothionyl-N⁴-acetyl-deoxycytidine 3'-[O-(2-cyanoethyl)]phosphorothionyl-N⁴-(2-hexyl)decanoyl-deoxycytidine 3'-[O-(2-cyanoethyl)]phosphorothionyl-N²-isobutyryl-deoxyguanosine 3'-[O-(2-cyanoethyl)]phosphorothionyl-N⁴-acetyl-deoxycytidine 3'-[O-(2-cyanoethyl)]phosphorothionyl-N⁴-(2-hexyl)decanoyl-deoxycytidine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-deoxythymidine 3'-(2-cyanoethyl)]phosphorothionyl-N²-isobutyryl-deoxyguanosine 3'-[O-(2-cyanoethyl)]phosphorothionyl-N⁶-benzoyl-deoxyadenosine 3'-[O-(2-cyanoethyl)]phosphorothionyl-N⁴-(2-hexyl)decanoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-N⁴-(2-hexyl)decanoyl-deoxycytidine 3'-(2-cyanoethyl)]phosphorothionyl-N⁶-benzoyl-deoxyadenosine 3'-[O-(2-cyanoethyl)]phosphorothionyl-deoxythymidine 3'-(2-cyanoethyl)]phosphorothionyl-deoxythymidin-3'-yl 3,4,5-tris(octadecyloxy)benzyl succinate) as a white solid (867 mg).

(5) Deprotection

A mixture of the 20-mer (20 mg) obtained in the above-mentioned (4) and 30 wt % aqueous ammonia (5.00 mL) was placed in an autoclave and heated at 55° C. for 16 hr and cooled to room temperature. Insoluble material in the reaction solution was removed by a syringe filter (Whatman 25 mm GD/X PVDF 0.45 µm) and the filtrate was freeze-dried to give the object deoxythymidine-3'-phosphorothionyl-deoxycytidine-3'-phosphorothionyl-deoxycytidine-3'-phosphorothionyl-deoxycytidine-3'-phosphorothionyl-deoxyguanosine-3'-phosphorothionyl-deoxycytidine-3'-phosphorothionyl-deoxycytidine-3'-phosphorothionyl-deoxythymidine-3'-phosphorothionyl-deoxyguanosine-3'-phosphorothionyl-deoxythymidine-3'-phosphorothionyl-deoxyguanosine-3'-phosphorothionyl-deoxyadenosine-3'-phosphorothionyl-deoxycytidine-3'-phosphorothionyl-deoxyadenosine-3'-phosphorothionyl-deoxythymidine-3'-phosphorothionyl-deoxyguanosine-3'-phosphorothionyl-deoxycytidine-3'-phosphorothionyl-deoxyadenosine-3'-phosphorothionyl-deoxythymidine-3'-phosphorothionyl-deoxythymidine.

HPLC (WATERS XBridge™ C18 2.5 µm 4.6×75 mm column, flow rate 1.0 mL/min, 8 mM TEA+100 mM HFIP, MeOH, gradient: 0-10 min; 5 to 60%, λ=260 nm):Rt=6.87 min (83.3 area %); TOF/MS: 6646.05

Example 3: Continuous Synthesis in Liquid without Neutralization of Acid (Step (5)) after Deprotection (1) Synthesis of Phosphorothioate Dimer Wherein 3'-Hydroxy Group is Protected by Anchor Under an argon atmosphere, in a 10 mL Schlenk tube were placed HO-dT-SUC-TOB (100 mg, 81 µmol) and MeOC(O)-TOB (100 mg, 106 µmol), and they were dissolved in dehydrated dichloromethane (4.0 mL). To the obtained solution was added a mixed solution of 5-benzylthio-1H-tetrazole (46.6 mg, 242 µmol) and dT-CE phosphoramidite (181 mg, 242 µmol) prepared by dissolving in dehydrated acetonitrile (0.5 mL), and the mixture was stirred at room temperature for 1.5 hr. To the reaction solution was added 2,2,2-trifluoroethanol (86.6 µL, 1.21 mmol), and the mixture was stirred at room temperature for 15 min. Furthermore, a mixture of acetic acid (13.9 µL, 242 µmol) and 2,4,6-trimethylpyridine (31.9 µL, 242 µmol), and DDTT (54.7 mg, 267 µmol) were added, and the mixture was stirred at room temperature for 30 min. After stirring, 5-methoxyindole (238 mg, 1.62 mmol) and trifluoroacetic acid (55.7 µL, 727 µmol) were successively added, and the mixture was stirred at room temperature for 1.5 hr. To the reaction solution was added acetonitrile (10 mL), and the precipitated solid was collected by suction filtration using a KIRIYAMA ROHTO while washing with acetonitrile (20 mL) and dried under reduced pressure to give a dimer (deoxythymidine-3'-[O-(2-cyanoethyl)]phosphorothionyl deoxythymidin-3'-yl-[3,4,5-tris(octadecyloxy)benzyl]succinate) as a white solid (222 mg, yield 96%).

(2) Synthesis of Phosphorothioate Trimer Wherein 3'-Hydroxy Group is Protected by Anchor An operation similar to that in the above-mentioned (1) was further repeated once to give a trimer ($N^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl3,4,5-tris(octadecyloxy)benzyl succinate) (251 mg, yield 89%).

Example 4: Synthesis of Phosphorothioate Dimer thermore, DPTT (28.0 mg, 73.0 µmol) was added, and the mixture was stirred at room temperature for 30 min. After stirring, 5-methoxyindole (234 mg, 1.62 mmol) and trifluoroacetic acid (55.7 µL, 727 µmol) were successively added, and the mixture was stirred at room temperature for 1.5 hr. The reaction solution was neutralized with 2,4,6-trimethylpyridine (105 µL, 800 µmol), triethyl phosphite (8.6 µL, 73.0 µmol) was added and the mixture was stirred at room temperature for 15 min. After stirring, acetonitrile (10 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (222 mg, yield 88%).

Example 5: Synthesis of Phosphorothioate Dimer

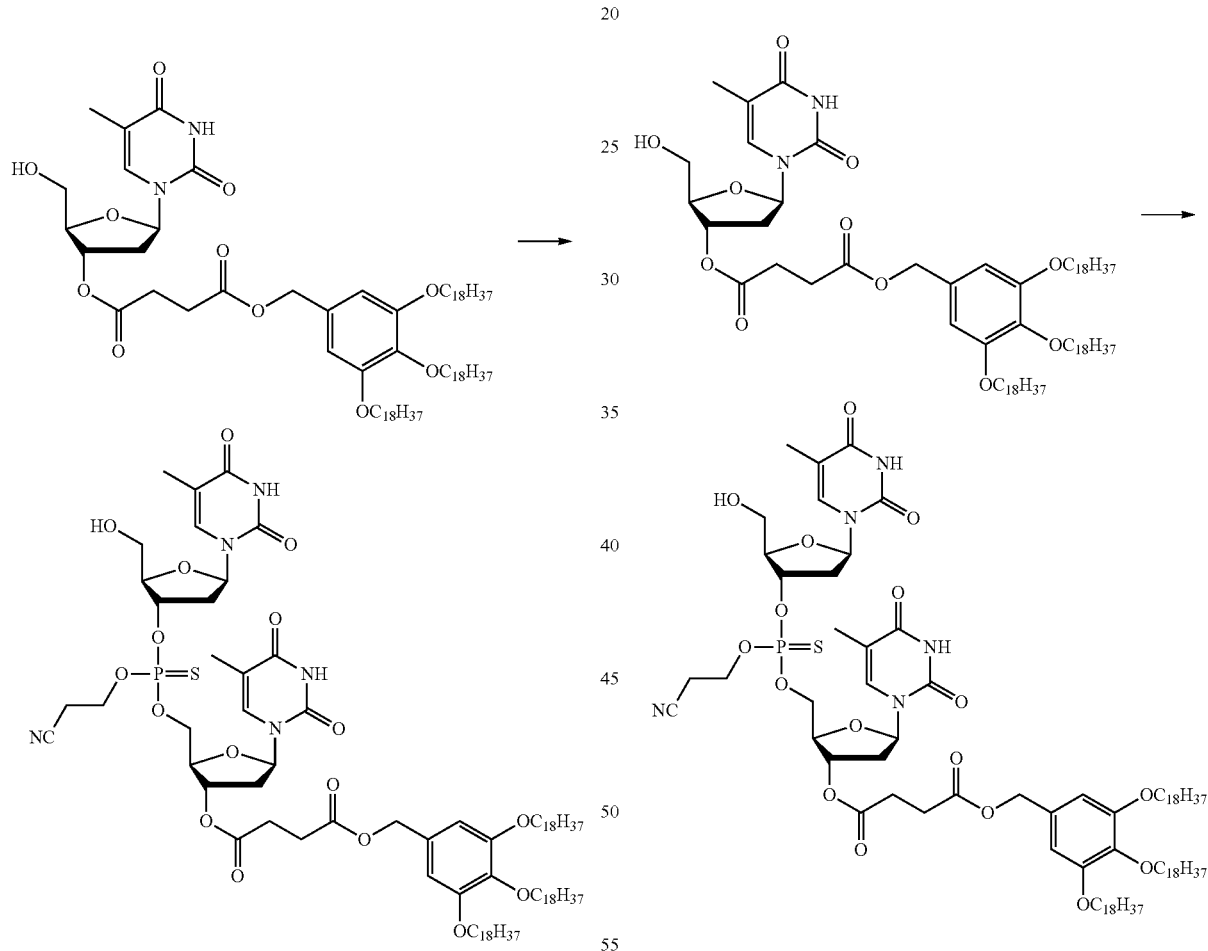

Under an argon atmosphere, in a 10 mL Schlenk tube were placed HO-dT-SUC-TOB (100 mg, 81 µmol) and MeOC(O)-TOB (100 mg, 106 µmol), and they were dissolved in dehydrated dichloromethane (5.0 mL). To the obtained solution was added a mixed solution of 5-benzylthio-1H-tetrazole (46.6 mg, 242 µmol) and dT-CE phosphoramidite (181 mg, 242 µmol) prepared by dissolving in dehydrated acetonitrile (0.5 mL), and the mixture was stirred at room temperature for 1.5 hr. To the reaction solution was added 2,2,2-trifluoroethanol (86.6 µL, 1.21 mmol), and the mixture was stirred at room temperature for 15 min. Fur- Under an argon atmosphere, in a 10 mL Schlenk tube were placed HO-dT-SUC-TOB (80.3 mg, 65.0 µmol) and MeOC(O)-TOB (99.0 mg, 105 µmol) and they were dissolved in dehydrated dichloromethane (3.0 mL). To the obtained solution was added a mixed solution of 5-benzylthio-1H-tetrazole (37.4 mg, 195 µmol) and dT-CE phosphoramidite (145 mg, 195 µmol) prepared by dissolving in dehydrated acetonitrile (0.5 mL), and the mixture was stirred at room temperature for 1.5 hr. To the reaction solution was added 2,2,2-trifluoroethanol (69.5 µmL, 973 µmol), and the mixture was stirred at room temperature for 15 min. Furthermore, PADS (177 mg, 584 µmol) was added, and the mixture was stirred at room temperature for 30 min. After stirring, 5-methoxyindole (191 mg, 1.30 mmol) and trifluoroacetic acid (44.7 µL, 584 µmol) were successively added, and the mixture was stirred at room temperature for 1.5 hr. The reaction solution was neutralized with 2,4,6-trimethylpyridine (84.6 µL, 642 µml). Acetonitrile (10 mL) was added, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (73.3 mg, 85%).
TOF/MS: 1557.0116

Example 6: Synthesis of Phosphorothioate Dimer

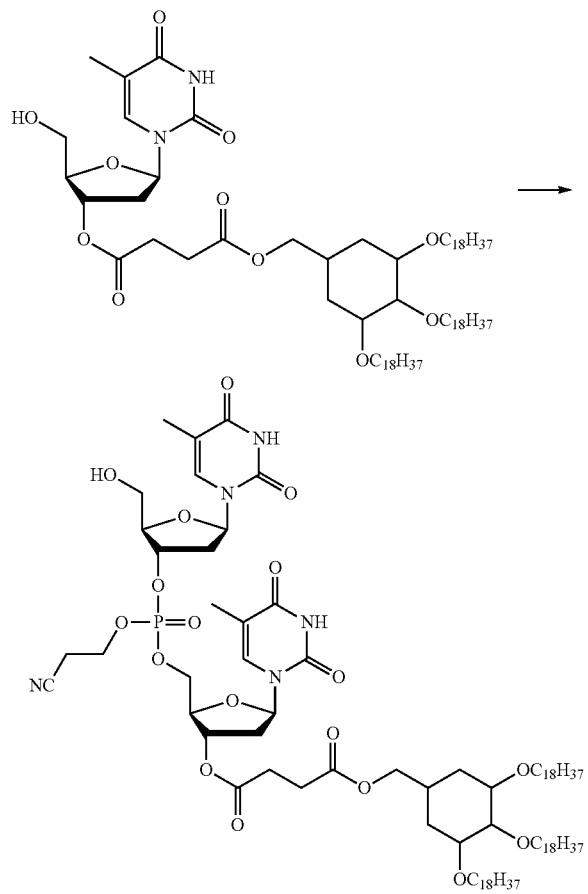

Under an argon atmosphere, in a 10 mL Schlenk tube were placed deoxythymidin-3'-yl-[3,4,5-tris(octadecyloxy)cyclohexyl-1-methyl]succinate (500 mg, 0.402 mmol) and methyl 3,4,5-tris(octadecyloxy)cyclohexyl-1-carboxylate (500 mg, 0.528 mmol), and they were dissolved in dehydrated dichloromethane (4.0 mL). To the obtained solution was added a mixed solution of 5-benzylthio-1H-tetrazole (116 mg, 0.603 mmol) and dT-CE phosphoramidite (449 mg, 0.603 mmol) prepared by dissolving in dehydrated acetonitrile (0.4 mL), and the mixture was stirred at room temperature for 1.5 hr. To the reaction solution was added 2,2,2-trifluoroethanol (129 µL, 1.81 mmol), and the mixture was stirred at room temperature for 15 min. Furthermore, DPTT (54.1 mg, 0.141 mmol) was added, and the mixture was stirred at room temperature for 30 min. After stirring, 5-methoxyindole (1.18 g, 8.04 mmol) and trifluoroacetic acid (115 µL, 1.51 mmol) were successively added, and the mixture was stirred at room temperature for 1.5 hr. The reaction solution was neutralized with 2,4,6-trimethylpyridine (218 µL, 1.66 mmol), acetonitrile (20 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)cyclohexyl-1-methyl]succinate) as a white solid (1.15 g, yield 100%).

Example 7: Synthesis of phosphorothioate dinucleotide

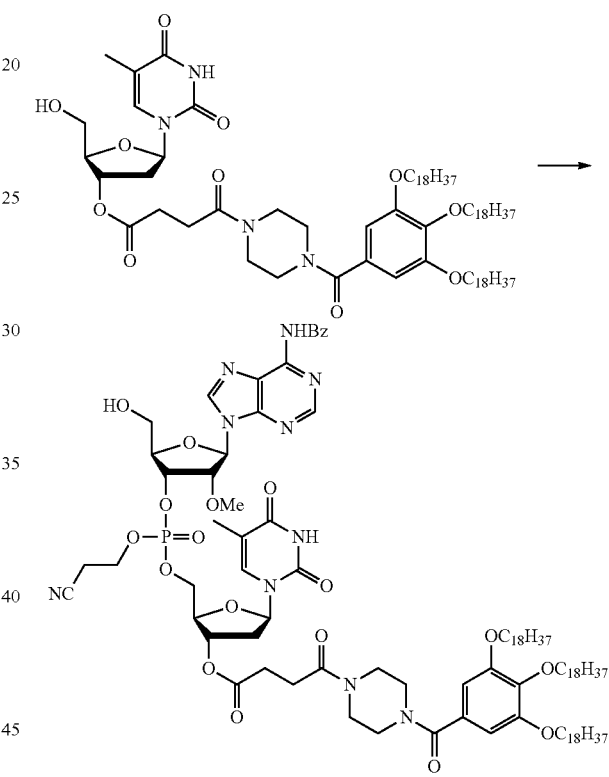

Under an argon atmosphere, in a 10 mL Schlenk tube were placed deoxythymidin-3'-yl-[3,4,5-tris(octadecyloxy)benzoylpiperazine]succinate (100 mg, 76.0 µmmol) and methyl 3,4,5-tris(octadecyloxy)cyclohexyl-1-carboxylate (100 mg, 0.106 mmol) and they were dissolved in dehydrated dichloromethane (3.0 mL). To the obtained solution was added a mixed solution of 5-benzylthio-1H-tetrazole (43.7 mg, 227 µmop and 2'-OMe-rA(Bz)-CE phosphoramidite (202 mg, 0.227 mmol) prepared by dissolving in dehydrated acetonitrile (0.3 mL), and the mixture was stirred at room temperature for 1.5 hr. To the reaction solution was added morpholine (99.0 µL, 1.14 mmol), and the mixture was stirred at room temperature for 15 min. Furthermore, (2R,8aS)-(+)-(camphorylsulfonyl)oxaziridine (54.7 mg, 0.239 mmol) was added, and the mixture was stirred at room temperature for 1 hr. 5-Methoxyindole (223 mg, 1.52 mmol) and trifluoroacetic acid (34.8 µt, 0.455 mmol) were successively added, and the mixture was stirred at room temperature for 1.5 hr. The reaction solution was neutralized with 2,4,6-trimethylpyridine (65.9 μL, 500 μmol), acetonitrile (10 mL) was added to the reaction solution, and the precipitated solid was collected by suction filtration using a KIRIYAMA ROHTO and dried to give a dimer (N$^6$-benzoyl-2'-O-methyl-adenosine-3'-[O-(2-cyanoethyl)]phosphoryl deoxy-thymidin-3'-yl-[3,4,5-tris(octadecyloxy)benzoylpiperazine] succinate) as a white solid (214 mg, yield 89%).

Example 8: Synthesis of Dinucleotide

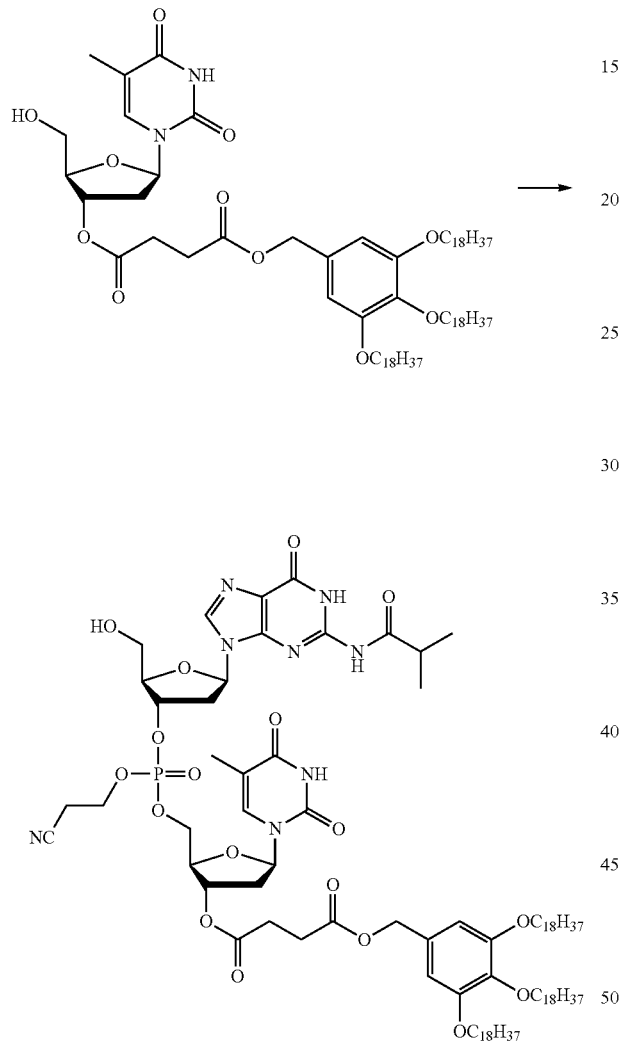

Under an argon atmosphere, in a 10 mL Schlenk tube were placed 3,4,5-tris(octadecyloxy)benzyl]succinate (100 mg, 81.0 μmmol) and methyl 3,4,5-tris(octadecyloxy)phenyl-1-carboxylate (100 mg, 0.106 mmol), and they were dissolved in dehydrated dichloromethane (5.0 mL). To the obtained solution was added a mixed solution of 5-benzyl-thio-1H-tetrazole (46.6 mg, 242 μmol) and dG-CE phosphoramidite (204 mg, 0.242 mmol) prepared by dissolving in dehydrated acetonitrile (0.5 mL), and the mixture was stirred at room temperature for 1.5 hr. To the reaction solution was added morpholine (106 μL, 1.21 mmol), and the mixture was stirred at room temperature for 15 min. Furthermore, a mixed solution of iodine (64.6 mg, 0.254 mmol), 2,4,6-trimethylpyridine (83.8 μL, 0.636 mmol) and water (6.60 μL, 0.364 mmol) was added, and the mixture was stirred at room temperature for 1 hr. 5-Methoxyindole (238 mg, 1.62 mmol) and trifluoroacetic acid (55.7 μL, 0.727 mmol) were successively added, and the mixture was stirred at room temperature for 1.5 hr. The reaction solution was neutralized with 2,4,6-trimethylpyridine (105 μL, 800 μmol), acetonitrile (10 mL) was added to the reaction solution, and the precipitated solid was collected by suction filtration using a KIRIYAMA ROHTO and dried to give dinucleotide (N$^2$-isobutyryl-deoxyadenosine-3'-[O-(2-cyanoethyl)]phosphoryl deoxythymidin-3'-yl-[3,4,5-tris(octadecyloxy)benzyl]succinate) as a white solid (209 mg, yield 88%).

Experimental Example 1: Study of Quencher (1) Preparation of Reaction Solution

Under an argon atmosphere, HO-dT-SUC-TOB (100 mg, 80.8 μmol) and MeOC(O)-TOB (100 mg, 106 μmol) were dissolved in dehydrated dichloromethane (4.0 mL). To this solution was added a mixture of dG-CE phosphoramidite (204 mg, 242 μmol) and 5-benzylthio-1H-tetrazole (46.5 mg, 242 μmol) prepared by dissolving in dehydrated acetonitrile (0.5 mL), and the mixture was stirred at room temperature for 30 min. Completion of the reaction was confirmed by thin layer chromatography (dichloromethane/methanol=10/1 (volume ratio)), a quencher in the kind and amount shown in Table 1 was added and the mixture was stirred at room temperature for 30 min. Then, an oxidant shown in Table 1 (254 μmol, 1.05 molar equivalents relative to phosphoramidite monomer) was added and the mixture was stirred at room temperature for 1 hr to prepare a reaction solution.

(2) Preparation of Test Solution (Pre-Treatment for Analysis)

The obtained reaction solution (50 μL) was dispensed to a 1.5 mL vial, diluted with tetrahydrofuran (450 μL), to which DBU (20 μL) was added and the mixture was stirred for 30 sec to prepare a test solution.

(3) Analysis

The obtained test solution was measured by mass spectrometry using LC-TOF MS (Agilent6230). The amount of the byproduct was calculated by the following formula based on the abundance of each compound observed (object compound and byproduct).

amount(%) of branch product=(abundance of branch product/abundance of object compound)×100 amount(%) of phosphoric acid triester cleavage product=(abundance of phosphoric acid triester cleavage product/abundance of object compound)×100

As used herein, the object compound refers to the object oligonucleotide contained in the reaction solution, the branch product refers to a byproduct produced by falling off of an amino-protecting group of nucleic acid base of the object compound and binding of the amino group and a monomer, and the phosphoric acid triester cleavage product refers to a byproduct produced by cleavage of phosphoric acid triester of the object compound. The results are shown in Table 1.

TABLE 1

| quencher | | | amount (%) | |
|---|---|---|---|---|
| kind | amount (molar equivalents) | oxidant | of branch product | amount (%) of phosphoric acid triester cleavage product |
| 2,2,2-trifluoroethanol | 5 | iodine/water/pyridine | 3.11 | 183 |
| 2,2,2-trifluoroethanol | 1 | iodine/water/pyridine | 0.69 | 0.16 |
| hexafluoroisopropanol | 5 | iodine/water/pyridine | 1.14 | 61.61 |
| water | 1 | iodine/water/pyridine | 5.08 | — |
| t-butanol | 5 | iodine/water/pyridine | 10.29 | — |
| morpholine | 5 | iodine/water/pyridine | — | 0.79 |
| morpholine | 5 | CSO | — | — |
| 5-hydroxy-indole | 5 | iodine/water/pyridine | 0.17 | — |
| 4-nitro-phenol | 5 | iodine/water/pyridine | 0.08 | 31.72 |
| ribose | 5 | iodine/water/pyridine | 4.90 | 0.09 |
| phloroglucinol | 5 | iodine/water/pyridine | 0.74 | 0.05 |
| tetrahydrofurfuryl alcohol | 5 | CSO | — | — |
| diethylene glycol | 5 | CSO | — | — |
| ethylene glycol | 5 | CSO | — | — |
| acetamide | 5 | CSO | 2.80 | — |

(note)
"amount of quencher" = "molar equivalents relative to phosphoramidite monomer"
"—" = "below detection limit"

As shown in Table 1, when CSO was used as an oxidant and morpholine, tetrahydrofurfuryl alcohol, diethylene glycol or ethylene glycol was used as a quencher, production of a branch product and a phosphoric acid triester cleavage product was confirmed to have been effectively suppressed.

Experimental Example 2: Study of Quencher (1) Preparation of Reaction Solution

Under an argon atmosphere, HO-dT-SUC-TOB (100 mg, 80.8 mol) was dissolved in dehydrated dichloromethane (4.0 mL), a mixed solution of rA$_{OMe}$(Bz)-CE phosphoramidite (215 mg, 242 mol) and 5-benzylthio-1H-tetrazole (46.5 mg, 242 μmol) in dehydrated acetonitrile (0.5 mL) was added, and the mixture was stirred at room temperature for 1 hr. Completion of the reaction was confirmed by thin layer chromatography (dichloromethane/methanol=10/1 (volume ratio)), a quencher in the kind and amount shown in Table 2 was added and the mixture was stirred at room temperature for 30 min. Then, CSO (58.2 mg, 254 μmol) was added and the mixture was stirred at room temperature for 1 hr. Furthermore, to the reaction solution were added 5-methoxyindole (238 mg, 1.62 mmol) and trifluoroacetic acid (92.5 mL, 1.21 mmol) and the mixture was stirred at room temperature for 18 hr to prepare a reaction solution.

(2) Preparation and Analysis of Test Solution

In the same manner as in Experimental Example 1, the prepared test solution was measured by mass spectrometry and the amount of the byproduct was calculated by the following formula based on the abundance of each compound observed (object compound and byproduct).

amount(%) of+1monomer product=(abundance of+1monomer product/abundance of object compound)×100 amount(%) of base-part deprotected product=(abundance of base-part deprotected product/abundance of object compound)×100

As used herein, the +1 monomer product refers to a byproduct produced by binding of one redundant monomer to the object compound, and the base-part deprotected product refers to a byproduct produced by falling off of an amino-protecting group of nucleic acid base of the object compound. The results are shown in Table 2.

TABLE 2

| quencher | | | |
|---|---|---|---|
| kind | amount (molar equivalents) | amount (%) of +1 monomer product | amount (%) of base-part deprotected product |
| morpholine | 5 | 0.73 | 0.61 |
| tetrahydrofurfuryl alcohol | 5 | 0.11 | — |
| tetrahydrofurfuryl alcohol | 1 | 0.09 | — |
| diethylene glycol | 5 | 0.15 | 0.06 |
| ethylene glycol | 5 | 0.09 | 0.08 |
| acetamide | 5 | 0.36 | — |
| 2-pyrrolidone | 5 | 0.79 | — |

(note)
"amount of quencher" = "molar equivalents relative to phosphoramidite monomer"
"—" = "below detection limit"

As shown in Table 2, when tetrahydrofurfuryl alcohol, diethylene glycol or ethylene glycol was used as a quencher, production of a +1 monomer product and a base-part deprotected product was confirmed to have been effectively suppressed.

Experimental Example 3: Study of Quencher (1) Preparation of Reaction Solution

As shown in the below-mentioned Reference Examples 1 to 11, the reaction solution was prepared.

(2) Preparation and Analysis of Test Solution

In the same manner as in Experimental Example 2, the prepared test solution was measured by mass spectrometry, and the amount of the +1 monomer product and the amount of the base-part deprotected product were calculated. The results are shown in Table 3.

TABLE 3

| reaction solution | quencher kind | amount (molar equivalents) | neutralized salt kind | amount (molar equivalents) | amount (%) of +1 monomer product | amount (%) of base-part deprotected product |
|---|---|---|---|---|---|---|
| Reference Example 1 | methanol | 10 | none | none | — | 0.54 |
| Reference Example 2 | methanol | 5 | acetic acid + 2,4,6-trimethylpyridine | 2 | 0.33 | 0.34 |
| Reference Example 3 | none | none | acetic acid + pyridine | 10 | 1.02 | — |
| Reference Example 4 | none | none | acetic acid + N-methylimidazole | 2 | 1.48 | 0.21 |
| Reference Example 5 | methanol | 10 | acetic acid + N-methylimidazole | 2 | 0.08 | 2.53 |
| Reference Example 6 | t-butanol | 10 | none | none | 0.15 | — |
| Reference Example 7 | t-butanol | 10 | acetic acid + 2,4,6-trimethylpyridine | 2 | 0.11 | — |
| Reference Example 8 | 2-propanol | 5 | acetic acid + 2,4,6-trimethylpyridine | 2 | — | 0.06 |
| Reference Example 9 | 2,2,2-trifluoroethanol | 10 | acetic acid + 2,4,6-trimethylpyridine | 2 | — | — |
| Reference Example 10 | 2,2,2-trifluoroethanol | 5 | none | none | — | — |
| Reference Example 11 | t-butanol | 5 | none | none | — | — |

(note)
"amount of quencher" = "molar equivalents relative to phosphoramidite monomer"
"amount of neutralized salt" = "molar equivalents relative to phosphoramidite monomer"
"—" = "below detection limit"

As shown in Table 3, when methanol, t-butanol, 2,2,2-trifluoroethanol or 2-propanol was used as a quencher, production of a +1 monomer product was confirmed to have been suppressed. Furthermore, when t-butanol, 2,2,2-trifluoroethanol or 2-propanol was used, production of a base-part deprotected product was also confirmed to have been suppressed. In addition, when a neutralized salt of acetic acid and 2,4,6-trimethylpyridine was copresent together with alcohol confirmed to have a production suppressive effect on a +1 monomer product and a base-part deprotected product, production of a byproduct was confirmed to have been suppressed.

Experimental Example 4: Study of Unreacted Material (1) Preparation of Reaction Solution As shown in the below-mentioned Reference Examples 12 to 15, a reaction solution was prepared.

(2) Preparation of Test Solution

To the reaction solutions obtained in Reference Examples 12 to 15 were added a quencher and a neutralized salt in the kind and amount shown in Table 4. The reaction solution (50 µL) was dispensed to a 1.5 mL vial, DDTT (2.5 mg, 12 µmol) was added and the mixture was shaken for 30 sec. The mixture was diluted with tetrahydrofuran (450 µL), DBU (20 µL) was added and the mixture was stirred for 30 sec to give a test solution.

(3) Analysis

The obtained test solution was measured by mass spectrometry using LC-TOF MS (Agilent6230). The amount of the unreacted material was calculated by the following formula based on the abundance (m/z=2) of each compound observed (object compound and unreacted material).

amount(%) of unreacted material=(abundance of unreacted material/abundance of object compound)×100

As used herein, the unreacted material refers to a phosphoramidite monomer used for preparing the reaction solution.

TABLE 4

| reaction solution | quencher kind | amount (molar equivalents) | neutralized salt kind | amount (molar equivalents) | amount (%) of unreacted material |
|---|---|---|---|---|---|
| Reference Example 13 | t-butanol | 10 | none | none | 8.35 |
| Reference Example 14 | t-butanol | 10 | acetic acid + 2,4,6-trimethylpyridine | 2 | — |
| Reference Example 12 | 2,2,2-trifluoroethanol | 5 | none | none | 7.76 |

TABLE 4-continued

| reaction solution | quencher | | neutralized salt | | amount (%) of unreacted material |
| --- | --- | --- | --- | --- | --- |
| | kind | amount (molar equivalents) | kind | amount (molar equivalents) | |
| Reference Example 15 | 2,2,2-trifluoroethanol | 10 | acetic acid + 2,4,6-trimethylpyridine | 2 | — |

(note)
"amount of quencher" = "molar equivalents relative to phosphoramidite monomer"
"amount of neutralized salt" = "molar equivalents relative to phosphoramidite monomer"
"—" = "below detection limit"

As shown in Table 4, when t-butanol or 2,2,2-trifluoroethanol and a neutralized salt of acetic acid and 2,4,6-trimethylpyridine were copresent, condensation reaction was confirmed to have proceeded effectively without leaving an unreacted material during condensation reaction.

Experimental Example 5: Study of Purity of Phosphorothioate 10-Mer

The phosphorothioate 10-mer obtained in the below-mentioned Reference Examples 16-20 were analyzed by HPLC and the purity of the obtained 10-mer (area %) was calculated. The results of the purity (area %) of quencher, neutralized salt and 10-mer used are shown in Table 5.

TABLE 5

| 10-mer | quencher | | neutralized salt | | purity (area %) of 10-mer |
| --- | --- | --- | --- | --- | --- |
| | kind | amount (molar equivalents) | kind | amount (molar equivalents) | |
| Reference Example 16 | methanol | 10 | none | none | 82.6 |
| Reference Example 17 | methanol | 10 | acetic acid + 2,4,6-trimethylpyridine | 2 | 83.4 |
| Reference Example 18 | none | none | acetic acid + pyridine | 10 | 80.0 |
| Reference Example 19 | 2,2,2-trifluoroethanol | 10 | acetic acid + 2,4,6-trimethylpyridine | 2 | 93.6 |
| Reference Example 20 | t-butanol | 10 | acetic acid + 2,4,6-trimethylpyridine | 2 | 87.0 |

(note)
"amount of quencher" = "molar equivalents relative to phosphoramidite monomer"
"amount of neutralized salt" = "molar equivalents relative to phosphoramidite monomer"

As shown in Table 5, when 2,2,2-trifluoroethanol or t-butanol, and a neutralized salt of acetic acid and 2,4,6-trimethylpyridine was used, the purity of 10-mer was confirmed to be high.

Reference Example 1 (Example 9): Preparation of Reaction Solution (1) Synthesis of Dimer Under an argon atmosphere, in a 300 mL four-necked flask were placed HO-dT-SUC-TOB (619 mg, 500 µmol) and Ac-TOB (619 mg, 648 µmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (3.0 mL), and the mixture was stirred at room temperature for 1.5 hr. To the reaction solution was added methanol (608 µL, 15.0 mmol), and the mixture was stirred at room temperature for 15 min. After stirring, DDTT (340 mg, 1.65 mmol) was added, and the mixture was stirred at room temperature for 1 hr. Thereafter, 5-methoxyindole (1.47 g, 10.0 mmol) and trifluoroacetic acid (345 µL, 4.50 mmol) were successively added, and the mixture was stirred at room temperature for 1.5 hr. Furthermore, 2,4,6-trimethylpyridine (654 µL, 4.95 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (762 mg, yield 95%).

(2) Synthesis of Trimer

Under an argon atmosphere, in a 300 mL four-necked flask was placed the dimer (762 mg, 473 µmol) obtained in the above-mentioned (1), and it was dissolved in dehydrated dichloromethane (25 mL). To the obtained solution was added a mixed solution of 5-benzylthio-1H-tetrazole (273 mg, 1.42 mmol) and dA-CE phosphoramidite (1.22 g, 1.42 mmol) prepared by dissolving in dehydrated acetonitrile (3.0 mL), and the mixture was stirred at room temperature for 1.5 hr. To the reaction solution was added methanol (575 µL, 14.2 mmol), and the mixture was stirred at room temperature for 15 min. After stirring, DDTT (321 mg, 1.56 mmol) was added, and the mixture was stirred at room temperature for 1 hr. Thereafter, 5-methoxyindole (1.39 g, 9.46 mmol) and trifluoroacetic acid (326 µL, 4.26 mmol) were successively added, and the mixture was stirred at room temperature for 1.5 hr to prepare a reaction solution.

Since Reference Example 1 includes steps (1), (3), (4) and (6) in the synthesis of the above-mentioned dimer, it is one embodiment of the present invention.

Reference Example 2 (Example 10): Preparation of Reaction Solution (1) Synthesis of Dimer Under an argon atmosphere, in a 10 mL Schlenk tube were placed HO-dT-SUC-TOB (80.4 mg, 64.9 mol) and Ac-TOB (99.6 mg, 104 μmol) and they were dissolved in dehydrated dichloromethane (3.0 mL). To the obtained solution was added a mixed solution of 5-benzylthio-1H-tetrazole (37.4 mg, 195 μmol) and dT-CE phosphoramidite (145 mg, 195 μmol) prepared by dissolving in dehydrated acetonitrile (0.5 mL), and the mixture was stirred at room temperature for 1.5 hr was stirred. To the reaction solution was added methanol (39.5 μL, 975 μmol), a mixture of acetic acid (22.3 μL, 390 μmol) was added, and 2,4,6-trimethylpyridine (77.0 μL, 585 μmol), and the mixture was stirred at room temperature for 15 min. After stirring, DDTT (44.0 mg, 215 μmol) was added, and the mixture was stirred at room temperature for 1 hr. Thereafter, 5-methoxyindole (1.47 g, 10.0 mmol) and trifluoroacetic acid (89.6 μL, 1.17 mmol) were successively added, and the mixture was stirred at room temperature for 1.5 hr. Furthermore, 2,4,6-trimethylpyridine (170 μL, 1.29 mmol) was added, acetonitrile (10 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (104 mg, yield 99%).

(2) Synthesis of Trimer

Under an argon atmosphere, in a 300 mL four-necked flask was placed the dimer (104 mg, 64.2 μmol) obtained in the above-mentioned (1) and it was dissolved in dehydrated dichloromethane (3.0 mL). To the obtained solution was added a mixed solution of 5-benzylthio-1H-tetrazole (37.5 mg, 195 μmol) and dA-CE phosphoramidite (165 mg, 195 μmol) prepared by dissolving in dehydrated acetonitrile (0.5 mL), and the mixture was stirred at room temperature for 1.5 hr. To the reaction solution was added methanol (39.5 μL, 975 μmol), a mixture of acetic acid (22.3 μL, 390 μmol) and 2,4,6-trimethylpyridine (77.0 μL, 585 μmol) was added, and the mixture was stirred at room temperature for 15 min. After stirring, DDTT (44.0 mg, 214 μmol) was added and the mixture was stirred at room temperature for 1 hr. Thereafter, 5-methoxyindole (158 mg, 1.07 mmol) and trifluoroacetic acid (74.7 μL, 975 μmol) were successively added, and the mixture was stirred at room temperature for 1.5 hr to prepare a reaction solution.

Since Reference Example 2 includes steps (1), (3), (4) and (6) in the synthesis of the above-mentioned dimer, it is one embodiment of the present invention.

Reference Example 3 (Example 11): Preparation of Reaction Solution (1) Synthesis of Dimer Under an argon atmosphere, in a 300 mL four-necked flask were placed HO-dT-SUC-TOB (618 mg, 499 μmol) and Ac-TOB (618 mg, 646 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.11 g, 1.50 mmol) prepared by dissolving in dehydrated acetonitrile (3.0 mL), and the mixture was stirred at room temperature for 1.5 hr. To the reaction solution was added a mixture of acetic acid (857 μL, 15.0 mmol) and pyridine (1.82 mL, 22.4 mmol), and the mixture was stirred at room temperature for 15 min. After stirring, DDTT (338 mg, 1.65 mmol) was added, and the mixture was stirred at room temperature for 1 hr. Thereafter, 5-methoxyindole (1.47 g, 10.0 mmol) and trifluoroacetic acid (344 μL, 4.49 mmol) were successively added, and the mixture was stirred at room temperature for 1.5 hr. Furthermore, 2,4,6-trimethylpyridine (653 μL, 4.94 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (753 mg, yield 94%).

(2) Synthesis of Trimer

Under an argon atmosphere, in a 300 mL four-necked flask was placed the dimer (753 mg, 468 μmol) obtained in the above-mentioned (1), and it was dissolved in dehydrated dichloromethane (25 mL). To the obtained solution was added a mixed solution of 5-benzylthio-1H-tetrazole (270 mg, 1.40 mmol) and dA-CE phosphoramidite (1.20 g, 1.40 mmol) prepared by dissolving in dehydrated acetonitrile (3.0 mL), and the mixture was stirred at room temperature for 1.5 hr. To the reaction solution was added a mixture of acetic acid (402 μL, 7.01 mmol) and pyridine (567 μL, 7.01 mmol), and the mixture was stirred at room temperature for 15 min. After stirring, DDTT (317 mg, 1.54 mmol) was added, and the mixture was stirred at room temperature for 1 hr. Thereafter, 5-methoxyindole (1.38 g, 9.35 mmol) and trifluoroacetic acid (322 μL, 4.21 mmol) were successively added, and the mixture was stirred at room temperature for 1.5 hr to prepare a reaction solution.

Since Reference Example 3 includes steps (1), (3), (4) and (6) in the synthesis of the above-mentioned dimer, it is one embodiment of the present invention.

Reference Example 4 (Example 12): Preparation of Reaction Solution (1) Synthesis of Dimer Under an argon atmosphere, in a 300 mL four-necked flask were placed HO-dT-SUC-TOB (619 mg, 500 μmol) and Ac-TOB (770 mg, 807 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (3.0 mL), and the mixture was stirred at room temperature for 1.5 hr. To the reaction solution was added a mixture of acetic acid (172 μL, 3.00 mmol) and N-methylimidazole (178 μL, 2.25 mmol), and the mixture was stirred at room temperature for 15 min. After stirring, DDTT (339 mg, 1.65 mmol) was added, and the mixture was stirred at room temperature for 1 hr. Thereafter, 5-methoxyindole (1.47 g, 10.0 mmol) and trifluoroacetic acid (574 μL, 7.50 mmol) were successively added, and the mixture was stirred at room temperature for 1.5 hr. Furthermore, N-methylimidazole (653 μL, 8.25 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (792 mg, 98%).

(2) Synthesis of Trimer

Under an argon atmosphere, in a 300 mL four-necked flask was placed the dimer (792 mg, 492 μmol) obtained in the above-mentioned (1), and it was dissolved in dehydrated dichloromethane (25 mL). To the obtained solution was added a mixed solution of 5-benzylthio-1H-tetrazole (284 mg, 1.48 mmol) and dA-CE phosphoramidite (1.27 g, 1.48 mmol) prepared by dissolving in dehydrated acetonitrile (3.0 mL), and the mixture was stirred at room temperature for 1.5 hr. To the reaction solution was added a mixture of acetic acid (169 μL, 2.95 mmol) and N-methylimidazole (175 μL, 2.21 mmol), and the mixture was stirred at room temperature for 15 min. After stirring, DDTT (333 mg, 1.62 mmol) was added, and the mixture was stirred at room temperature for 1 hr. Thereafter, 5-methoxyindole (1.45 g, 9.83 mmol) and trifluoroacetic acid (565 μL, 7.37 mmol) were successively added, and the mixture was stirred at room temperature for 1.5 hr to prepare a reaction solution.

Since Reference Example 4 includes steps (1), (3), (4) and (6) in the synthesis of the above-mentioned dimer, it is one embodiment of the present invention.

Reference Example 5 (Example 13): Preparation of Reaction Solution (1) Synthesis of Dimer Under an argon atmosphere, in a 300 mL four-necked flask were placed HO-dT-SUC-TOB (619 mg, 500 μmol) and Ac-TOB (770 mg, 807 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (3.0 mL), and the mixture was stirred at room temperature for 1.5 hr. To the reaction solution was added methanol (608 μL, 15.0 mmol), a mixture of acetic acid (172 μL, 3.00 mmol) and N-methylimidazole (356 μL, 4.50 mmol) was added, and the mixture was stirred at room temperature for 15 min. After stirring, DDTT (339 mg, 1.65 mmol) was added, and the mixture was stirred at room temperature for 1 hr. Thereafter, 5-methoxyindole (1.47 g, 10.0 mmol) and trifluoroacetic acid (689 μL, 9.00 mmol) were successively added, and the mixture was stirred at room temperature for 1.5 hr. Furthermore, N-methylimidazole (784 μL, 9.90 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (779 mg, yield 97%).

(2) Synthesis of Trimer

Under an argon atmosphere, in a 300 mL four-necked flask was placed the dimer (779 mg, 483 μmol) obtained in the above-mentioned (1), and it was dissolved in dehydrated dichloromethane (25 mL). To the obtained solution was added a mixed solution of 5-benzylthio-1H-tetrazole (279 mg, 1.45 mmol) and dA-CE phosphoramidite (1.24 g, 1.45 mmol) prepared by dissolving in dehydrated acetonitrile (3.0 mL), and the mixture was stirred at room temperature for 1.5 hr. To the reaction solution was added methanol (588 μL, 14.5 mmol), a mixture of acetic acid (166 μL, 2.90 mmol) and N-methylimidazole (344 μL, 4.35 mmol) was added, and the mixture was stirred at room temperature for 15 min. After stirring, DDTT (328 mg, 1.60 mmol) was added, and the mixture was stirred at room temperature for 1 hr. Thereafter, 5-methoxyindole (1.42 g, 9.67 mmol) and trifluoroacetic acid (666 μL, 8.70 mmol) were successively added, and the mixture was stirred at room temperature for 1.5 hr to prepare a reaction solution.

Since Reference Example 5 includes steps (1), (3), (4) and (6) in the synthesis of the above-mentioned dimer, it is one embodiment of the present invention.

Reference Example 6 (Example 14) and Reference Example 13 (Example 15): Preparation of Reaction Solution (1) Synthesis of Dimer Under an argon atmosphere, in a 10 mL Schlenk tube were placed HO-dT-SUC-TOB (80.3 mg, 65.0 μmol) and Ac-TOB (100 mg, 105 μmol) and they were dissolved in dehydrated dichloromethane (3.0 mL). To the obtained solution was added a mixed solution of 5-benzylthio-1H-tetrazole (37.4 mg, 195 μmol) and dT-CE phosphoramidite (145 mg, 195 μmol) prepared by dissolving in dehydrated acetonitrile (0.5 mL), and the mixture was stirred at room temperature for 1.5 hr. To the reaction solution was added t-butanol (186 μL, 1.95 mmol), and the mixture was stirred at room temperature for 15 min. After stirring, DDTT (44.0 mg, 214 μmol) was added, and the mixture was stirred at room temperature for 1 hr. Thereafter, 5-methoxyindole (94.6 mg, 642 μmol) and trifluoroacetic acid (44.7 μL, 584 μmol) were successively added, and the mixture was stirred at room temperature for 1.5 hr. Furthermore, 2,4,6-trimethylpyridine (84.6 μL, 642 μmol) was added, acetonitrile (10 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (104 mg, yield 100%).

(2) Synthesis of Trimer

Under an argon atmosphere, in a 300 mL four-necked flask was placed the dimer (104 mg, 65.0 μmol) obtained in the above-mentioned (1) and it was dissolved in dehydrated dichloromethane (3.0 mL). To the obtained solution was added a mixed solution of 5-benzylthio-1H-tetrazole (37.3 mg, 194 μmol) and dA-CE phosphoramidite (167 mg, 194 μmol) prepared by dissolving in dehydrated acetonitrile (0.5 mL), and the mixture was stirred at room temperature for 1.5 hr to prepare a reaction solution. The reaction solution obtained at this time point was used as the reaction solution of Reference Example 13 in the above-mentioned Experimental Example 4.

To the reaction solution obtained as mentioned above was added t-butanol (186 μL, 1.94 mmol), and the mixture was stirred at room temperature for 15 min. After stirring, DDTT (43.9 mg, 214 μmol) was added, and the mixture was stirred at room temperature for 1 hr. Thereafter, 5-methoxyindole (94.3 mg, 641 μmol) and trifluoroacetic acid (44.6 μL, 583 μmol) were successively added, and the mixture was stirred at room temperature for 1.5 hr to prepare a reaction solution. The reaction solution obtained at this time point was used as the reaction solution of Reference Example 6 in the above-mentioned Experimental Example 3.

Since Reference Example 6 and Reference Example 13 include steps (1), (3), (4) and (6) in the synthesis of the above-mentioned dimer, they are each one embodiment of the present invention.

Reference Example 7 (Example 16) and Reference Example 14 (Example 17): Preparation of Reaction Solution (1) Synthesis of Dimer Under an argon atmosphere, in a 300 mL four-necked flask were placed HO-dT-SUC-TOB (619 mg, 500 µmol) and Ac-TOB (772 mg, 808 mol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (3.0 mL), and the mixture was stirred at room temperature for 1.5 hr. To the reaction solution was added t-butanol (1.43 mL, 15.0 mmol), a mixture of acetic acid (173 µL, 3.00 mmol) and 2,4,6-trimethylpyridine (594 µL, 4.50 mmol) was added, and the mixture was stirred at room temperature for 15 min. After stirring, DDTT (339 mg, 1.65 mmol) was added, and the mixture was stirred at room temperature for 1 hr. Thereafter, 5-methoxyindole (1.47 g, 10.0 mmol) and trifluoroacetic acid (689 µL, 8.99 mmol) were successively added, and the mixture was stirred at room temperature for 1.5 hr. Furthermore, 2,4,6-trimethylpyridine (1.31 mL, 9.89 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (798 mg, yield 99%).

(2) Synthesis of Trimer

Under an argon atmosphere, in a 300 mL four-necked flask was placed the dimer (798 mg, 495 µmol) obtained in the above-mentioned (1), and it was dissolved in dehydrated dichloromethane (25 mL). To the obtained solution was added a mixed solution of 5-benzylthio-1H-tetrazole (286 mg, 1.49 mmol) and dA-CE phosphoramidite, (1.27 g, 1.49 mmol) prepared by dissolving in dehydrated acetonitrile (3.0 mL), and the mixture was stirred at room temperature for 1.5 hr to prepare a reaction solution. The reaction solution obtained at this time point was used as the reaction solution of Reference Example 14 in the above-mentioned Experimental Example 4.

To the reaction solution obtained as mentioned above was added t-butanol (1.42 mL, 14.8 mmol), a mixture of acetic acid (171 µL, 2.97 mmol) and 2,4,6-trimethylpyridine (589 µL, 4.46 mmol) was added, and the mixture was stirred at room temperature for 15 min. After stirring, DDTT (335 mg, 1.63 mmol) was added, and the mixture was stirred at room temperature for 1 hr. Thereafter, 5-methoxyindole (1.46 g, 9.90 mmol) and trifluoroacetic acid (569 µL, 7.43 mmol) were successively added, and the mixture was stirred at room temperature for 1.5 hr to prepare a reaction solution. The reaction solution obtained at this time point was used as the reaction solution of Reference Example 7 in the above-mentioned Experimental Example 3.

Since Reference Example 7 and Reference Example 14 include steps (1), (3), (4) and (6) in the synthesis of the above-mentioned dimer, they are each one embodiment of the present invention.

Reference Example 8 (Example 18): Preparation of Reaction Solution (1) Synthesis of Dimer Under an argon atmosphere, in a 10 mL Schlenk tube was placed HO-dT-SUC-TOB (80.3 g, 65.0 µmol) and it was dissolved in dehydrated dichloromethane (3.0 mL). To the obtained solution was added a mixed solution of 5-benzylthio-1H-tetrazole (37.4 mg, 195 µmol) and dT-CE phosphoramidite (145 mg, 195 µmol) prepared by dissolving in dehydrated acetonitrile (0.5 mL), and the mixture was stirred at room temperature for 1.5 hr. To the reaction solution was added 2-propanol (74.8 µL, 974 µmol), a mixture of acetic acid (22.2 µL, 390 µmol) and 2,4,6-trimethylpyridine (77.1 µL, 585 µmol) was added, and the mixture was stirred at room temperature for 15 min. After stirring, DDTT (44.0 mg, 214 µmol) was added, and the mixture was stirred at room temperature for 1 hr. Thereafter, 5-methoxyindole (94.6 mg, 643 µmol) and trifluoroacetic acid (44.7 µL, 584 µmol) were successively added, and the mixture was stirred at room temperature for 1.5 hr. Furthermore, 2,4,6-trimethylpyridine (84.6 µL, 643 µmol) was added, acetonitrile (10 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (101 mg, yield 98%).

(2) Synthesis of Trimer

Under an argon atmosphere, in a 300 mL four-necked flask was placed the dimer (101 mg, 63.0 µmol) obtained in the above-mentioned (1) and it was dissolved in dehydrated dichloromethane (3.0 mL). To the obtained solution was added a mixed solution of 5-benzylthio-1H-tetrazole (36.3 mg, 189 µmol) and dA-CE phosphoramidite (162 mg, 189 µmol) prepared by dissolving in dehydrated acetonitrile (0.5 mL), and the mixture was stirred at room temperature for 1.5 hr. To the reaction solution was added 2-propanol (72.5 µL, 944 µmol), a mixture of acetic acid (10.8 µL, 189 µmol) and 2,4,6-trimethylpyridine (37.3 µL, 283 µmol) was added, and the mixture was stirred at room temperature for 15 min. After stirring, DDTT (42.6 mg, 208 µmol) was added, and the mixture was stirred at room temperature for 1 hr. Thereafter, 5-methoxyindole (91.7 mg, 623 µmol) and trifluoroacetic acid (43.4 µL, 566 µmol) were successively added, and the mixture was stirred at room temperature for 1.5 hr to prepare a reaction solution.

Since Reference Example 8 includes steps (1), (3), (4) and (6) in the synthesis of the above-mentioned dimer, it is one embodiment of the present invention.

Reference Example 9 (Example 19) and Reference Example 15 (Example 20): Preparation of Reaction Solution (1) Synthesis of Dimer Under an argon atmosphere, in a 300 mL four-necked flask was placed HO-dT-SUC-TOB (180 mg, 64.9 µmol) and it was dissolved in dehydrated dichloromethane (3.0 mL). To the obtained solution was added a mixed solution of 5-benzylthio-1H-tetrazole (37.4 mg, 195 µmol) and dT-CE phosphoramidite (145 mg, 195 µmol) prepared by dissolving in dehydrated acetonitrile (0.5 mL), and the mixture was stirred at room temperature for 1.5 hr. To the reaction solution was added 2,2,2-trifluoroethanol (140 µL, 1.95 mmol), a mixture of acetic acid (22.3 µL, 390 µmol) and 2,4,6-trimethylpyridine (77.0 µL, 585 µmol) was added, and the mixture was stirred at room temperature for 15 min. After stirring, DDTT (44.0 mg, 215 µmol) was added, and the mixture was stirred at room temperature for 1 hr. Thereafter, 5-methoxyindole (189 mg, 1.17 mmol) and trifluoroacetic acid (89.6 µL, 1.17 mmol) were successively added, and the mixture was stirred at room temperature for 1.5 hr. Furthermore, 2,4,6-trimethylpyridine (170 µL, 1.29 mmol) was added, acetonitrile (10 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (104 mg, yield 99%).

(2) Synthesis of Trimer

Under an argon atmosphere, in a 300 mL four-necked flask was placed the dimer (101 mg, 62.5 µmol) obtained in the above-mentioned (1) and it was dissolved in dehydrated dichloromethane (3.0 mL). To the obtained solution was added a mixed solution of 5-benzylthio-1H-tetrazole (36.1 mg, 188 µmol) and dA-CE phosphoramidite (161 mg, 188 µmol) prepared by dissolving in dehydrated acetonitrile (0.5 mL), and the mixture was stirred at room temperature for 1.5 hr to prepare a reaction solution. The reaction solution obtained at this time point was used as the reaction solution of Reference Example 15 in the above-mentioned Experimental Example 4.

To the reaction solution obtained as mentioned above was added 2,2,2-trifluoroethanol (134 µL, 1.88 mmol), a mixture of acetic acid (21.5 µL, 376 µmol) and 2,4,6-trimethylpyridine (74.3 µL, 564 µmol) was added, and the mixture was stirred at room temperature for 15 min. After stirring, DDTT (42.5 mg, 207 µmol) was added, and the mixture was stirred at room temperature for 1 hr. Thereafter, 5-methoxyindole (147 mg, 1.00 mmol) and trifluoroacetic acid (72.0 µL, 910 µmol) were successively added, and the mixture was stirred at room temperature for 1.5 hr to prepare a reaction solution. The reaction solution obtained at this time point was used as the reaction solution of Reference Example 9 in the above-mentioned Experimental Example 3.

Since Reference Example 9 and Reference Example 15 include steps (1), (3), (4) and (6) in the synthesis of the above-mentioned dimer, they are each one embodiment of the present invention.

Reference Example 10: Preparation of Reaction Solution

Under an argon atmosphere, in a 10 mL Schlenk tube was placed HO-dA-SUC-TOB (182 mg, 60.5 µmol) and it was dissolved in dehydrated dichloromethane (3.0 mL). To the obtained solution was added a mixed solution of 5-benzylthio-1H-tetrazole (35.0 mg, 182 µmol) and dT-CE phosphoramidite (135 mg, 182 µmol) prepared by dissolving in dehydrated acetonitrile (0.5 mL), and the mixture was stirred at room temperature for 1.5 hr. To the reaction solution was added 2,2,2-trifluoroethanol (65.3 µL, 910 µmol), and the mixture was stirred at room temperature for 15 min. After stirring, DDTT (41.1 mg, 200 µmol) was added, and the mixture was stirred at room temperature for 1 hr. Thereafter, 5-methoxyindole (88.4 mg, 600 µmol) and trifluoroacetic acid (41.8 µL, 546 µmol) were successively added, and the mixture was stirred at room temperature for 1.5 hr to prepare a reaction solution.

Reference Example 11: Preparation of Reaction Solution

Under an argon atmosphere, in a 10 mL Schlenk tube was placed HO-dA-SUC-TOB (182 mg, 60.5 µmol) and it was dissolved in dehydrated dichloromethane (3.0 mL). To the obtained solution was added a mixed solution of 5-benzylthio-1H-tetrazole (35.0 mg, 182 µmol) and dT-CE phosphoramidite (135 mg, 182 µmol) prepared by dissolving in dehydrated acetonitrile (0.5 mL), and the mixture was stirred at room temperature for 1.5 hr. To the reaction solution was added t-butanol (87.0 µL, 910 µmol), and the mixture was stirred at room temperature for min. After stirring, DDTT (41.1 mg, 200 µmol) was added, and the mixture was stirred at room temperature for 1 hr. Thereafter, 5-methoxyindole (88.4 mg, 600 µmol) and trifluoroacetic acid (41.8 µL, 546 µmol) were successively added, and the mixture was stirred at room temperature for 1.5 hr to prepare a reaction solution.

Reference Example 12 (Example 21): Preparation of Reaction Solution (1) Synthesis of Dimer Under an argon atmosphere, in a 10 mL Schlenk tube were placed HO-dT-SUC-TOB (80.3 mg, 65.0 µmol) and Ac-TOB (100 mg, 105 µmol) and they were dissolved in dehydrated dichloromethane (3.0 mL). To the obtained solution was added a mixed solution of 5-benzylthio-1H-tetrazole (37.4 mg, 195 µmol) and dT-CE phosphoramidite (145 mg, 195 µmol) prepared by dissolving in dehydrated acetonitrile (0.5 mL), and the mixture was stirred at room temperature for 1.5 hr. To the reaction solution was added 2,2,2-trifluoroethanol (69.6 µL, 973 µmol), DDTT (44.0 mg, 214 µmol) was added, and the mixture was stirred at room temperature for 1 hr. Thereafter, 5-methoxyindole (94.6 mg, 642 µmol) and trifluoroacetic acid (44.7 µL, 584 µmol) were successively added, and the mixture was stirred at room temperature for 1.5 hr. Furthermore, 2,4,6-trimethylpyridine (84.6 µL, 642 µmol) was added, acetonitrile (10 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (98.3 mg, yield 94%).

(2) Synthesis of Trimer

Under an argon atmosphere, in a 300 mL four-necked flask was placed the dimer (98.3 mg, 61.0 µmol) obtained in the above-mentioned (1) and it was dissolved in dehydrated dichloromethane (3.0 mL). To the obtained solution was added a mixed solution of 5-benzylthio-1H-tetrazole (35.2 mg, 183 µmol) and dA-CE phosphoramidite (157 mg, 183 µmol) prepared by dissolving in dehydrated acetonitrile (0.5 mL), and the mixture was stirred at room temperature for 1.5 hr to prepare a reaction solution.

Since Reference Example 12 includes steps (1), (3), (4) and (6) in the synthesis of the above-mentioned dimer, it is one embodiment of the present invention.

Reference Example 16 (Example 22): Continuous Synthesis of Phosphorothioate 10-Mer (SEQ ID NO: 2:5'-GACATGCATT-3') in Liquid (1) Synthesis of Phosphorothioate Dimer Wherein 3'-Hydroxy Group is Protected by Anchor Under an argon atmosphere, in a 300 mL four-necked flask were placed HO-dT-SUC-TOB (619 mg, 500 mol) and Ac-TOB (619 mg, 648 µmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (3.0 mL), and the mixture was stirred at room temperature for 1.5 hr. To the reaction solution was added methanol (608 µL, 15.0 mmol), and the mixture was stirred at room temperature for 15 min. After stirring, DDTT (340 mg, 1.65 mmol) was added, and the mixture was stirred at room temperature for 1 hr. Thereafter, 5-methoxyindole (1.47 g, 10.0 mmol) and trifluoroacetic acid (345 μL, 4.50 mmol) were successively added, and the mixture was stirred at room temperature for 1.5 hr. Furthermore, 2,4,6-trimethylpyridine (654 μL, 4.95 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (762 mg, yield 95%).

(2) Synthesis of Phosphorothioate 9-Mer Wherein 3'-Hydroxy Group is Protected by Anchor An operation similar to that in the above-mentioned (1) was further repeated 7 times to give a 9-mer (N$^6$-benzoyl-deoxyadenosine 3'-[O-(2-cyanoethyl)]phosphorothionyl-N$^4$-(2-hexyl)decanoyl-deoxycytidine 3'-(2-cyanoethyl)]phosphorothionyl-N$^6$-benzoyl-deoxyadenosine 3'-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl]phosphorothionyl-N$^4$-(2-hexyl)decanoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy) benzyl succinate) (2.03 g).

(3) Synthesis of Phosphorothioate 10-Mer Wherein 3'-Hydroxy Group is Protected by Anchor and 5'-Hydroxy Group is Protected by DMTr Group Under an argon atmosphere, in a 300 mL four-necked flask was placed the 9-mer (2.03 g) of the above-mentioned (2), and it was dissolved in dehydrated dichloromethane (25 mL). To the obtained solution was added a mixed solution of 5-benzylthio-1H-tetrazole (228 mg, 1.19 mmol) and dG-CE phosphoramidite (1.00 g, 1.19 mmol) prepared by dissolving in dehydrated acetonitrile (2.0 mL), and the mixture was stirred at room temperature for 1.5 hr. DDTT (338 mg, 1.64 mmol) was added, and the mixture was stirred at room temperature for 30 min. After stirring, acetonitrile (150 mL) was added to the reaction solution and the precipitated solid was collected by suction filtration using a KIRIYAMA ROHTO and dried to give a 10-mer (5'-O-(4,4'-dimethoxytrityl)-N$^2$-isobutyryl-deoxyguanosine 3'-[O-(2-cyanoethyl)]phosphorothionyl-N$^6$-benzoyl-deoxyadenosine 3'-[O-(2-cyanoethyl)]phosphorothionyl-N$^4$-(2-hexyl)decanoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl)]phosphorothionyl-N$^4$-(2-hexyl)decanoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) as a white solid (2.28 g).

(4) Deprotection

A mixture of the 10-mer (20 mg) obtained in the above-mentioned (3) and 30 wt % aqueous ammonia (5.00 mL) was placed in an autoclave, heated at 55° C. for 16 hr and cooled to room temperature. Insoluble material in the reaction solution was removed by a syringe filter (Whatman 25 mm GD/X PVDF 0.45 μm), and the filtrate was freeze-dried to give the object deoxyguanidyl-[3'→5']-deoxyadenylyl-[3'→5']-deoxycytidinyl-[3'→5']-deoxyadenylyl-[3'→5']-deoxythymidinyl-[3'→5']-deoxyguanidyl-[3'→5' ]-deoxycytidinyl-[3'→5' ]-deoxyadenylyl-[3'→5']-deoxythymidinyl-[3'→5' ]-deoxythymidine.

HPLC (WATERS XBridge™ C18 2.5 μm 4.6×75 mm column, flow rate 1.0 mL/min, 8 mM TEA+100 mM HFIP, MeOH, gradient: 0-10 min; 5 to 60%, λ=260 nm):Rt=6.61, 6.75 min (41.3+41.3%);

TOF/MS: 3471.489

Since Reference Example 16 includes steps (1), (3), (4) and (6) in the synthesis of the above-mentioned dimer, it is one embodiment of the present invention.

Reference Example 17 (Example 23): Continuous Synthesis of Phosphorothioate 10-Mer (SEQ ID NO: 2:5'-GACATGCATT-3') in Liquid (1) Synthesis of Phosphorothioate Dimer Wherein 3'-Hydroxy Group is Protected by Anchor Under an argon atmosphere, in a 300 mL four-necked flask were placed HO-dT-SUC-TOB (619 mg, 500 μmol) and Ac-TOB (619 mg, 648 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (2.0 mL), and the mixture was stirred at room temperature for 1.5 hr. To the reaction solution was added methanol (608 μL, 15.0 mmol), and the mixture was stirred at room temperature for 15 min. Thereafter, a separately prepared mixture of acetic acid (172 μL, 3.00 mmol) and 2,4,6-trimethylpyridine (595 μL, 4.50 mmol) was added, DDTT (339 mg, 1.65 mmol) was further added and the mixture was stirred at room temperature for 1 hr. Thereafter, 5-methoxyindole (1.47 g, 10.0 mmol) and trifluoroacetic acid (689 μL, 9.00 mmol) were successively added, and the mixture was stirred at room temperature for 1.5 hr. The mixture was neutralized with 2,4,6-trimethylpyridine (654 μL, 4.95 mmol), acetonitrile (150 mL) was added, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (765 mg, yield 95%).

(2) Synthesis of Phosphorothioate 9-Mer Wherein 3'-Hydroxy Group is Protected by Anchor An operation similar to that in the above-mentioned (1) was further repeated 7 times to give a 9-mer (N$^6$-benzoyl-deoxyadenosine 3'-[O-(2-cyanoethyl)]phosphorothionyl-N$^4$-(2-hexyl)decanoyl-deoxycytidine 3'-[O-(2-cyanoethyl)]phosphorothionyl-N$^6$-benzoyl-deoxyadenosine 3'-[0-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl)]phosphorothionyl-N$^4$-(2-hexyl)decanoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) (2.18 g).

(3) Synthesis of Phosphorothioate 10-Mer Wherein 3'-Hydroxy Group is Protected by Anchor and 5'-Hydroxy Group is Protected by DMTr Group Under an argon atmosphere, in a 300 mL four-necked flask was placed the 9-mer (2.18 g) obtained in the above-mentioned (2), and it was dissolved in dehydrated dichloromethane (25 mL). To the obtained solution was added a mixed solution of 5-benzylthio-1H-tetrazole (272 mg, 1.42 mmol) and dG-CE phosphoramidite (1.19 g, 1.42 mmol) prepared by dissolving in dehydrated acetonitrile (2.0 mL), and the mixture was stirred at room temperature for 1.5 hr. DDTT (320 mg, 1.56 mmol) was added, and the mixture was stirred at room temperature for 30 min. After stirring, acetonitrile (150 mL) was added to the reaction solution and the precipitated solid was collected by suction filtration using a KIRIYAMA ROHTO and dried to give a 10-mer (5'-O-(4,4'-dimethoxytrityl)-$N^2$-isobutyryl-deoxyguanosine 3'-[O-(2-cyanoethyl)]phosphorothionyl-$N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl3,4,5-tris(octadecyloxy)benzyl succinate) as a white solid (2.39 g).

(4) Deprotection

A mixture of 10-mer (20 mg) obtained in the above-mentioned (3) and 30 wt % aqueous ammonia (5.00 mL) was placed in an autoclave, heated at 55° C. for 16 hr and cooled to room temperature. Insoluble material in the reaction solution was removed by a syringe filter (Whatman 25 mm GD/X PVDF 0.45 μm), and the filtrate was freeze-dried to give the object deoxyguanidyl-[3'→5']-deoxyadenylyl-[3'→5']-deoxycytidinyl-[3'→5' ]-deoxyadenylyl-[3'→5' ]-deoxythymidinyl-[3'→5' ]-deoxyguanidyl-[3'→5']-deoxycytidinyl-[3'→5']-deoxyadenylyl-[3'→5']-deoxythymidinyl-[3'→5' ]-deoxythymidine.

HPLC (WATERS XBridge™ C18 2.5 μm 4.6×75 mm column, flow rate 1.0 mL/min, 8 mM TEA+100 mM HFIP, MeOH, gradient: 0-10 min; 5 to 60%, λ=260 nm):Rt=7.06, 7.19 min (41.1+42.3%);

TOF/MS: 3471.49

Since Reference Example 17 includes steps (1), (3), (4) and (6) in the synthesis of the above-mentioned dimer, it is one embodiment of the present invention.

Reference Example 18 (Example 24): Continuous Synthesis of Phosphorothioate 10-Mer (SEQ ID NO: 2: 5'-GACATGCATT-3') in Liquid (1) Synthesis of Phosphorothioate Dimer Wherein 3'-Hydroxy Group is Protected by Anchor Under an argon atmosphere, in a 300 mL four-necked flask were placed HO-dT-SUC-TOB (617.5 mg, 499 μmol) and Ac-TOB (619 mg, 648 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (3.0 mL), and the mixture was stirred at room temperature for 1.5 hr. To the reaction solution was added a separately prepared mixture of acetic acid (857 μL, 15.0 mmol) and dehydrated pyridine (1.82 mL, 22.5 mmol), and the mixture was stirred at room temperature for 15 min. After stirring, DDTT (338 mg, 1.65 mmol) was added, and the mixture was stirred at room temperature for 1 hr. Thereafter, 5-methoxyindole (1.47 g, 10.0 mmol) and trifluoroacetic acid (345 μL, 4.50 mmol) were successively added, and the mixture was stirred at room temperature for 1.5 hr. Furthermore, 2,4,6-trimethylpyridine (653 μL, 4.94 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (753 mg, yield 94%).

(2) Synthesis of Phosphorothioate 9-Mer Wherein 3'-Hydroxy Group is Protected by Anchor An operation similar to that in the above-mentioned (1) was further repeated 7 times to give a 9-mer ($N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[0-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxythymidine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) (1.41 g).

(3) Synthesis of Phosphorothioate 10-Mer Wherein 3'-Hydroxy Group is Protected by Anchor and 5'-Hydroxy Group is Protected by DMTr Group Under an argon atmosphere, in a 300 mL four-necked flask was placed the 9-mer (1.41 g) obtained in the above-mentioned (2), and it was dissolved in dehydrated dichloromethane (25 mL). To the obtained solution was added a mixed solution of 5-benzylthio-1H-tetrazole (159 mg, 829 μmol) and dG-CE phosphoramidite (696 mg, 829 μmol) prepared by dissolving in dehydrated acetonitrile (2.0 mL), and the mixture was stirred at room temperature for 1.5 hr. DDTT (187 mg, 912 μmol) was added, and the mixture was stirred at room temperature for 30 min. After stirring, acetonitrile (150 mL) was added to the reaction solution and the precipitated solid was collected by suction filtration using a KIRIYAMA ROHTO and dried to give a 10-mer (5'-O-(4,4'-dimethoxytrityl)-$N^2$-isobutyryl-deoxyguanosine 3'-[O-(2-cyanoethyl)]phosphorothionyl-$N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[0-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) as a white solid (1.51 g).

(4) Deprotection

A mixture of the 10-mer (20 mg) obtained in the above-mentioned (3) and 30 wt % aqueous ammonia (5.00 mL) was placed in an autoclave, heated at 55° C. for 16 hr and cooled to room temperature. Insoluble material in the reaction solution was removed by a syringe filter (Whatman 25 mm GD/X PVDF 0.45 μm), and the filtrate was freeze-dried to give the object deoxyguanidyl-[3'→5']-deoxyadenylyl-[3'→5']-deoxycytidinyl-[3'→5']-deoxyadenylyl-[3'→5']-deoxythymidinyl-[3'→5']-deoxyguanidyl-[3'→5']-deoxycytidinyl-[3'→5']-deoxyadenylyl-[3'→5' ]-deoxythymidinyl-[3'→5' ]-deoxythymidine.

HPLC (WATERS XBridge™ C18 2.5 μm 4.6×75 mm column, flow rate 1.0 mL/min, 8 mM TEA+100 mM HFIP, MeOH, gradient: 0-10 min; 5 to 60%, λ=260 nm):Rt=7.32, 7.47 min (40.3 area %+39.7 area %); TOF/MS: 3471.493

Since Reference Example 18 includes steps (1), (3), (4) and (6) in the synthesis of the above-mentioned dimer, it is one embodiment of the present invention.

Reference Example 19 (Example 25): Continuous Synthesis of Phosphorothioate 10-Mer (SEQ ID NO: 2: 5'-GACATGCATT-3') in Liquid (1) Synthesis of Phosphorothioate Dimer Wherein 3'-Hydroxy Group is Protected by Anchor Under an argon atmosphere, in a 300 mL four-necked flask were placed HO-dT-SUC-TOB (619 mg, 500 μmol) and Ac-TOB (619 mg, 648 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (2.0 mL), and the mixture was stirred at room temperature for 1.5 hr. To the reaction solution was added a mixture of 2,2,2-trifluoroethanol (1.09 mL, 15.0 mmol), and the mixture was stirred at room temperature for 15 min. Thereafter, a separately prepared mixture of acetic acid (172 μL, 3.00 mmol) and 2,4,6-trimethylpyridine (595 μL, 4.50 mmol) was added, DDTT (339 mg, 1.65 mmol) was further added, and the mixture was stirred at room temperature for 1 hr. Thereafter, 5-methoxyindole (1.47 g, 10.0 mmol) and trifluoroacetic acid (345 μL, 4.50 mmol) were successively added, and the mixture was stirred at room temperature for 1.5 hr. Furthermore, 2,4,6-trimethylpyridine (653 μL, 4.94 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl]succinate) as a white solid (788 mg, yield 98%).

(2) Synthesis of Phosphorothioate 9-Mer Wherein 3'-Hydroxy Group is Protected by Anchor An operation similar to that in the above-mentioned (1) was further repeated 7 times to give a 9-mer ($N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)] phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) (1.97 g).

(3) Synthesis of Phosphorothioate 10-Mer Wherein 3'-Hydroxy Group is Protected by Anchor and 5'-Hydroxy Group is Protected by DMTr Group Under an argon atmosphere, in a 300 mL four-necked flask was placed the compound (1.97 g) of the above-mentioned (2), and it was dissolved in dehydrated dichloromethane (25 mL). To the obtained solution was added a mixed solution of 5-benzylthio-1H-tetrazole (222 mg, 1.16 mmol) and dG-CE phosphoramidite (972 mg, 1.16 mmol) prepared by dissolving in dehydrated acetonitrile (2.0 mL), and the mixture was stirred at room temperature for 1.5 hr. DDTT (261 mg, 1.27 mmol) was added, and the mixture was stirred at room temperature for 30 min. After stirring, acetonitrile (150 mL) was added to the reaction solution and the precipitated solid was collected by suction filtration using a KIRIYAMA ROHTO and dried to give a 10-mer (5'-O-(4,4'-dimethoxytrityl)-$N^2$-isobutyryl-deoxyguanosine 3'-[O-(2-cyanoethyl)]phosphorothionyl-$N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-(2-hexyl)decanoyl-deoxycytidine 3'-[O-(2-cyanoethyl)]phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl 3,4,5-tris(octadecyloxy)benzyl succinate) as a white solid (2.21 g).

(4) Deprotection

A mixture of the 10-mer (20 mg) obtained in the above-mentioned (3) and 30 wt % aqueous ammonia (5.00 mL) was placed in an autoclave, heated at 55° C. for 16 hr and cooled to room temperature. Insoluble material in the reaction solution was removed by a syringe filter (Whatman 25 mm GD/X PVDF 0.45 μm), and the filtrate was freeze-dried to give the object deoxyguanidyl-[3'→5']-deoxyadenylyl-[3'→5']-deoxycytidinyl-[3'→5' ]-deoxyadenylyl-[3'→5']-deoxythymidinyl-[3'→5' ]-deoxyguanidyl-[3'→5' ]-deoxycytidinyl-[3'→5' ]-deoxyadenylyl-[3'→5' ]-deoxythymidinyl-[3'→5']-deoxythymidine.

HPLC (WATERS XBridge™ C18 2.5 μm 4.6×75 mm column, flow rate 1.0 mL/min, 8 mM TEA+100 mM HFIP, MeOH, gradient: 0-10 min; 5 to 60%, λ=260 nm):Rt=7.36, 7.48 min (48.8 area %+44.8 area %); TOF/MS: 3471.495

Since Reference Example 19 includes steps (1), (3), (4) and (6) in the synthesis of the above-mentioned dimer, it is one embodiment of the present invention.

Reference Example 20 (Example 26): Continuous Synthesis of Phosphorothioate 10-Mer (SEQ ID NO: 2: 5'-GACATGCATT-3') in Liquid (1) Synthesis of Phosphorothioate Dimer Wherein 3'-Hydroxy Group is Protected by Anchor Under an argon atmosphere, in a 300 mL four-necked flask were placed HO-dT-SUC-TOB (619 mg, 500 μmol) and Ac-TOB (619 mg, 648 μmol), and they were dissolved in dehydrated dichloromethane (25 mL). To the obtained solution was added a mixed solution of 5-benzylthio-1H-tetrazole (288 mg, 1.50 mmol) and dT-CE phosphoramidite (1.12 g, 1.50 mmol) prepared by dissolving in dehydrated acetonitrile (2.0 mL), and the mixture was stirred at room temperature for 1.5 hr. To the reaction solution was added t-butanol (1.43 mL, 15.0 mmol), and the mixture was stirred at room temperature for 15 min. Thereafter, a separately prepared mixture of acetic acid (173 μL, 3.00 mmol) and 2,4,6-trimethylpyridine (594 μL, 4.50 mmol) was added, DDTT (339 mg, 1.65 mmol) was further added, and the mixture was stirred at room temperature for 1 hr. Thereafter, 5-methoxyindole (1.47 g, 10.0 mmol) and trifluoroacetic acid (689 L, 8.99 mmol) were successively added, and the mixture was stirred at room temperature for 1.5 hr. Furthermore, 2,4,6-trimethylpyridine (1.31 mL, 9.89 mmol) was added, acetonitrile (150 mL) was added to the reaction solution, and the precipitated solid was collected by suction filtration using a KIRIYAMA ROHTO and dried to give a dimer (deoxythymidine-3'-[O-(2-cyanoethyl)]phosphorothionyl deoxythymidin-3'-yl-[3,4,5-tris(octadecyloxy)benzyl] succinate) as a white solid (798 mg, yield 99%).

(2) Synthesis of Phosphorothioate 9-Mer Wherein 3'-Hydroxy Group is Protected by Anchor An operation similar to that in the above-mentioned (1) was further repeated 7 times to give a 9-mer ($N^6$-benzoyl-deoxyadenosine 3'-[O-(2-cyanoethyl)]phosphorothionyl-$N^4$-(2-hexyl)decanoyl-deoxycytidine 3'-[O-(2-cyanoethyl)] phosphorothionyl-$N^6$-benzoyl-deoxyadenosine 3'-[O-(2-cyanoethyl)]phosphorothionyl-deoxythymidine 3'-[O-(2-cyanoethyl)]phosphorothionyl-$N^2$-isobutyryl-deoxyguanosine 3'-[O-(2-cyanoethyl)]phosphorothionyl-$N^4$-(2-hexyl) decanoyl-deoxycytidine 3'-[O-(2-cyanoethyl)]phosphorothionyl-$N^6$-benzoyl-deoxyadenosine 3'-[O-(2-cyanoethyl)] phosphorothionyl-deoxythymidine 3'-[O-(2-cyanoethyl)] phosphorothionyl-deoxythymidin-3'-yl 3,4,5-tris(octadecyloxy)benzyl succinate) (1.93 g).

(3) Synthesis of Phosphorothioate 10-Mer Wherein 3'-Hydroxy Group is Protected by Anchor and 5'-Hydroxy Group is Protected by DMTr Group Under an argon atmosphere, in a 300 mL four-necked flask was placed the 9-mer (1.93 g) obtained in the above-mentioned (2), and it was dissolved in dehydrated dichloromethane (25 mL). To the obtained solution was added a mixed solution of 5-benzylthio-1H-tetrazole (218 mg, 1.13 mmol) and dG-CE phosphoramidite (950 mg, 1.13 mmol) prepared by dissolving in dehydrated acetonitrile (2.0 mL), and the mixture was stirred at room temperature for 1.5 hr. DDTT (256 mg, 1.23 mmol) was added, and the mixture was stirred at room temperature for 30 min. After stirring, acetonitrile (150 mL) was added to the reaction solution and the precipitated solid was collected by suction filtration using a KIRIYAMA ROHTO and dried to give 10-mer (5'-O-(4,4'-dimethoxytrityl)-N$^2$-isobutyryl-deoxyguanosine 3'-[O-(2-cyanoethyl)]phosphorothionyl-N$^6$-benzoyl-deoxyadenosine 3'-(2-cyanoethyl)]phosphorothionyl-N$^4$-(2-hexyl)decanoyl-deoxycytidine 3'-[O-(2-cyanoethyl)]phosphorothionyl-N$^6$-benzoyl-deoxyadenosine 3'[O-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl)]phosphorothionyl-N$^4$-(2-hexyl)decanoyl-deoxycytidine 3-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidin-3'-yl3,4,5-tris(octadecyloxy)benzyl succinate) as a white solid (2.14 g).

(4) Deprotection

A mixture of the 10-mer (20 mg) obtained in the above-mentioned (3) and 30 wt % aqueous ammonia (5.00 mL) was placed in an autoclave, heated at 55° C. for 16 hr and cooled to room temperature. Insoluble material in the reaction solution was removed by a syringe filter (Whatman 25 mm GD/X PVDF 0.45 µm), and the filtrate was freeze-dried to give the object deoxyguanidyl-[3'→5']-deoxyadenylyl-[3'→5']-deoxycytidinyl-[3'→5'']-deoxyadenylyl-[3'→5']-deoxythymidinyl-[3'→5' ]-deoxyguanidyl-[3'→5']-deoxycytidinyl-[3'→5']-deoxyadenylyl-[3'→5']-deoxythymidinyl-[3'→5']-deoxythymidine.

HPLC (WATERS XBridge™ C18 2.5 µm 4.6×75 mm column, flow rate 1.0 mL/min, 8 mM TEA+100 mM HFIP, MeOH, gradient: 0-10 min; 5 to 60%, λ=260 nm):Rt=6.95, 7.08 min (44.3 area %+42.7 area %); TOF/MS: 3471.493

Since Reference Example 20 includes steps (1), (3), (4) and (6) in the synthesis of the above-mentioned dimer, it is one embodiment of the present invention.

Example 27: Synthesis of Phosphorothioate Dimer (5'-TT-3')

(1) Synthesis of Phosphorothioate Monomer Wherein 5'-Hydroxy Group is Protected by Anchor

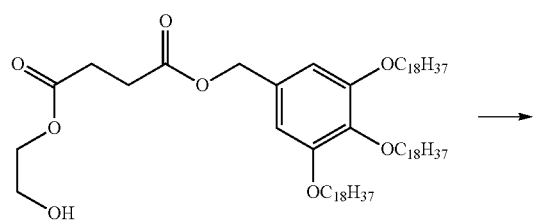

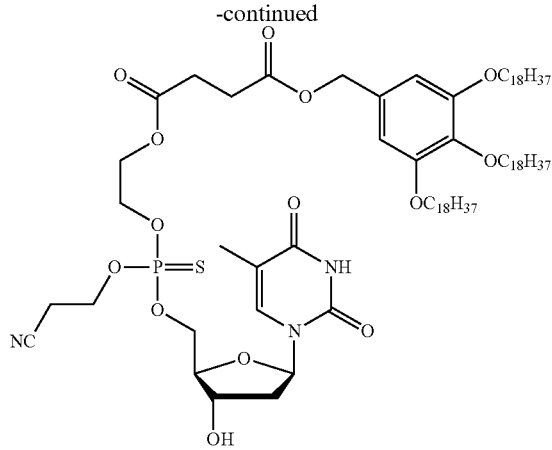

Under an argon atmosphere, in a 10 mL Schlenk tube were placed HO—(CH$_2$)$_2$-SUC-TOB (84.6 mg, 80 µmol), 3,4,5-tris(octadecyloxy)benzyl 2,2-dimethylpropanoate (84.6 mg, 84.8 µmol), and dT-5'-CE phosphoramidite (179 mg, 240 µmol), and they were dissolved in a mixed solvent of dehydrated dichloromethane (4.0 mL) and dehydrated acetonitrile (0.4 mL). To the obtained solution was added 5-ethylthio-1H-tetrazole (31.2 mg, 240 µmol), and the mixture was stirred at room temperature for 1 hr. To the reaction solution was added 2,2,2-trifluoroethanol (87.4 µL, 1.20 mmol), and the mixture was stirred at room temperature for 30 min. After stirring, 2,6-dimethylaniline (152 µL, 1.236 mmol), DDTT (51.7 mg, 252 µmol) were added, and the mixture was stirred at room temperature for 1 hr. Furthermore, 2,3-dimethylfuran (127 µL, 1.20 mmol) was added, a solution of trifluoroacetic acid (184 µL, 2.40 mmol) dissolved in dehydrated dichloromethane (368 µL) was added dropwise, and the mixture was stirred at room temperature for 1 hr. The mixture was neutralized with 2,4,6-trimethylpyridine (666 µL, 5.04 mmol), acetonitrile (17 mL) was added to the reaction solution, and the precipitated solid was collected by filtration and dried to give a monomer (5'-{[3, 4,5-tris(octadecyloxy)benzyloxy]succinyloxy-ethyl-[O-(2-cyanoethyl)]phosphorothionyl}-deoxythymidine) as a white solid (106 mg, yield 92%).

(2) Synthesis of Phosphorothioate Dimer Wherein 5'-Hydroxy Group is Protected by Anchor

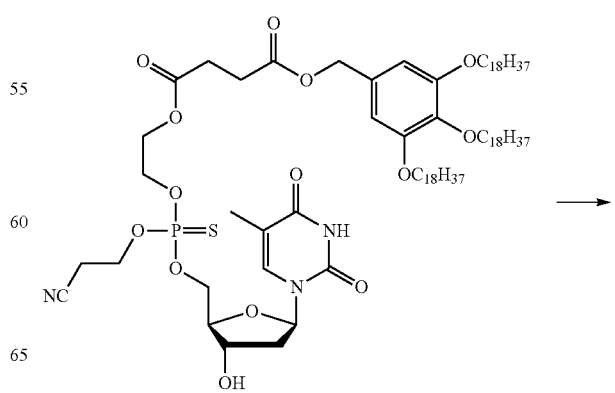

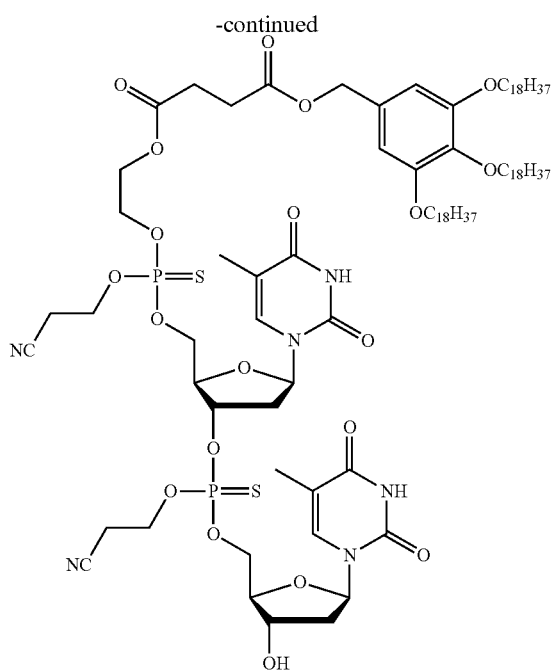

Under an argon atmosphere, in a 10 mL Schlenk tube were placed the monomer (85.9 mg, 60.0 μmol) obtained in the above-mentioned (1), 3,4,5-tris(octadecyloxy)benzyl 2,2-dimethylpropanoate (63.4 mg, 63.5 μmol), and dT-5'-CE phosphoramidite (134 mg, 180 μmol), and they were dissolved in a mixed solvent of dehydrated dichloromethane (3.0 mL) and dehydrated acetonitrile (0.3 mL). To the obtained solution was added 5-ethylthio-1H-tetrazole (23.4 mg, 180 μmol), and the mixture was stirred at room temperature for 1 hr. To the reaction solution was added 2,2,2-trifluoroethanol (65.6 μL, 900 μmol), and the mixture was stirred at room temperature for 30 min. 2,6-Dimethylaniline (114 μL, 927 μmol), DDTT (38.8 mg, 189 μmol) were added, and the mixture was stirred at room temperature for 1 hr. 2,3-Dimethylfuran (94.9 μL, 900 μmol) was added, a solution of trifluoroacetic acid (138 μL, 1.80 mmol) dissolved in dehydrated dichloromethane (276 μL) was added dropwise to the reaction solution, and the mixture was stirred at room temperature for 1 hr. 2,4,6-Trimethylpyridine (500 μL, 3.78 mmol) was added, acetonitrile (13 mL) was added to the reaction solution, and the precipitated solid was collected by filtration and dried to give a dimer (5'-{[3,4,5-tris(octadecyloxy)benzyloxy]succinyloxy-ethyl-[O-(2-cyanoethyl)]phosphorothionyl-deoxythymidine-3'-[O-(2-cyanoethyl)]phosphorothionyl}-deoxythymidine) as a white solid (107 mg, yield 99%).

(3) Deprotection

A mixture of the dimer (3.01 mg) obtained in the above-mentioned (2) and 30 wt % aqueous ammonia (5.0 mL) was placed in an autoclave, heated at 65° C. for 4 hr and cooled to room temperature. Insoluble material in the reaction solution was removed by a syringe filter (Whatman 25 mm GD/X PVDF 0.45 pin), and the filtrate was freeze-dried to give the object 5'-[O-(2-hydroxyethyl)]phosphorothionyl-deoxythymidine-3'-phosphorothionyl-deoxythymidine.

HPLC (WATERS XBridge™ C18 2.5 μm 4.6×75 mm column, flow rate 1.0 mL/min, 8 mM TEA+100 mM HFIP, MeOH, gradient: 0-10 min; 5 to 30%, λ=260 nm):Rt=1.49 min (99.3 area %); TOF/MS: 702.09

Example 28: Continuous Synthesis in Liquid without Quench (Step (2)) after Condensation (1) Synthesis Phosphorothioate Dimer Wherein 3'-Hydroxy Group is Protected by Anchor

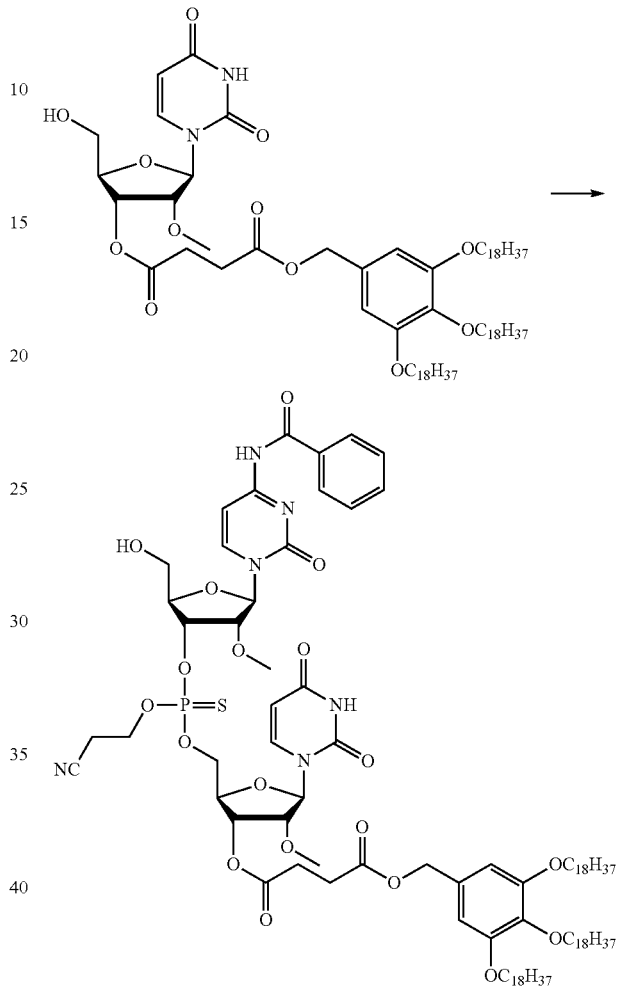

Under an argon atmosphere, in a 10 mL Schlenk tube were placed 2'-O-methyl-uridin-3'-yl-[3,4,5-tris(octadecyloxy)benzyl]succinate (104 mg, 83.3 μmol), 3,4,5-tris(octadecyloxy)benzyl 2,2-dimethylpropanoate (105 mg, 106 μmol), and Cm(Bz)-CE phosphoramidite (216 mg, 250 μmol), and they were dissolved in a mixed solvent of dehydrated dichloromethane (4.2 mL) and dehydrated acetonitrile (0.4 mL). To the obtained solution was added 5-ethylthio-1H-tetrazole (32.6 mg, 250 μmol), and the mixture was stirred at room temperature for 1 hr. To the reaction solution were added 2,6-dimethylaniline (78.8 μL, 639 μmol), DDTT (53.8 mg, 263 μmol), and the mixture was stirred at room temperature for 1 hr. 2,3-Dimethylfuran (132 μL, 1.25 mmol) was added, a solution of trifluoroacetic acid (191 μL, 2.50 mmol) dissolved in dehydrated dichloromethane (255 μL) was added dropwise, and the mixture was stirred at room temperature for 1 hr. To the reaction solution was added 2,4,6-trimethylpyridine (463 μL, 3.50 mmol), acetonitrile (18 mL) was added, and the precipitated solid was collected by filtration and dried to give a dimer ($N^4$-benzoyl-2'-O-methyl-cytidine-3'-[O-(2-cyanoethyl)]phosphorothionyl-2'-O-methyl-uridin-3'-yl-[3,4,5-tris(octadecyloxy)benzyl]succinate) as a white solid (140 mg, yield 96%).

(2) Synthesis of Phosphorothioate Trimer Wherein 3'-Hydroxy Group is Protected by Anchor

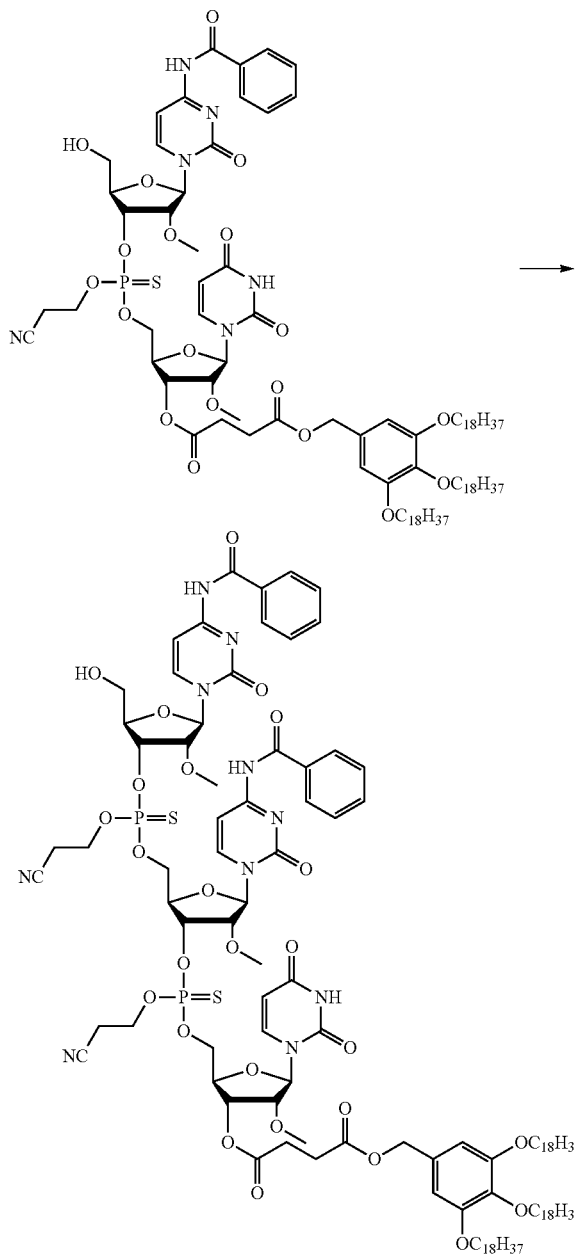

Under an argon atmosphere, in a 10 mL Schlenk tube were placed the dimer (130 mg, 74.5 μmol) obtained in the above-mentioned (1), 3,4,5-tris(octadecyloxy)benzyl 2,2-dimethylpropanoate (94.5 mg, 94.8 μmol), and Cm(Bz)-CE phosphoramidite (186 mg, 224 μmol), and they were dissolved in a mixed solvent of dehydrated dichloromethane (4.2 mL) and dehydrated acetonitrile (0.4 mL). To the obtained solution was added 5-ethylthio-1H-tetrazole (29.2 mg, 224 μmol), and the mixture was stirred at room temperature for 1 hr. To the reaction solution was added 2,6-dimethylaniline (78.8 μL, 639 μmol), DDTT (48.3 mg, 235 μmol) was added, and the mixture was stirred at room temperature for 1 hr. 2,3-Dimethylfuran (118 μL, 1.12 mmol) was added, a solution of trifluoroacetic acid (172 μL, 2.24 mmol) dissolved in dehydrated dichloromethane (255 μL) was added dropwise, and the mixture was stirred at room temperature for 1 hr. To the reaction solution was added 2,4,6-trimethylpyridine (463 μL, 3.50 mmol), acetonitrile (18 mL) was added, and the precipitated solid was collected by filtration and dried to give a trimer ($N^4$-benzoyl-2'-O-methyl-cytidine-3'-[O-(2-cyanoethyl)]phosphorothionyl-$N^4$-benzoyl-2'-O-methyl-cytidine-3'-[O-(2-cyanoethyl)]phosphorothionyl-$N^4$-benzoyl-2'-O-methyl-uridin-3'-yl-[3,4,5-tris(octadecyloxy)benzyl]succinate) as a white solid (153 mg, yield 92%).

(3) Deprotection

A mixture of the trimer (3.01 mg) obtained in the above-mentioned (2) and 30 wt % aqueous ammonia (5.0 mL) was placed in an autoclave, heated at 65° C. for 4 hr and cooled to room temperature. Insoluble material in the reaction solution was removed by a syringe filter (Whatman 25 mm GD/X PVDF 0.45 μm), and the filtrate was freeze-dried to give the object 2'-O-methyl-cytidine-3'-phosphorothionyl-2'-O-methyl-cytidine-3'-phosphorothionyl-2'-O-methyl-uridine.

HPLC (WATERS XBridge™ C18 2.5 μm 4.6×75 mm column, flow rate 1.0 mL/min, 8 mM TEA+100 mM HFIP, MeOH, gradient: 0-10 min; 5 to 30%, λ=260 nm):Rt=1.72, 1.98 min (47.9+50.6 area %); TOF/MS: 928.11

Example 29: Continuous Synthesis of Phosphorothioate Tetramer (5'-TAGT-3') in Liquid (1) Synthesis Phosphorothioate Dimer Wherein 3'-Hydroxy Group is Protected by Anchor

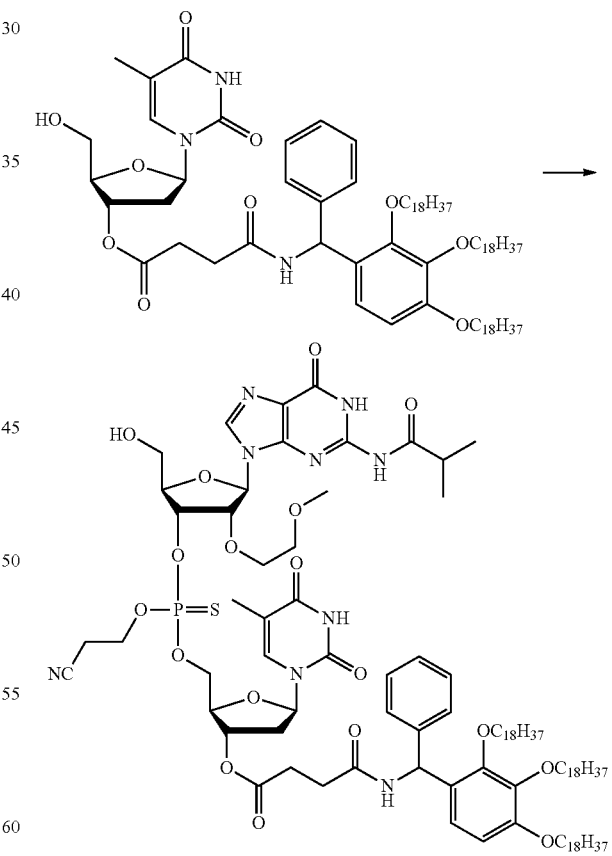

Under an argon atmosphere, in a 10 mL Schlenk tube were placed deoxythymidin-3'-yl-N-[2,3,4-tris(octadecyloxy)benzhydryl]succinamate (49.8 mg, 37.9 μmol), 3,4,5-tris(octadecyloxy)benzyl 2,2-dimethylpropanoate (49.8 mg, 49.9 μmol), and $G_{MOE}$(iBu)-CE phosphoramidite (104 mg, 114 μmol), and they were dissolved in a mixed solvent of dehydrated dichloromethane (1.9 mL) and dehydrated acetonitrile (0.6 mL) To the obtained solution was added 5-ethylthio-1H-tetrazole (14.8 mg, 114 μmol), and the mixture was stirred at room temperature for 1.5 hr. To the reaction solution was added 2,2,2-trifluoroethanol (41.4 μL, 570 μmol, and the mixture was stirred at room temperature for 30 min. After stirring, 2,6-dimethylaniline (72.2 μL, 586 μmol) and DDTT (24.5 mg, 119 μmol) was added, and the mixture was stirred at room temperature for 1 hr. Furthermore, 2,3-dimethylfuran (60.0 μL, 570 μmol) was added, a solution of trifluoroacetic acid (87.1 μL, 1.14 mmol) dissolved in dehydrated dichloromethane (174 μL) was added dropwise, and the mixture was stirred at room temperature for 1 hr. The mixture was neutralized with 2,4,6-trimethylpyridine (316 μL, 2.39 mmol), acetonitrile (8.0 mL) was added to the reaction solution, and the precipitated solid was collected by filtration and dried to give a dimer ($N^{2-}$isobutyryl-2'-O-methoxyethyl-guanosine-3'-[O-(2-cyanoethyl)]phosphorothionyl deoxythymidin-3'-yl-N-[2,3,4-tris(octadecyloxy)benzhydryl]succinamate) as a white solid (69.9 mg, yield 99%).

(2) Synthesis of Phosphorothioate Trimer Wherein 3'-Hydroxy Group is Protected by Anchor Under an argon atmosphere, in a 10 mL Schlenk tube were placed the dimer (63.5 mg, 34.2 μmol) obtained in the above-mentioned (1) and 3,4,5-tris(octadecyloxy)benzyl 2,2-dimethylpropanoate (44.9 mg, 45.0 μmol), and they were dissolved in a mixed solvent of dehydrated dichloromethane (1.7 mL) and dehydrated acetonitrile (0.5 mL). $A_{MOE}$(Bz)-CE phosphoramidite (112 mg, 120 μmol) and 5-ethylthio-1H-tetrazole (15.6 mg, 120 μmol) were added, and the mixture was stirred at room temperature for 1 hr. To the reaction solution was added 2,2,2-trifluoroethanol (43.6 μL, 595 μmol) and the mixture was stirred at room temperature for 30 min. After stirring, 2,6-dimethylaniline (75.9 μL, 571 μmol) and DDTT (25.8 mg, 126 μmol) were added and the mixture was stirred at room temperature for 1 hr. 2,3-Dimethylfuran (63.1 μL, 595 μmol) was added, a solution of trifluoroacetic acid (91.7 μL, 1.20 mmol) dissolved in dehydrated dichloromethane (183 μL) was added dropwise, and the mixture was stirred at room temperature for 1 hr. The mixture was neutralized with 2,4,6-trimethylpyridine (332 μL, 2.51 mmol), acetonitrile (8.0 mL) was added to the reaction solution, and the precipitated solid was collected by filtration and dried to give a trimer ($N^6$-benzoyl-2'O-methoxyethyl-adenosine-3'-[O-(2-cyanoethyl)]phosphorothionyl $N^2$-isobutyryl-2'-O-methoxyethyl-guanosine-3'-O-(2-cyanoethyl)]phosphorothionyl deoxythymidin-3'-yl-N-[2,3,4-tris(octadecyloxy)benzhydryl]succinamate) as a white solid (69.9 mg, yield 85%).

(3) Synthesis of Phosphorothioate Tetramer Wherein 3'-Hydroxy Group is Protected by Anchor

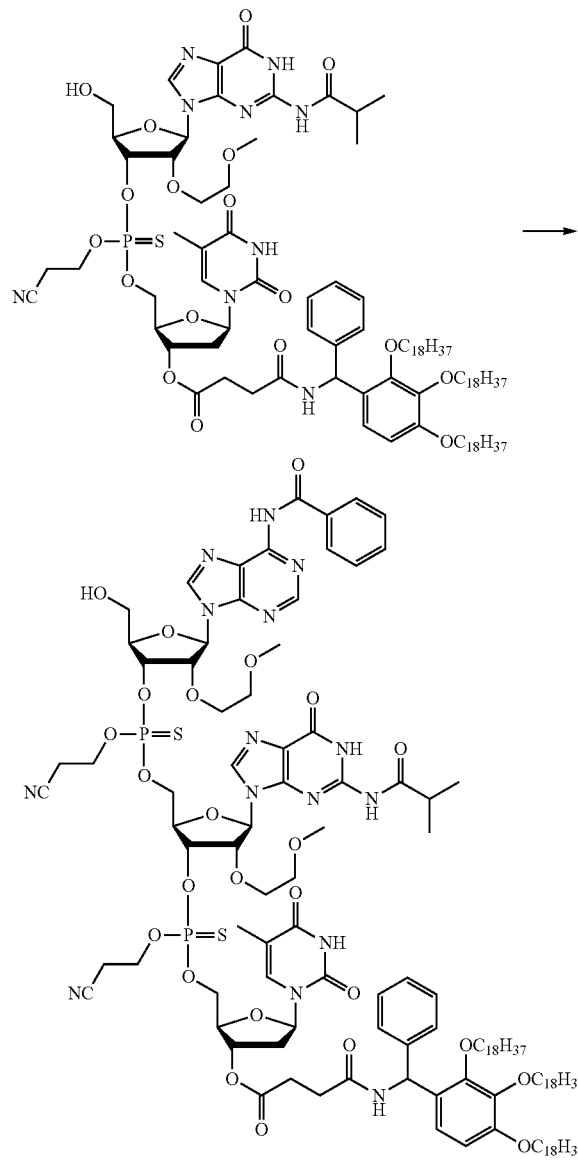

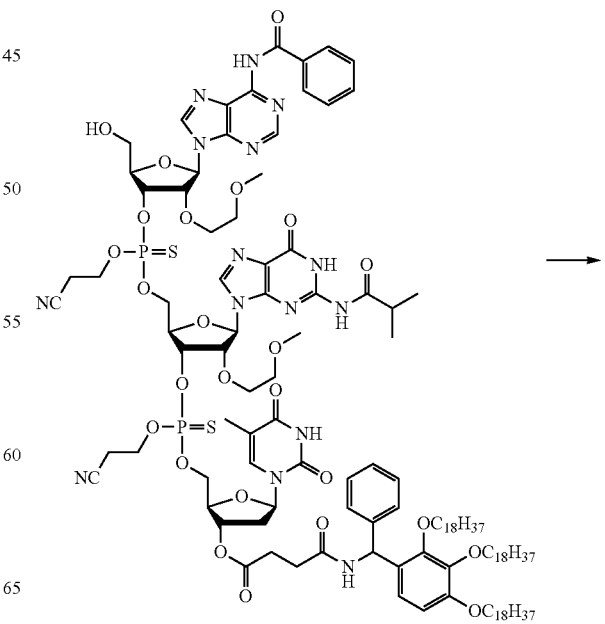

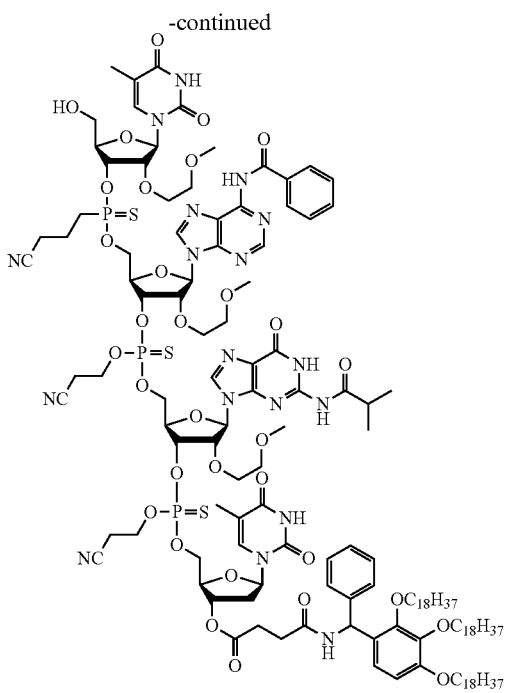

MeOH, gradient: 0-10 min; 5 to 30%, λ=260 nm):Rt=4.42, 4.49 min (31.0+66.7 area %); TOF/MS: 1458.30

Example 30: Synthesis of Trimer Using Material Wherein Nucleic Acid Base Part is Protected by Anchor (1) Synthesis of Phosphorothioate Dimer Wherein Nucleic Acid Base Part is Protected by Anchor

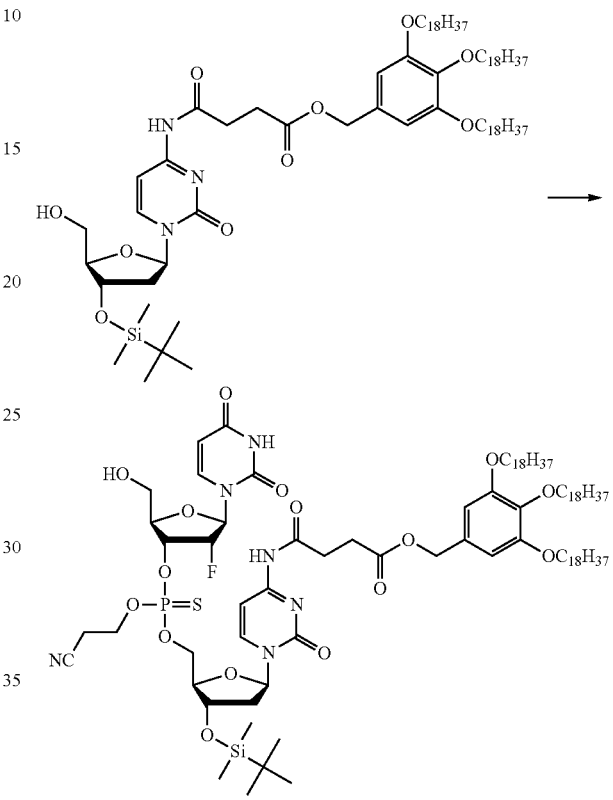

Under an argon atmosphere, in a 10 mL Schlenk tube were placed the trimer (62.7 mg, 26.0 µmol) obtained in the above-mentioned (2) and 3,4,5-tris(octadecyloxy)benzyl 2,2-dimethylpropanoate (34.0 mg, 34.1 µmol), and they were dissolved in a mixed solvent of dehydrated dichloromethane (1.3 mL) and dehydrated acetonitrile (0.4 mL). $T_{MOE}$-CE phosphoramidite (63.8 mg, 78.0 µmol) and 5-ethylthio-1H-tetrazole (10.1 mg, 78.0 µmol) were added, and the mixture was stirred at room temperature for 1 hr. To the reaction solution was added 2,2,2-trifluoroethanol (28.4 µL, 390 µmol), and the mixture was stirred at room temperature for 30 min. After stirring, 2,6-dimethylaniline (49.4 µL, 401 µmol) and DDTT (16.8 mg, 82.0 mol) were added, and the mixture was stirred at room temperature for 1 hr. 2,3-Dimethylfuran (41.0 µL, 390 mol) was added, a solution of trifluoroacetic acid (59.6 µL, 780 µmol) dissolved in dehydrated dichloromethane (119 µL) was added dropwise, and the mixture was stirred at room temperature for 1 hr. 2,4,6-Trimethylpyridine (216 µL, 1.64 mmol), water (2 µL) were added, and the mixture was stirred at room temperature for 1 hr. To the reaction solution was added acetonitrile (6 mL), and the precipitated solid was collected by filtration and dried to give a tetramer (2'-O-methoxyethyl-thymidine-3'-[O-(2-cyanoethyl)]phosphorothionyl N$^6$-benzoyl-2'-O-methoxyethyl-adenosine-3'-[O-(2-cyanoethyl)]phosphorothionyl N$^2$-isobutyryl-2'-O-methoxyethyl-guanosine-3'-[O-(2-cyanoethyl)]phosphorothionyl deoxythymidin-3'-yl-N-[2,3,4-tris(octadecyloxy)benzhydryl]succinamate) as a white solid (58.9 mg, yield 79.2%).

(4) Deprotection

A mixture of the tetramer (3.10 mg) obtained in the above-mentioned (3) and 30 wt % aqueous ammonia (5.0 mL) was placed in an autoclave, heated at 65° C. for 4 hr and cooled in an ice bath. Insoluble material in the reaction solution was removed by a syringe filter (Whatman 25 mm GD/X PVDF 0.45 µm), and the filtrate was freeze-dried to give the object 2'-O-methoxyethyl-thymidine-3'-phosphorothionyl-2'-O-methoxyethyl-adenosine-3'-phosphorothionyl-2'-O-methoxyethyl-guanosine-3'-phosphorothionyl-deoxythymidine.

HPLC (WATERS XBridge™ C18 2.5 µm 4.6×75 mm column, flow rate 1.0 mL/min, 8 mM TEA+100 mM HFIP, Under an argon atmosphere, in a 10 mL Schlenk tube were placed N$^4$-[3,4,5-tris(octadecyloxy)benzyloxy]succinyl-3'-O-(1,1-dimethylethyl)dimethylsilyl-deoxycytidine (100 mg, 80.0 µmol), 3,4,5-tris(octadecyloxy)benzyl 2,2-dimethylpropanoate (100 mg, 100 prol), and 2'F—U-CE phosphoramidite (180 mg, 240 µmol), and they were dissolved in a mixed solvent of dehydrated dichloromethane (4.0 mL) and dehydrated acetonitrile (0.4 mL). To the obtained solution was added 5-ethylthio-1H-tetrazole (31.2 mg, 240 µmol), and the mixture was stirred at room temperature for 1 hr. To the reaction solution was added 2,2,2-trifluoroethanol (87.4 µL, 1.20 mmol), and the mixture was stirred at room temperature for 30 min. After stirring, 2,6-dimethylaniline (152 µL, 1.24 mmol), DDTT (51.7 mg, 252 µmol) were added, and the mixture was stirred at room temperature for 1 hr. Furthermore, 2,3-dimethylfuran (127 µL, 1.20 mmol) was added, a mixed solution of trifluoroacetic acid (184 µL, 2.40 mmol) and 2,6-dimethylaniline (3.0 µL, 20 µmol) dissolved dehydrated dichloromethane (368 µL) was added dropwise, and the mixture was stirred at room temperature for 1 hr. To the reaction solution was added 2,4,6-trimethylpyridine (666 µL, 5.04 mmol), acetonitrile (17 mL) was added, and the precipitated solid was collected by filtration and dried to give a dimer (2'-fluorouridine-3'-[O-(2-cyanoethyl)]phosphorothionyl N$^4$-[3,4,5-tris(octadecyloxy)benzyloxy]succinyl-3'-O-(1,1-dimethylethyl)dimethylsilyl-deoxycytidine) as a white solid (127 mg, yield 98%)

(2) Synthesis of Phosphorothioate Trimer Wherein Nucleic Acid Base Part is Protected by Anchor

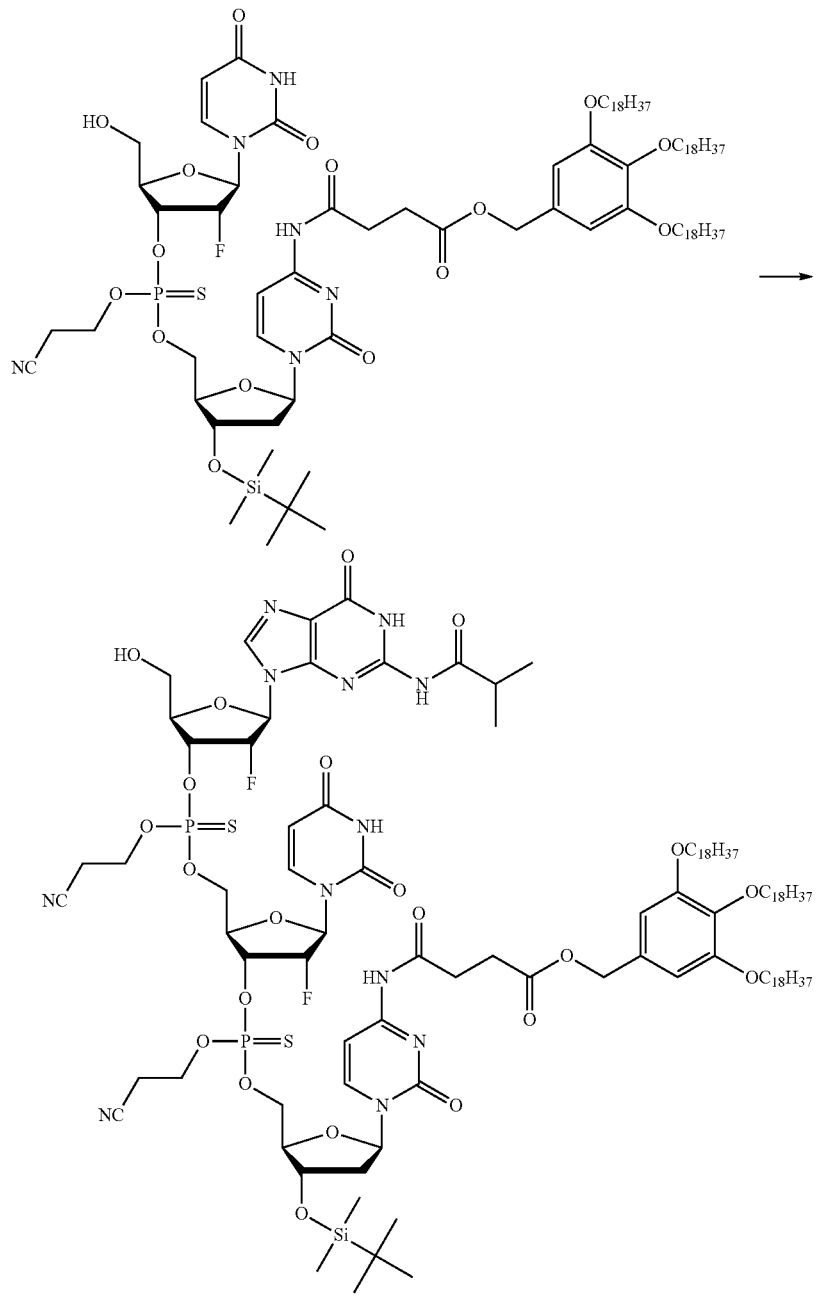

Under an argon atmosphere, in a 10 mL Schlenk tube were placed the dimer (114 mg, 70.0 μmol) obtained in the above-mentioned (1), 3,4,5-tris(octadecyloxy)benzyl 2,2-dimethylpropanoate (87.5 mg, 87.7 μmol) and 2'F-G-CE phosphoramidite (180 mg, 210 μmol), and they were dissolved in a mixed solvent of dehydrated dichloromethane (3.5 mL) and dehydrated acetonitrile (0.3 mL). To the obtained solution was added 5-ethylthio-1H-tetrazole (27.3 mg, 210 μmol), and the mixture was stirred at room temperature for 1 hr. To the reaction solution was added 2,2,2-trifluoroethanol (76.5 μL, 1.05 mmol), and the mixture was stirred at room temperature for 30 min. After stirring, 2,6-dimethylaniline (133 μL, 1.08 mmol), DDTT (45.3 mg, 220 μmol) were added, and the mixture was stirred at room temperature for 1 hr. Furthermore, 2,3-dimethylfuran (111 μL, 1.05 mmol) was added, a mixed solution of trifluoroacetic acid (161 μL, 2.10 mmol) and 2,6-dimethylaniline (2.6 μL, 20 μmol) dissolved in dehydrated dichloromethane (321 μL) was added dropwise, and the mixture was stirred at room temperature for 1 hr. To the reaction solution was added 2,4,6-trimethylpyridine (583 μL, 4.41 mmol), acetonitrile (15 mL) was added, and the precipitated solid was collected by filtration and dried to give a trimer ($N^2$-isobutyryl-2'-fluoro-guanosine-3'-[O-(2-cyanoethyl)]phosphorothionyl 2'-fluoro-uridine-3'-[O-(2-cyanoethyl)]phosphorothionyl $N^4$-[3,4,5-tris(octadecyloxy)benzyloxy]succinyl-3'-O-(1,1-dimethylethyl)dimethylsilyl-deoxycytidine) as a white solid (139 mg, yield 94%).

(3) Removal of Silyl-Protecting Group of 3'-Hydroxy Group

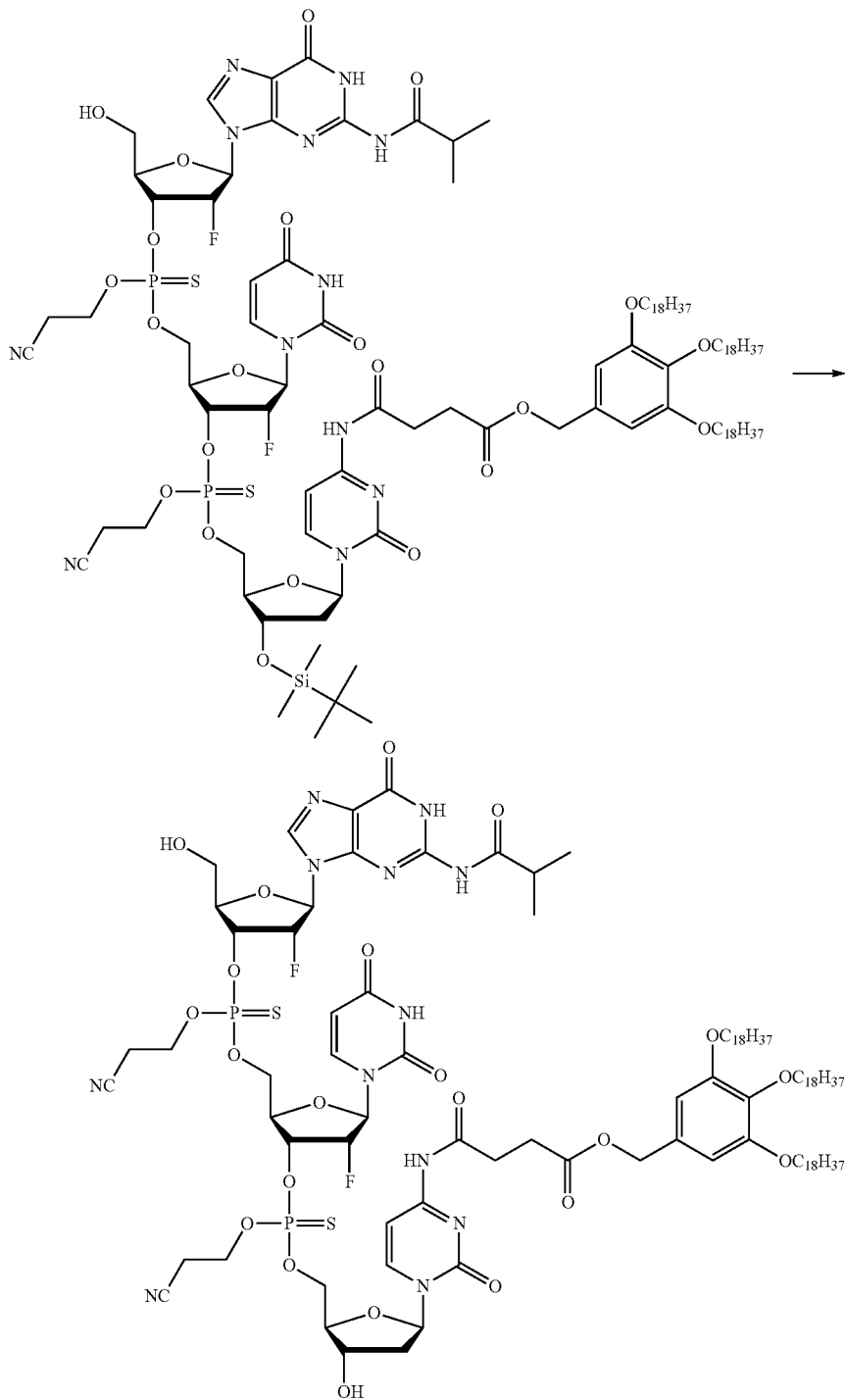

In a 10 mL Schlenk tube were placed the dimer (110 mg, 50.0 µmol) obtained in the above-mentioned (2) and 3,4,5-tris(octadecyloxy)benzyl 2,2-dimethylpropanoate (62.5 mg, 62.6 µmol), and they were dissolved in a mixed solvent of dichloromethane (2.0 mL) and tetrahydrofuran (4.0 mL). To the obtained solution were added triethylamine trihydrofluoride (196 µL, 1.20 mmol) and pyridine (193 µL, 2.40 mmol), and the mixture was stirred at room temperature for 16 hr. To the reaction solution was added acetonitrile (20 mL), and the precipitated solid was collected by filtration and dried to give a trimer ($N^2$-isobutyryl-2'-fluoro-guanosine-3'-[O-(2-cyanoethyl)]phosphorothionyl 2'-fluoro-uridine-3'-[O-(2-cyanoethyl)]phosphorothionyl $N^4$-[3,4,5-tris(octadecyloxy)benzyloxy]succinyl-deoxycytidine) as a white solid (100 mg, yield 96%).

(4) Deprotection

A mixture of the trimer (3.12 mg) obtained the above-mentioned (3) and 30 wt % aqueous ammonia (5.0 mL) was placed in an autoclave, heated at 65° C. for 4 hr and cooled to room temperature. Insoluble material in the reaction solution was removed by a syringe filter (Whatman 25 mm GD/X PVDF 0.45 µm), and the filtrate was freeze-dried to give the object 2'-fluoro-guanosine-3'-phosphorothionyl-2'-fluoro-uridine-3'-phosphorothionyl-deoxycytidine.

HPLC (WATERS XBridge™ C18 2.5 µm 4.6×75 mm column, flow rate 1.0 mL/min, 8 mM TEA+100 mM HFIP, MeOH, gradient: 0-10 min; 5 to 30%, λ=260 nm):Rt=1.15, 1.40 min (11.2+85.1 area %); TOF/MS: 914.11

Example 31: Synthesis of Phosphorothioate Trimer (1) Synthesis of Phosphorothioate Dimmer Wherein 3'-Hydroxy Group is Protected by Anchor

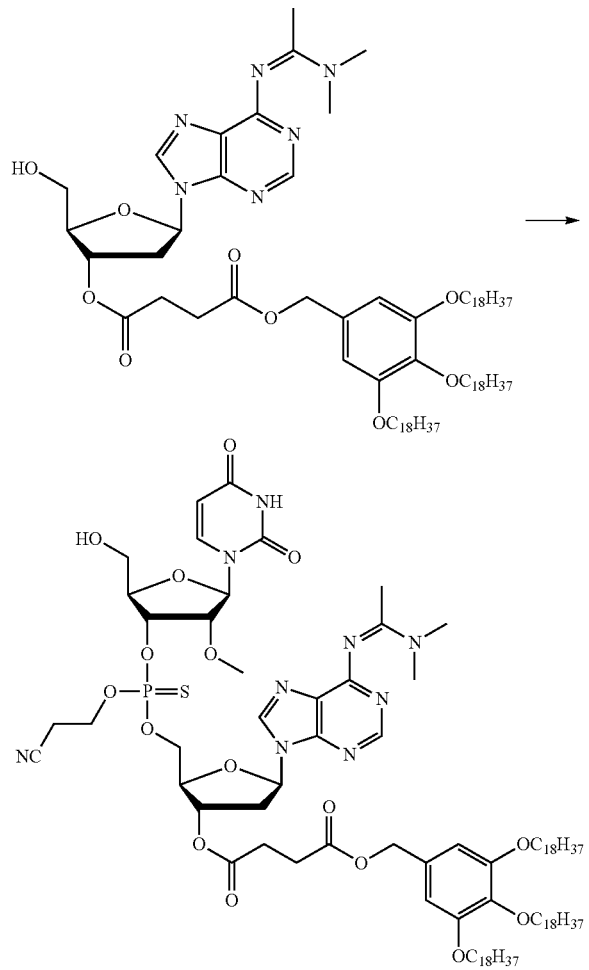

Under an argon atmosphere, in a 10 mL Schlenk tube were placed N⁶-[1-(dimethylamino)ethylidene]-deoxyadenosin-3'-yl-[3,4,5-tris(octadecyloxy)benzyl]succinate (105 mg, 80.0 µmol), 3,4,5-tris(octadecyloxy)benzyl 2,2-dimethylpropanoate (105 mg, 106 µmol), and U-CE phosphoramidite (183 mg, 240 µmol), and they were dissolved in a mixed solvent of dehydrated dichloromethane (4.0 mL) and dehydrated acetonitrile (0.4 mL). To the obtained solution was added 5-ethylthio-1H-tetrazole (31.2 mg, 240 µmol), and the mixture was stirred at room temperature for 1 hr. To the reaction solution was added 2,2,2-trifluoroethanol (87.4 µL, 1.20 mmol), and the mixture was stirred at room temperature for 30 min. 2,6-Dimethylaniline (152 µL, 1.24 mmol) and DDTT (51.7 mg, 252 µmol) were added, and the mixture was stirred at room temperature for 1 hr. Furthermore, 2,3-dimethylfuran (127 µL, 1.20 mmol) was added, a solution of trifluoroacetic acid (184 µL, 2.40 mmol) dissolved in dehydrated dichloromethane (368 µL) was added dropwise, and the mixture was stirred at room temperature for 1 hr. To the reaction solution was added 2,4,6-trimethylpyridine (666 µL, 5.04 mmol), acetonitrile (17 mL) was added, and the precipitated solid was collected by filtration and dried to quantitatively give a dimer (2'-O-methyl-uridine-3'-[O-(2-cyanoethyl)]phosphorothionyl N⁶-[1-(dimethylamino)ethylidene]-deoxyadenosin-3'-yl-[3,4,5-tris(octadecyloxy)benzyl]succinate) as a white solid.

(2) Synthesis of Phosphorothioate Trimer Wherein 3'-Hydroxy Group is Protected by Anchor

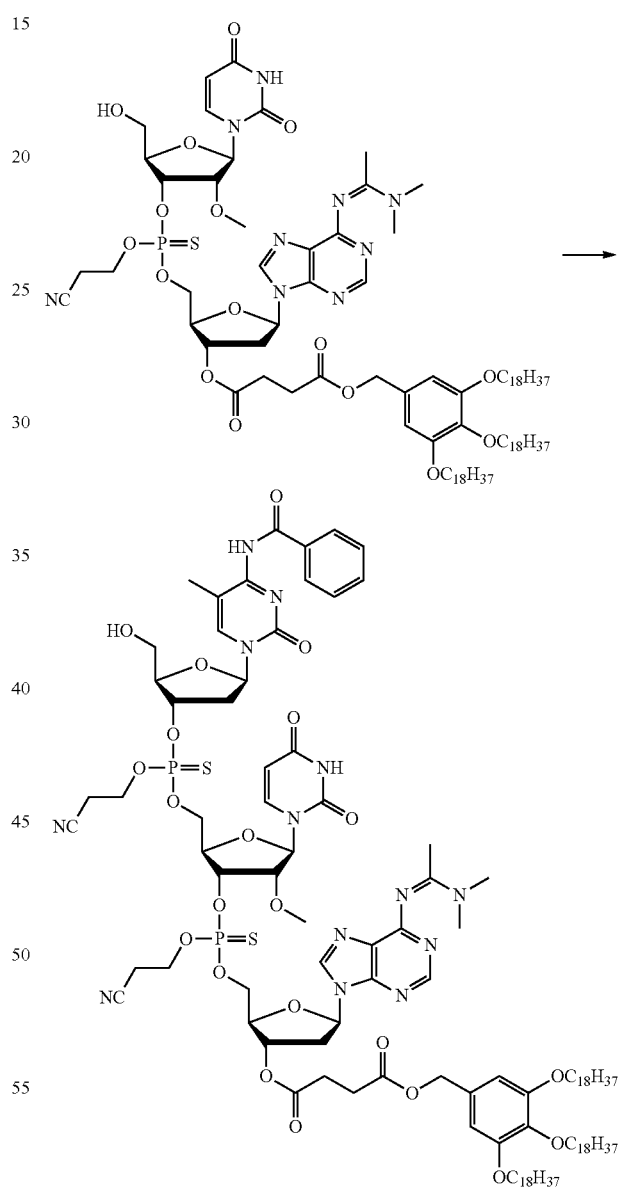

Under an argon atmosphere, in a 10 mL Schlenk tube were placed the compound (119 mg, 70.0 µmol) obtained in the above-mentioned (1), 3,4,5-tris(octadecyloxy)benzyl 2,2-dimethylpropanoate (92.2 mg, 92.4 µmol) and N⁴-benzoyl-5-Me-dC-CE phosphoramidite (178 mg, 210 µmol), and they were dissolved in a mixed solvent of dehydrated dichloromethane (4.0 mL) and dehydrated acetonitrile (0.4 mL). To the obtained solution was added 5-ethylthio-1H-tetrazole (27.3 mg, 210 μmol), and the mixture was stirred at room temperature for 1 hr. To the reaction solution was added 2,2,2-trifluoroethanol (76.5 μL, 1.05 mmol), and the mixture was stirred at room temperature for 30 min. 2,6-Dimethylaniline (133 μL, 1.08 mol) and DDTT (45.3 mg, 221 μmol) were added, and the mixture was stirred at room temperature for 1 hr. Furthermore, 2,3-dimethylfuran (111 μL, 1.05 mmol) was added, a solution of trifluoroacetic acid (161 μL, 2.10 mmol) dissolved in dehydrated dichloromethane (322 μL) was added dropwise, and the mixture was stirred at room temperature for 1 hr. To the reaction solution was added 2,4,6-trimethylpyridine (583 μL, 4.41 mmol), acetonitrile (17 mL) was added, and the precipitated solid was collected by filtration and dried to give a trimer ($N^4$-benzoyl-5-methyl-deoxycytidine-3'-[O-(2-cyanoethyl)]phosphorothionyl 2'-O-methyl-uridine-3'-[O-(2-cyanoethyl)]phosphorothionyl $N^6$-[1-(dimethylamino)ethylidene]-deoxyadenosin-3'-yl-[3,4,5-tris(octadecyloxy)benzyl]succinate) as a white solid (131 mg, yield 85%)

(3) Deprotection

A mixture of the trimer (3.02 mg) obtained in the above-mentioned (2) and 30 wt % aqueous ammonia (5.0 mL) was placed in an autoclave, heated at 65° C. for 4 hr and cooled to room temperature. Insoluble material in the reaction solution was removed by a syringe filter (Whatman 25 mm GD/X PVDF 0.45 μm), and the filtrate was freeze-dried to give the object 5-methyl-deoxycytidine-3'-phosphorothionyl-2'-O-methyl-uridine-3'-phosphorothionyl-deoxyadenosine.

HPLC (WATERS XBridge™ C18 2.5 μm 4.6×75 mm column, flow rate 1.0 mL/min, 8 mM TEA+100 mM HFIP, MeOH, gradient: 0-10 min; to 30%, λ=260 nm):Rt=1.92, 2.23 min (14.8+75.6 area %); TOF/MS: 906.17

INDUSTRIAL APPLICABILITY

According to the production method of the oligonucleotide of the present invention, condensation can be performed efficiently. The oligonucleotide obtained by the production method of the present invention can be used for various applications such as pharmaceutical products (RNA, DNA, oligonucleic acid medicine etc.) for human or animal, functional food, food for specified health uses, food, chemical product, polymer material for living body or industrial use, and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

We claim:

1. A method for producing an oligonucleotide, comprising:
   (1) condensing, in a non-polar solvent,
   a nucleoside, nucleotide or oligonucleotide (b), and
   a nucleoside, nucleotide or oligonucleotide (a), or
   a substituted nucleotide or oligonucleotide (α)
   by adding said nucleoside, nucleotide or oligonucleotide (b) to a reaction solution comprising said nucleoside, nucleotide or oligonucleotide (a) or said substituted nucleotide or oligonucleotide (α) to obtain a reaction solution comprising a phosphite triester product (c) wherein a 5'-hydroxy group is protected by a temporary protecting group;
   (3) oxidizing or sulfurizing said phosphite triester product (c) by adding an oxidant or a sulfurizing agent to said reaction solution comprising said phosphite triester product (c) to obtain a reaction solution comprising an oligonucleotide (d) wherein the 5'-hydroxy group is protected by the temporary protecting group;

(4) removing the temporary protecting group of the 5'-hydroxy group by adding an acid to said reaction solution after the oxidation or sulfurization to obtain a reaction solution comprising an oligonucleotide (e) wherein the 5'-hydroxy group is not protected; and (6) adding a polar solvent to said reaction solution comprising said oligonucleotide (e) and purifying said oligonucleotide (e) by solid-liquid separation, wherein said non-polar solvent is at least one member selected from the group consisting of chloroform, dichloromethane, 1,2-dichloroethane, benzene, toluene, xylene, mesitylene, ethyl acetate, isopropyl acetate, hexane, pentane, heptane, octane, nonane, cyclohexane, diethyl ether, cyclopentyl methyl ether, tert-butyl methyl ether, and mixtures thereof;

wherein said nucleoside, nucleotide or oligonucleotide (a) or said substituted nucleotide or oligonucleotide (a) is a compound represented by formula (a-i):

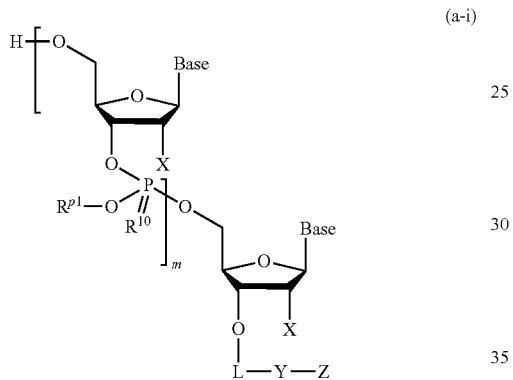

wherein m is an integer of not less than 0 and not more than 49;

each Base in each number of m+1 is independently an optionally protected nucleic acid base;

each X in each number of m+1 is independently a hydrogen atom, a halogen atom, or an optionally protected hydroxy group;

each $R^{10}$ in each number of m is independently an oxygen atom or a sulfur atom;

each $R^{p1}$ in each number of m is independently a protecting group of phosphoric acid group;

L is a single bond, or a group represented by formula (a1) or (a1'):

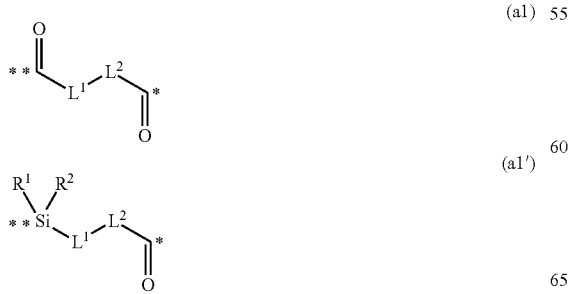

wherein

* is the bonding position to Y;

** is the bonding position to an oxygen atom;

$R^1$ and $R^2$ are each independently a $C_{1-22}$ hydrocarbon group;

$L^1$ is an optionally substituted divalent $C_{1-22}$ hydrocarbon group;

$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;

Y is a single bond, an oxygen atom or NR wherein R is a hydrogen atom, an alkyl group or an aralkyl group; and Z is a group represented by formula (a2), formula (a2') or formula (a2"):

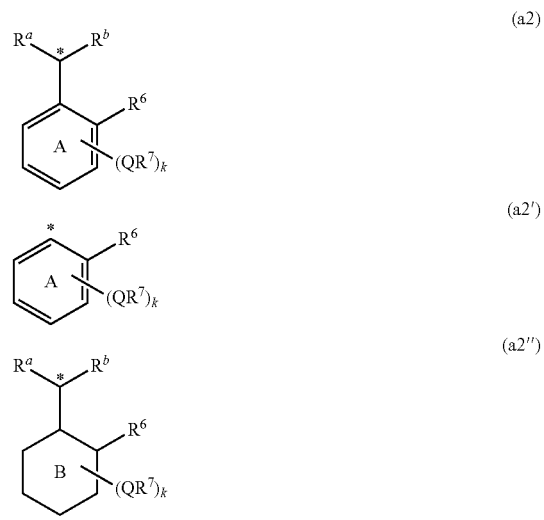

wherein

* indicates a bonding position;

$R^6$ is a hydrogen atom, or when $R^b$ is a group represented by the following formula (a3), $R^6$ of ring A or ring B is optionally shows, together with $R^8$, a single bond or —O— to form, together with ring A or ring B and ring C, a fused ring;

k is an integer of 1 to 4;

each Q in each number of k is independently —O—, —C(=O)—, —C(=O)O—, —OC(=O)—, —C(=O)NH— or —NHC(=O)—;

each $R^7$ in each number of k is independently a hydrocarbon group wherein a linear aliphatic hydrocarbon group selected from a linear $C_{10-40}$ alkyl group and a linear $C_{10-40}$ alkenyl group is bonded via a single bond or a linker;

ring A and ring B, each independently, optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;

$R^a$ is a hydrogen atom; and $R^b$ is a hydrogen atom, or a group represented by formula (a3):

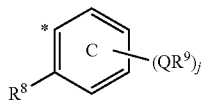

(a3)

wherein

* indicates a bonding position;

j is an integer of 0 to 4;

each Q in each number of j is independently as defined above;

each $R^9$ in each number of j is independently a hydrocarbon group wherein a linear aliphatic hydrocarbon group selected from a linear $C_{10\text{-}40}$ alkyl group and a linear $C_{10\text{-}40}$ alkenyl group is bonded via a single bond or a linker;

$R^8$ is a hydrogen atom, or optionally shows, together with $R^6$ of ring A or ring B, a single bond or —O— to form, together with ring A or ring B and ring C, a fused ring; and ring C optionally has, in addition to $QR^9$ in the number of j, a substituent selected from the group consisting of a halogen atom, a $C_{1\text{-}6}$ alkyl group optionally substituted by a halogen atom, and a $C_{1\text{-}6}$ alkoxy group optionally substituted by a halogen atom, or $R^a$ and $R^b$ are joined to form an oxo group;

a compound represented by formula (a-vi):

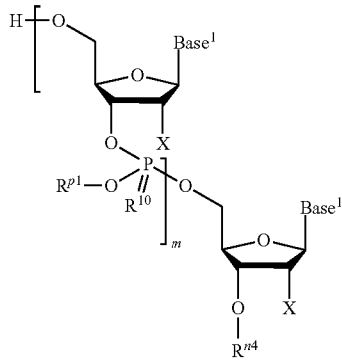

(a-vi)

wherein at least one of Base' in the number of m+1 is a nucleic acid base protected by -L-Y—Z, and the rest is an optionally protected nucleic acid base;

$R''^4$ is a hydroxy-protecting group;

m, X in the number of m+1, $R^{10}$ in the number of m, $R^{p1}$ in the number of m, L, Y and Z are each independently as defined above; or a compound represented by formula (a-vii):

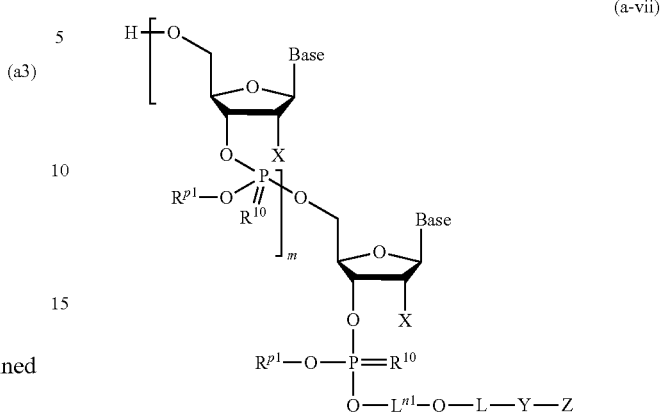

(a-vii)

wherein $L^{n1}$ is a $C_{2\text{-}6}$ alkylene group;

m, Base in the number of m+1, X in the number of m+1, $R^{10}$ in the number of m+1, $R^{p1}$ in the number of m+1, L, Y and Z are each independently as defined above;

wherein said nucleoside, nucleotide or oligonucleotide (b) is a compound represented by formula (b-i):

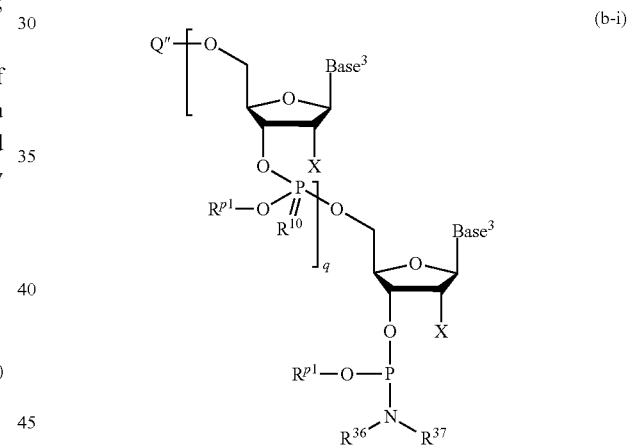

(b-i)

wherein q is an integer of not less than 0 and not more than 49;

each $Base^3$ in each number of q+1 is independently an optionally protected nucleic acid base;

X in the number of q+1, $R^{p1}$ in the number of q+1, and $R^{10}$ in the number of q are each independently as defined above;

Q" is the temporary protecting group;

$R^{36}$ and $R^{37}$ are each independently an alkyl group, or a 5- or 6-membered saturated cyclic amino group formed together with the adjacent nitrogen atom, and the saturated cyclic amino group, optionally has, as a ring-constituting atom, one oxygen atom or sulfur atom besides nitrogen atom;

wherein said temporary protecting group is a trityl group, a 9-(9-phenyl)xanthenyl group, a 9-phenylthioxanthenyl group, a bis($C_{1\text{-}6}$ alkoxy)trityl group, or a mono ($C_{1\text{-}18}$ alkoxy)trityl group;

wherein said acid in said (4) removing the temporary protecting group is at least one member selected from the group consisting of trifluoroacetic acid, dichloroacetic acid, trifluoromethanesulfonic acid, trichloroacetic acid, methanesulfonic acid, hydrochloric acid, acetic acid, p-toluenesulfonic acid, and mixtures thereof; and wherein said polar solvent in said (6) adding a polar solvent to said reaction solution is at least one member selected from the group consisting of methanol, ethanol, isopropanol, acetonitrile, propionitrile, acetone, 2-butanone, 1,4-dioxane, tetrahydrofuran, dimethylformamide, dimethylacetamide, N-methylpiperidone, dimethyl sulfoxide, water, and mixtures thereof.

2. The method according to claim 1, further comprising:
(2) adding a quencher to the reaction solution after condensation, after said (1) condensing and before said (3) oxidizing or sulfurizing.

3. The method according to claim 2, wherein said quencher is at least one member selected from the group consisting of an alcohol, a phenol, amine, and mixtures thereof.

4. The method according to claim 1, wherein a mixture of a carboxylic acid and an organic base, an inorganic acid or an amine is added to said reaction solution after said (1) condensing and before said (4) removing the temporary protecting group, and 5-[(N,N-dimethylaminomethylidene)amino]-3H-1,2,4-dithiazole-3-thione is added to said reaction solution as a sulfurizing agent in said (3) oxidizing or sulfurizing.

5. The method according to claim 4, wherein an amount of a basic nitrogen atom of said organic base is 1 to 2 mol per 1 mol of carboxy group of said carboxylic acid.

6. The method according to claim 1, wherein said sulfurizing agent in said (3) oxidizing or sulfurizing is at least one member selected from the group consisting of 3H-1,2-benzodithiol-3-one-1,1-dioxide, 3H-1,2-benzodithiol-3-one, phenylacetyl disulfide, tetraethylthiuram disulfide, dipentamethylenethiuram tetrasulfide, phenyl-3H-1,2,4-dithiazol-3-one, 3-amino-1,2,4-dithiazole-5-thione, sulfur, and mixtures thereof.

7. The method according to claim 1, wherein said oxidant in said (3) oxidizing or sulfurizing is at least one member selected from the group consisting of iodine, (1S)-(+)-(10-camphanylsulfonyl)oxaziridine, tert-butyl hydroperoxide, 2-butanone peroxide, 1,1-dihydroperoxycyclododecane, bis(trimethylsilyl)peroxide, m-chloroperbenzoic acid, and mixtures thereof.

8. The method according to claim 1, wherein said temporary protecting group is a dimethoxytrityl group or a monomethoxytrityl group.

9. The method according to claim 1, wherein said polar solvent in said (6) adding a polar solvent to said reaction solution is at least one member selected from the group consisting of acetonitrile, propionitrile, and mixtures thereof.

10. The method according to claim 1, further comprising:
(5) neutralizing said reaction solution comprising said oligonucleotide (e) by adding a base, after said (4) removing the temporary protecting group and before said (6) adding a polar solvent to said reaction solution.

11. The method according to claim 10, wherein said base in said (5) neutralizing said reaction solution comprising said oligonucleotide (e) by adding a base is at least one member selected from the group consisting of pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole, 5-nitrobenzimidazole, and mixtures thereof.

12. The method according to claim 1, further comprising:
(7) removing all protecting groups of the obtained oligonucleotide and isolating an unprotected oligonucleotide, after said (6) adding a polar solvent to said reaction solution.

13. The method according to claim 1, wherein said (4) removing the temporary protecting group is performed in the presence of a cation scavenger, or the method further comprises adding a cation scavenger to the reaction solution after the reaction to remove the temporary protecting group.

14. The method according to claim 13, wherein said cation scavenger is at least one member selected from the group consisting of pyrrole, 2-methylpyrrole, 3-methylpyrrole, 2,3-dimethylpyrrole, 2,4-dimethylpyrrole, indole, 3-methylindole, 4-methylindole, 5-methylindole, 6-methylindole, 7-methylindole, 5,6-dimethylindole, 6,7-dimethylindole, 2-methylfuran, 2,3-dimethylfuran, 2-methyl-3-(methylthio)furan, menthofuran, and mixtures thereof.

15. A method for producing an oligonucleotide, comprising:

(1') condensing, in a non-polar solvent, a nucleoside, nucleotide or oligonucleotide (b'), and a nucleoside, nucleotide or oligonucleotide (a'), or a substituted nucleotide or oligonucleotide (α')

by adding said nucleoside, nucleotide or oligonucleotide (b') to a reaction solution comprising said nucleoside, nucleotide or oligonucleotide (a') or said substituted nucleotide or oligonucleotide (α') to obtain a reaction solution comprising a phosphite triester product (c') wherein a 3'-hydroxy group is protected by a temporary protecting group;

(3') oxidizing or sulfurizing said phosphite triester product (c') by adding an oxidant or a sulfurizing agent to said reaction solution comprising said phosphite triester product (c') to obtain a reaction solution comprising an oligonucleotide (d') wherein the 3'-hydroxy group is protected by the temporary protecting group;

(4') removing the temporary protecting group of the 3'-hydroxy group by adding an acid to said reaction solution after the oxidation or sulfurization to obtain a reaction solution comprising an oligonucleotide (e') wherein the 3'-hydroxy group is not protected; and (6') adding a polar solvent to said reaction solution comprising said oligonucleotide (e') and purifying said oligonucleotide (e') by solid-liquid separation, wherein said non-polar solvent is at least one member selected from the group consisting of chloroform, dichloromethane, 1,2-dichloroethane, benzene, toluene, xylene, mesitylene, ethyl acetate, isopropyl acetate, hexane, pentane, heptane, octane, nonane, cyclohexane, diethyl ether, cyclopentyl methyl ether, tert-butyl methyl ether, and mixtures thereof;

wherein said nucleoside, nucleotide or oligonucleotide (a') or said substituted nucleotide or oligonucleotide (α') is a compound represented by formula (a-i'):

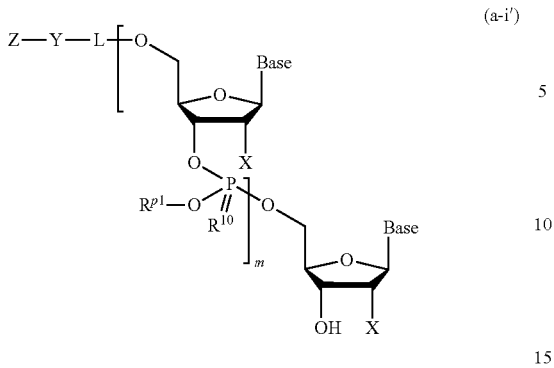

(a-i')

wherein
- m is an integer of not less than 0 and not more than 49;
- each Base in each number of m+1 is independently an optionally protected nucleic acid base;
- each X in each number of m+1 is independently a hydrogen atom, a halogen atom, or an optionally protected hydroxy group;
- each $R^{10}$ in each number of m is independently an oxygen atom or a sulfur atom;
- each $R^{p1}$ in each number of m is independently is a protecting group of phosphoric acid group;
- L is a single bond, or a group represented by formula (a1) or (a1'):

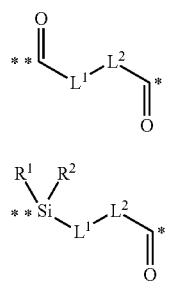

(a1)

(a1')

wherein
- * is the bonding position to Y;
- ** is the bonding position to an oxygen atom;
- $R^1$ and $R^2$ are each independently a $C_{1-22}$ hydrocarbon group;
- $L^1$ is an optionally substituted divalent $C_{1-22}$ hydrocarbon group;
- $L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
- Y is a single bond, an oxygen atom or NR wherein R is a hydrogen atom, an alkyl group or an aralkyl group; and
- Z is a group represented by formula (a2), formula (a2') or formula (a2"):

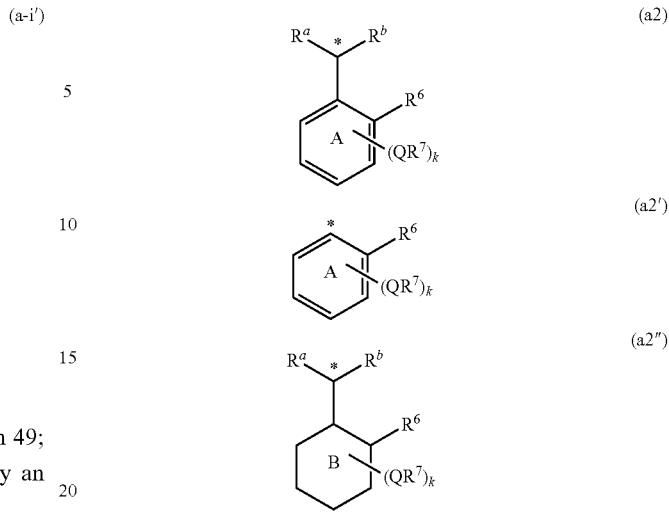

(a2)

(a2')

(a2")

wherein
- * indicates a bonding position;
- $R^6$ is a hydrogen atom, or when $R^b$ is a group represented by the following formula (a3), $R^6$ of ring A or ring B is optionally shows, together with $R^8$, a single bond or —O— to form, together with ring A or ring B and ring C, a fused ring;
- k is an integer of 1 to 4;
- each Q in each number of k is independently —O—, —C(=O)—, —C(=O)O—, —OC(=O)—, —C(=O)NH— or —NHC(=O)—;
- each $R^7$ in each number of k is independently a hydrocarbon group wherein a linear aliphatic hydrocarbon group selected from a linear $C_{10-40}$ alkyl group and a linear $C_{10-40}$ alkenyl group is bonded via a single bond or a linker;
- ring A and ring B, each independently, optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;
- $R^a$ is a hydrogen atom; and
- $R^b$ is a hydrogen atom, or a group represented by formula (a3):

(a3)

wherein
- * indicates a bonding position;
- j is an integer of 0 to 4;
- each Q in each number of j is independently as defined above;
- each $R^9$ in each number of j is independently a hydrocarbon group wherein a linear aliphatic hydrocarbon group selected from a linear $C_{10-40}$ alkyl group and a linear $C_{10-40}$ alkenyl group is bonded via a single bond or a linker;
- $R^8$ is a hydrogen atom, or optionally shows, together with $R^6$ of ring A or ring B, a single bond or —O— to form, together with ring A or ring B and ring C, a fused ring; and ring C optionally has, in addition to QR$^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or R$^a$ and R$^b$ are joined to form an oxo group;

a compound represented by formula (a-vi'):

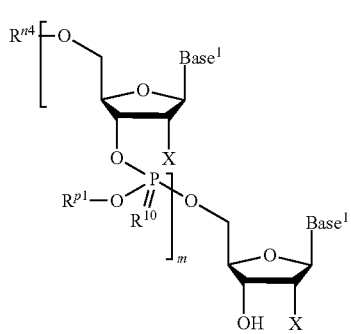

wherein at least one of base$^1$ in the number of m+1 is a nucleic acid base protected by -L-y-z, and the rest is an optionally protected nucleic acid base;

R$^{n4}$ is a hydroxy-protecting group;

m, X in the number of m+1, R$^{10}$ in the number of m, R$^{p1}$ in the number of m, L, Y and Z are each independently as defined above; or a compound represented by formula (a-vii'):

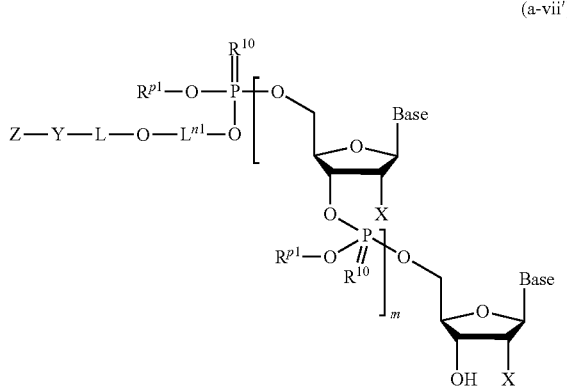

wherein

L$^{n1}$ is a $C_{2-6}$ alkylene group;

m, Base in the number of m+1, X in the number of m+1, R$^{10}$ in the number of m+1, R$^{p1}$ in the number of m+1, L, Y and Z are each independently as defined above;

wherein said nucleoside, nucleotide or oligonucleotide (b') is a compound represented by formula (b-i'):

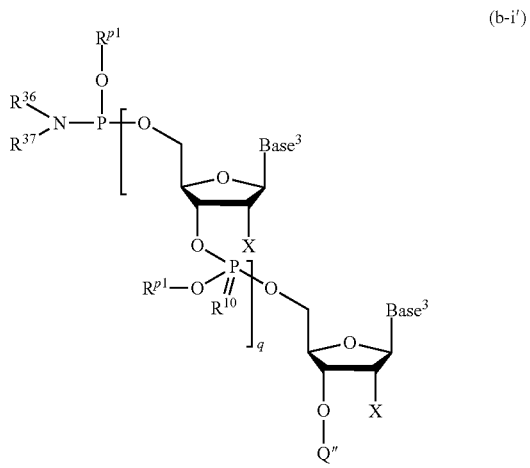

wherein q is an integer of not less than 0 and not more than 49;

each Base$^3$ in the number of q+1 is independently an optionally protected nucleic acid base;

X in the number of q+1, R$^{p1}$ in the number of q+1, and R$^{10}$ in the number of q are each independently as defined above;

Q" is the temporary protecting group;

R$^{36}$ and R$^{37}$ are each independently an alkyl group, or a 5- or 6-membered saturated cyclic amino group formed together with the adjacent nitrogen atom, and the saturated cyclic amino group, optionally has, as a ring-constituting atom, one oxygen atom or sulfur atom besides nitrogen atom;

wherein said temporary protecting group is a trityl group, a 9-(9-phenyl)xanthenyl group, a 9-phenylthioxanthenyl group, a bis($C_{1-6}$ alkoxy)trityl group, or a mono ($C_{1-18}$ alkoxy)trityl group;

wherein said acid in said (4') removing the temporary protecting group is at least one member selected from the group consisting of trifluoroacetic acid, dichloroacetic acid, trifluoromethanesulfonic acid, trichloroacetic acid, methanesulfonic acid, hydrochloric acid, acetic acid, p-toluenesulfonic acid, and mixtures thereof; and wherein said polar solvent in said (6') adding a polar solvent to said reaction solution is at least one member selected from the group consisting of methanol, ethanol, isopropanol, acetonitrile, propionitrile, acetone, 2-butanone, 1,4-dioxane, tetrahydrofuran, dimethylformamide, dimethylacetamide, N-methylpiperidone, dimethyl sulfoxide, water, and mixtures thereof.

16. The method according to claim 15, further comprising:

(2') adding a quencher to said reaction solution after condensation, after said (1') condensing and before said (3') oxidizing or sulfurizing.

17. The method according to claim 16, wherein said quencher is at least one member selected from the group consisting of an alcohol, a phenol, an amine, and mixtures thereof.

18. The method according to claim 15, wherein a mixture of a carboxylic acid and an organic base, an inorganic acid or an amine is added to said reaction solution after said (1')

condensing and before said (4') removing the temporary protecting group, and 5-[(N,N-dimethylaminomethylidene)amino]-3H-1,2,4-dithiazole-3-thione is added to said reaction solution as a sulfurizing agent in said (3') oxidizing or sulfurizing.

19. The method according to claim 18, wherein an amount of a basic nitrogen atom of said organic base is 1 to 2 mol per 1 mol of carboxy group of the carboxylic acid.

20. The method according to claim 15, wherein said sulfurizing agent in said (3') oxidizing or sulfurizing is at least one member selected from the group consisting of 3H-1,2-benzodithiol-3-one-1,1-dioxide, 3H-1,2-benzodithiol-3-one, phenylacetyl disulfide, tetraethylthiuram disulfide, dipentamethylenethiuram tetrasulfide, phenyl-3H-1,2,4-dithiazol-3-one, 3-amino-1,2,4-dithiazole-5-thione, sulfur, and mixtures thereof.

21. The method according to claim 15, wherein said oxidant in said (3') oxidizing or sulfurizing is at least one member selected from the group consisting of iodine, (1S)-(+)-(10-camphanylsulfonyl)oxaziridine, tert-butyl hydroperoxide, 2-butanone peroxide, 1,1-dihydroperoxycyclododecane, bis(trimethylsilyl)peroxide, m-chloroperbenzoic acid, and mixtures thereof.

22. The method according to claim 15, wherein said temporary protecting group is a dimethoxytrityl group or a monomethoxytrityl group.

23. The method according to claim 15, wherein said polar solvent in said (6') adding a polar solvent to said reaction solution is at least one member selected from the group consisting of acetonitrile, propionitrile, and mixtures thereof.

24. The method according to claim 15, further comprising:
    (5') neutralizing said reaction solution comprising said oligonucleotide (e) by adding a base, after said (4') removing the temporary protecting group and before said (6') adding a polar solvent to said reaction solution.

25. The method according to claim 24, wherein said base in said (5') neutralizing said reaction solution is at least one member selected from the group consisting of pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole, 5-nitrobenzimidazole, and mixtures thereof.

26. The method according to claim 15, further comprising:
    (7') removing all protecting groups of the obtained oligonucleotide and isolating an unprotected oligonucleotide, after said (6') adding a polar solvent to said reaction solution.

27. The method according to claim 15, wherein said (4') removing the temporary protecting group is performed in the presence of a cation scavenger, or the method further comprises adding a cation scavenger to the reaction solution after the reaction to remove the temporary protecting group.

28. The method according to claim 27, wherein said cation scavenger is at least one member selected from the group consisting of pyrrole, 2-methylpyrrole, 3-methylpyrrole, 2,3-dimethylpyrrole, 2,4-dimethylpyrrole, indole, 3-methylindole, 4-methylindole, 5-methylindole, 6-methylindole, 7-methylindole, 5,6-dimethylindole, 6,7-dimethylindole, 2-methylfuran, 2,3-dimethylfuran, 2-methyl-3-(methylthio)furan, menthofuran, and mixtures thereof.

29. A nucleoside or oligonucleotide represented by formula (a-II):

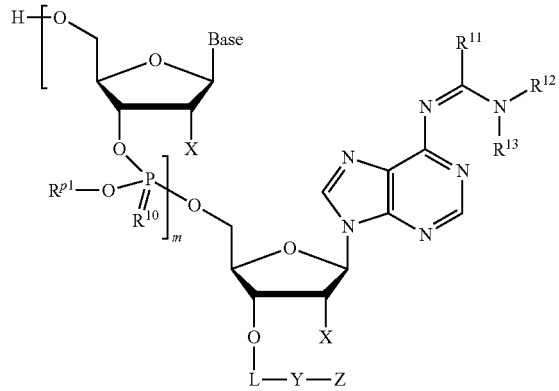

(a-II)

wherein
    m is an integer of not less than 0 and not more than 49;
    each Base in each number of m is independently an optionally protected nucleic acid base;
    each X in each number of m+1 is independently a hydrogen atom, a halogen atom, or an optionally protected hydroxy group;
    each $R^{10}$ in each number of m is independently an oxygen atom or a sulfur atom;
    each $R^{p1}$ in each number of m is independently a protecting group of phosphoric acid group;
    L is a single bond, or a group represented by formula (a1) or (a1'):

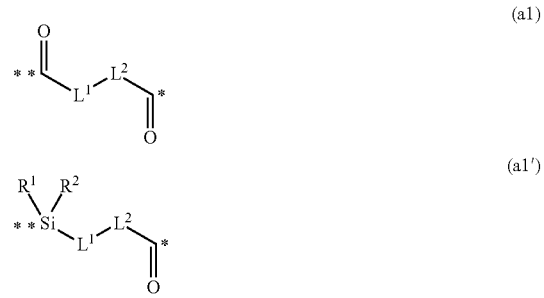

(a1)

(a1')

wherein
    * indicates the bonding position to Y;
    ** is the bonding position to an oxygen atom;
    $R^1$ and $R^2$ are each independently a $C_{1-22}$ hydrocarbon group;
    $L^1$ is an optionally substituted divalent $C_{1-22}$ hydrocarbon group;
    $L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
    Y is a single bond, an oxygen atom or NR wherein R is a hydrogen atom, an alkyl group or an aralkyl group; and
    Z is a group represented by formula (a2), formula (a2') or formula (a2"):

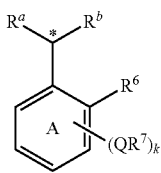

(a2)

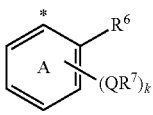

(a2')

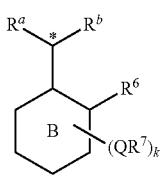

(a2'')

wherein
* indicates a bonding position;
$R^6$ is a hydrogen atom, or when $R^b$ is a group represented by the following formula (a3), $R^6$ of ring A or ring B optionally shows, together with $R^8$, a single bond or —O— to form, together with ring A or ring B and ring C, a fused ring;
k is an integer of 1 to 4;
each Q in each number of k is independently —O—, —C(=O)—, —C(=O)O—, —OC(=O)—, —C(=O)NH— or —NHC(=O)—;
each $R^7$ in each number of k is independently a hydrocarbon group wherein a linear aliphatic hydrocarbon group selected from a linear $C_{10-40}$ alkyl group and a linear $C_{10-40}$ alkenyl group is bonded via a single bond or a linker;
ring A and ring B, each independently, optionally has, in addition to QR' in each number of k, a substituent selected from the group consisting of a halogen atom, a $C_{1-6}$ alkyl group optionally substituted by a halogen atom, and a $C_{1-6}$ alkoxy group optionally substituted by a halogen atom;
$R^a$ is a hydrogen atom; and
$R^b$ is a hydrogen atom, or a group represented by formula (a3):

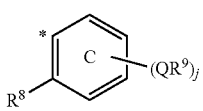

(a3)

wherein
* indicates a bonding position;
j is an integer of 0 to 4;
each Q in each number of j is independently as defined above;
each $R^9$ in each number of j is independently a hydrocarbon group wherein a linear aliphatic hydrocarbon group selected from a linear $C_{10-40}$ alkyl group and a linear $C_{10-40}$ alkenyl group is bonded via a single bond or a linker;

$R^8$ is a hydrogen atom, or optionally shows, together with $R^6$ of ring A or ring B, a single bond or —O— to form, together with ring A or ring B and ring C, a fused ring; and
ring C optionally has, in addition to $QR^9$ in each number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group, and
$R^{11}$ is a methyl group, $R^{12}$ and $R^{13}$ are each independently a $C_{1-5}$ alkyl group, or $R^{11}$ and $R^{12}$ are optionally joined to form, together with the carbon atom and nitrogen atom bonded thereto, a 5-membered or 6-membered nitrogen-containing hydrocarbon ring.

30. The nucleoside or oligonucleotide according to claim 29, wherein $R^{p1}$ is a group represented by —CH$_2$CH$_2$WG wherein WG is an electron-withdrawing group.

31. The nucleoside or oligonucleotide according to claim 29, wherein $R^{11}$ is a methyl group, and $R^{12}$ and $R^{13}$ are each independently a $C_{1-5}$ alkyl group.

32. The nucleoside according to claim 29, wherein m is 0.

33. A nucleoside or oligonucleotide represented by formula (a-IV):

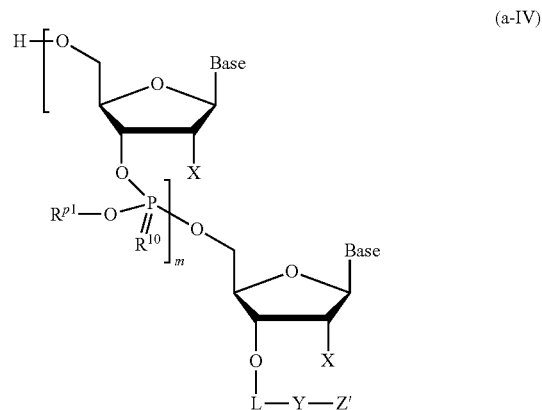

(a-IV)

wherein
m is an integer of not less than 0 and not more than 49;
each Base in each number of m+1 is independently an optionally protected nucleic acid base;
each X in each number of m+1 is independently a hydrogen atom, a halogen atom, or an optionally protected hydroxy group;
each $R^{10}$ in each number of m is independently an oxygen atom or a sulfur atom;
each $R^{p1}$ in each number of m is independently a protecting group of phosphoric acid group;
L is a single bond, or a group represented by formula (a1) or (a1'):

(a1)

141
-continued

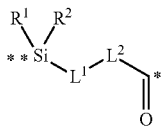
(a1')

wherein
* indicates the bonding position to Y;
** is the bonding position to an oxygen atom;
$R^1$ and $R^2$ are each independently a $C_{1-22}$ hydrocarbon group;
$L^1$ is an optionally substituted divalent $C_{1-22}$ hydrocarbon group;
$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
Y is a single bond, an oxygen atom or NR wherein R is a hydrogen atom, an alkyl group or an aralkyl group; and
Z' is a group represented by formula (a2"):

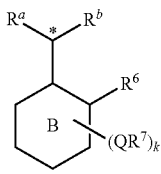
(a2")

wherein
* indicates a bonding position;
$R^6$ is a hydrogen atom, or when $R^b$ is a group represented by the following formula (a3), it optionally shows, together with $R^8$, a single bond or —O— to form, together with ring B and ring C, a fused ring;
k is an integer of 1 to 4;
each Q in each number of k is independently —O—, —C(=O)—, —C(=O)O—, —OC(=O)—, —C(=O)NH— or —NHC(=O)—;
each $R^7$ in each number of k is independently a hydrocarbon group wherein a linear aliphatic hydrocarbon group selected from a linear $C_{10-40}$ alkyl group and a linear $C_{10-40}$ alkenyl group is bonded via a single bond or a linker;
ring B optionally has, in addition to $QR^7$ in the number of k, a substituent selected from the group consisting of a halogen atom, a $C_{1-6}$ alkyl group optionally substituted by a halogen atom, and a $C_{1-6}$ alkoxy group optionally substituted by a halogen atom;
$R^a$ is a hydrogen atom; and
$R^b$ is a hydrogen atom, or a group represented by formula (a3):

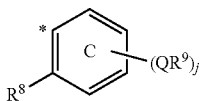
(a3)

142 wherein
* indicates a bonding position;
j is an integer of 0 to 4;
each Q in each number of j is independently as defined above;
each $R^9$ in each number of j is independently a hydrocarbon group wherein a linear aliphatic hydrocarbon group selected from a linear $C_{10-40}$ alkyl group and a linear $C_{10-40}$ alkenyl group is bonded via a single bond or a linker;
$R^8$ is a hydrogen atom, or optionally shows, together with $R^6$, a single bond or —O— to form, together with ring B and ring C, a fused ring; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group.

34. The nucleoside or oligonucleotide according to claim 33, wherein $R^{p1}$ is a group represented by —$CH_2CH_2WG$ wherein WG is an electron-withdrawing group.

35. The nucleoside according to claim 33, wherein m is 0.

36. A nucleotide or oligonucleotide represented by formula (I):

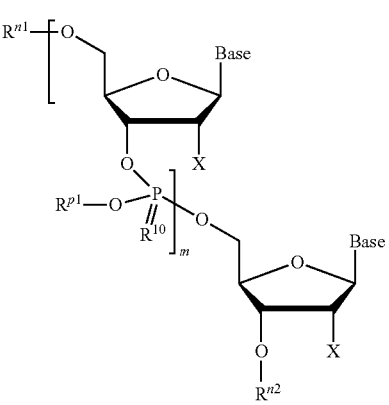
(I)

wherein
m is an integer of not less than 0 and not more than 49;
each Base in each number of m+1 is independently an optionally protected nucleic acid base;
each X in each number of m+1 is independently a hydrogen atom, a halogen atom, or an optionally protected hydroxy group;
each $R^{10}$ in each number of m is independently an oxygen atom or a sulfur atom;
each $R^{p1}$ in each number of m is independently a protecting group of phosphoric acid group;
one of $R^{n1}$ and $R^{n2}$ is a hydrogen atom, and the other is a group represented by formula (II):

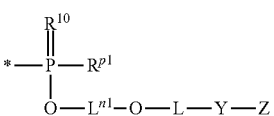
(II)

wherein,
* indicates a bonding position;
$R^{10}$ is an oxygen atom or a sulfur atom;
$R^{p1}$ is a protecting group of phosphoric acid group;
$L^{n1}$ is a $C_{2-6}$ alkylene group;
L is a single bond, or a group represented by formula (a1) or (a1'):

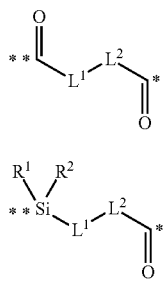

wherein
* indicates the bonding position to Y;
** is the bonding position to an oxygen atom;
$R^1$ and $R^2$ are each independently a $C_{1-22}$ hydrocarbon group;
$L^1$ is an optionally substituted divalent $C_{1-22}$ hydrocarbon group;
$L^2$ is a single bond or a group represented by *C(=O)N($R^3$)—$R^4$—N($R^5$) wherein * is the bonding position to $L^1$, **** is the bonding position to C=O, $R^4$ is a $C_{1-22}$ alkylene group, $R^3$ and $R^5$ are each independently a hydrogen atom or a $C_{1-22}$ alkyl group, or $R^3$ and $R^5$ are optionally joined to form a ring;
Y is a single bond, an oxygen atom or NR wherein R is a hydrogen atom, an alkyl group or an aralkyl group; and
Z is a group represented by formula (a2), formula (a2') or formula (a2"):

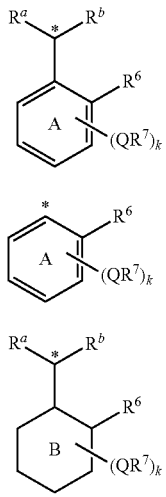

wherein
* indicates a bonding position;
$R^6$ is a hydrogen atom, or when $R^b$ is a group represented by the following formula (a3), $R^6$ of ring A or ring B optionally shows, together with $R^8$, a single bond or —O— to form, together with ring A or ring B and ring C, a fused ring;
k is an integer of 1 to 4;
each Q in each number of k is independently —O—, —C(=O)—, —C(=O)O—, —OC(=O)—, —C(=O)NH— or —NHC(=O)—;
each $R^7$ in each number of k is independently a hydrocarbon group wherein a linear aliphatic hydrocarbon group selected from a linear $C_{10-40}$ alkyl group and a linear $C_{10-40}$ alkenyl group is bonded via a single bond or a linker;
ring A and ring B each independently has, in addition to $QR^7$ in each number of k, a substituent selected from the group consisting of a halogen atom, a $C_{1-6}$ alkyl group optionally substituted by a halogen atom, and a $C_{1-6}$ alkoxy group optionally substituted by a halogen atom;
$R^a$ is a hydrogen atom; and
$R^b$ is a hydrogen atom, or a group represented by formula (a3):

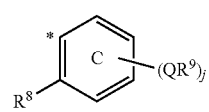

wherein
* indicates a bonding position;
j is an integer of 0 to 4;
each Q in each number of j is independently as defined above;
each $R^9$ in each number of j is independently a hydrocarbon group wherein a linear aliphatic hydrocarbon group selected from a linear $C_{10-40}$ alkyl group and a linear $C_{10-40}$ alkenyl group is bonded via a single bond or a linker;
$R^8$ is a hydrogen atom, or optionally shows, together with $R^6$ of ring A or ring B, a single bond or —O— to form, together with ring A or ring B and ring C, a fused ring; and
ring C optionally has, in addition to $QR^9$ in the number of j, a substituent selected from the group consisting of a halogen atom, a $C_{1-6}$ alkyl group optionally substituted by a halogen atom, and a $C_{1-6}$ alkoxy group optionally substituted by a halogen atom, or
$R^a$ and $R^b$ are joined to form an oxo group.

37. The nucleotide or oligonucleotide according to claim 36, wherein $R^{n1}$ is a group represented by formula (II), and $R^{n2}$ is a hydrogen atom.

38. The nucleotide or oligonucleotide according to claim 36, wherein $L^{n1}$ is an ethylene group.

39. The nucleotide according to claim 36, wherein m is 0.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthesized phosphorothioate

<400> SEQUENCE: 1
tcccgcctgt gacatgcatt                                              20

<210> SEQ ID NO 2
<211> LENGTH: 10
<212> TYPE: DNA
<213> ORGANISM: Artificial Sequence
<220> FEATURE:
<223> OTHER INFORMATION: Synthesized phosphorothioate

<400> SEQUENCE: 2
gacatgcatt                                                         10
```